US011826037B2

(12) United States Patent
Sengun et al.

(10) Patent No.: US 11,826,037 B2
(45) Date of Patent: Nov. 28, 2023

(54) MENISCAL REPAIR DEVICES, SYSTEMS, AND METHODS

(71) Applicant: Medos International Sarl, LeLocle (CH)

(72) Inventors: Mehmet Z. Sengun, Canton, MA (US); David B. Spenciner, North Attleboro, MA (US); Richard M. Lunn, Kingston, MA (US); Joseph Hernandez, Sandwich, MA (US); Scott A. Sigman, North Andover, MA (US)

(73) Assignee: Medos International Sarl, Le Locle (CH)

( * ) Notice: Subject to any disclaimer, the term of this patent is extended or adjusted under 35 U.S.C. 154(b) by 624 days.

(21) Appl. No.: 16/511,231

(22) Filed: Jul. 15, 2019

(65) Prior Publication Data
US 2019/0336120 A1 Nov. 7, 2019

Related U.S. Application Data

(62) Division of application No. 15/297,738, filed on Oct. 19, 2016, now Pat. No. 10,390,814.
(Continued)

(51) Int. Cl.
*A61B 17/04* (2006.01)
*A61B 17/34* (2006.01)
(Continued)

(52) U.S. Cl.
CPC ...... *A61B 17/0401* (2013.01); *A61B 17/0466* (2013.01); *A61B 17/0469* (2013.01);
(Continued)

(58) Field of Classification Search
CPC ............ A61B 17/0401; A61B 17/0466; A61B 17/0469; A61B 17/0482; A61B 17/3423; A61B 17/0487; A61B 17/34; A61B 17/3421; A61B 2017/00309; A61B 2017/00389; A61B 2017/00991; A61B 2017/0404; A61B 2017/0406; A61B 2017/0409; A61B 2017/0412; A61B 2017/0414; A61B 2017/0417; A61B 2017/0425; A61B 2017/0427; A61B 2017/044; A61B 2017/0445;
(Continued)

(56) References Cited

U.S. PATENT DOCUMENTS 2,788,787 A * 4/1957 Trace ............... A61B 17/00008
606/159
4,674,501 A 6/1987 Greenberg
(Continued)

FOREIGN PATENT DOCUMENTS

AU 2017200221 A1 8/2017
CN 103269647 A 8/2013
(Continued)

OTHER PUBLICATIONS

U.S. Appl. No. 16/741,140, filed Jan. 13, 2020, Mehmet Z. Sengun et al.
(Continued)

*Primary Examiner* — Richard G Louis

(57) ABSTRACT

Meniscal repair devices, systems, and methods are provided.

16 Claims, 31 Drawing Sheets

Related U.S. Application Data

(60) Provisional application No. 62/325,028, filed on Apr. 20, 2016.

(51) Int. Cl.
*A61B 17/00* (2006.01)
*A61B 90/00* (2016.01)

(52) U.S. Cl.
CPC ...... *A61B 17/0482* (2013.01); *A61B 17/3423* (2013.01); *A61B 17/0487* (2013.01); *A61B 17/34* (2013.01); *A61B 17/3421* (2013.01); *A61B 2017/00309* (2013.01); *A61B 2017/00389* (2013.01); *A61B 2017/00991* (2013.01); *A61B 2017/0404* (2013.01); *A61B 2017/044* (2013.01); *A61B 2017/0406* (2013.01); *A61B 2017/0409* (2013.01); *A61B 2017/0412* (2013.01); *A61B 2017/0414* (2013.01); *A61B 2017/0417* (2013.01); *A61B 2017/0425* (2013.01); *A61B 2017/0427* (2013.01); *A61B 2017/0445* (2013.01); *A61B 2017/0446* (2013.01); *A61B 2017/0448* (2013.01); *A61B 2017/0451* (2013.01); *A61B 2017/0458* (2013.01); *A61B 2017/0459* (2013.01); *A61B 2017/0464* (2013.01); *A61B 2017/0472* (2013.01); *A61B 2017/0475* (2013.01); *A61B 2017/347* (2013.01); *A61B 2017/3482* (2013.01); *A61B 2017/3484* (2013.01); *A61B 2090/034* (2016.02); *A61B 2090/0811* (2016.02)

(58) Field of Classification Search
CPC .... A61B 2017/0446; A61B 2017/0448; A61B 2017/0451; A61B 2017/0458; A61B 2017/0459

See application file for complete search history.

(56) References Cited

U.S. PATENT DOCUMENTS

| | | | |
|---|---|---|---|
| 4,815,450 A | 3/1989 | Patel | |
| 5,057,092 A | 10/1991 | Webster, Jr. | |
| 5,059,206 A | 10/1991 | Winters | |
| 5,269,783 A | 12/1993 | Sander | |
| 5,285,795 A | 2/1994 | Ryan et al. | |
| 5,374,268 A | 12/1994 | Sander | |
| 5,374,277 A | 12/1994 | Hassler | |
| 5,403,348 A | 4/1995 | Bonutti | |
| 5,500,000 A | 3/1996 | Feagin et al. | |
| 5,522,830 A | 6/1996 | Aranyi | |
| 5,531,684 A | 7/1996 | Ensminger et al. | |
| 5,649,958 A | 7/1997 | Grimm et al. | |
| 5,702,462 A | 12/1997 | Oberlander | |
| 5,810,879 A | 9/1998 | de Guillebon | |
| 5,891,112 A | 4/1999 | Samson | |
| 5,938,623 A | 8/1999 | Quiachon et al. | |
| 6,048,339 A | 4/2000 | Zirps et al. | |
| 6,056,778 A | 5/2000 | Grafton et al. | |
| 6,159,235 A | 12/2000 | Kim | |
| 6,287,325 B1 | 9/2001 | Bonutti | |
| 6,306,159 B1 | 10/2001 | Schwartz et al. | |
| 6,558,371 B2 | 5/2003 | Dorn | |
| 6,629,984 B1 | 10/2003 | Chan | |
| 6,800,056 B2 | 10/2004 | Tartaglia et al. | |
| 6,997,870 B2 | 2/2006 | Couvillon, Jr. | |
| 6,997,933 B2 | 2/2006 | Bittar | |
| 7,041,050 B1* | 5/2006 | Ronald ........ | A61B 17/320016 604/164.11 |
| 7,153,312 B1 | 12/2006 | Torrie et al. | |
| 7,285,124 B2 | 10/2007 | Foerster | |
| 7,347,863 B2 | 3/2008 | Rothe et al. | |
| 7,494,496 B2 | 2/2009 | Swain et al. | |
| 7,578,836 B2 | 8/2009 | Justin et al. | |
| 7,594,922 B1 | 9/2009 | Goble et al. | |
| 7,608,092 B1 | 10/2009 | Schaffhausen | |
| 7,637,926 B2 | 12/2009 | Foerster et al. | |
| 7,658,750 B2 | 2/2010 | Li | |
| 7,785,332 B2 | 8/2010 | Zannis et al. | |
| 7,857,830 B2 | 12/2010 | Stone et al. | |
| 7,871,440 B2 | 1/2011 | Schwartz et al. | |
| 7,887,551 B2 | 2/2011 | Bojarski et al. | |
| 7,959,650 B2 | 6/2011 | Kaiser et al. | |
| 8,052,719 B2 | 11/2011 | Paulos | |
| 8,137,382 B2 | 3/2012 | Denham et al. | |
| 8,221,454 B2 | 7/2012 | Schaffhausen | |
| 8,231,654 B2 | 7/2012 | Kaiser et al. | |
| 8,262,675 B2 | 9/2012 | Cropper et al. | |
| 8,292,921 B2 | 10/2012 | Stone et al. | |
| 8,317,829 B2 | 11/2012 | Foerster et al. | |
| 8,366,744 B2 | 2/2013 | Bojarski et al. | |
| 8,409,253 B2 | 4/2013 | Stone et al. | |
| 8,460,319 B2 | 6/2013 | Wales et al. | |
| 8,512,375 B2 | 8/2013 | Torrie et al. | |
| 8,512,377 B2 | 8/2013 | Paulos | |
| 8,574,243 B2 | 11/2013 | Saadat et al. | |
| 8,623,032 B2 | 1/2014 | Diduch et al. | |
| 8,623,051 B2 | 1/2014 | Bojarski et al. | |
| 8,632,569 B2 | 1/2014 | Stone et al. | |
| 8,652,153 B2 | 2/2014 | Brady et al. | |
| 8,652,171 B2 | 2/2014 | Stone et al. | |
| 8,657,854 B2 | 2/2014 | Foerster et al. | |
| 8,771,314 B2 | 7/2014 | Crombie et al. | |
| 8,777,992 B2 | 7/2014 | Yeung et al. | |
| 8,790,369 B2 | 7/2014 | Orphanos et al. | |
| 8,808,309 B2 | 8/2014 | Nelson et al. | |
| 8,814,903 B2 | 8/2014 | Sengun et al. | |
| 8,821,542 B2 | 9/2014 | Zirps et al. | |
| 8,828,052 B2 | 9/2014 | Caborn et al. | |
| 8,828,053 B2 | 9/2014 | Sengun et al. | |
| 8,961,538 B2 | 2/2015 | Koogle, Jr. et al. | |
| 10,299,782 B2 | 5/2019 | Sengun et al. | |
| 10,390,814 B2 | 8/2019 | Sengun et al. | |
| 10,568,617 B2 | 2/2020 | Sengun et al. | |
| 10,709,435 B2 | 7/2020 | Sengun et al. | |
| 11,419,599 B2 | 8/2022 | Sengun et al. | |
| 2001/0008971 A1 | 7/2001 | Schwartz et al. | |
| 2001/0041916 A1 | 11/2001 | Bonutti | |
| 2002/0019649 A1 | 2/2002 | Sikora et al. | |
| 2002/0072713 A1 | 6/2002 | Almond et al. | |
| 2002/0188301 A1* | 12/2002 | Dallara ................ | A61B 17/064 606/104 |
| 2003/0065361 A1 | 4/2003 | Dreyfuss | |
| 2003/0109861 A1* | 6/2003 | Shimada ............ | A61M 25/0147 606/14 |
| 2003/0144696 A1 | 7/2003 | Sinnott et al. | |
| 2003/0167062 A1 | 9/2003 | Gambale et al. | |
| 2004/0002734 A1 | 1/2004 | Fallin et al. | |
| 2004/0138683 A1 | 7/2004 | Shelton et al. | |
| 2004/0147958 A1 | 7/2004 | Lam et al. | |
| 2004/0249395 A1 | 12/2004 | Mikkaichi et al. | |
| 2005/0070943 A1 | 3/2005 | Hueil et al. | |
| 2005/0080476 A1 | 4/2005 | Gunderson et al. | |
| 2005/0187567 A1 | 8/2005 | Baker et al. | |
| 2006/0161190 A1 | 7/2006 | Gadberry et al. | |
| 2006/0190042 A1 | 8/2006 | Stone et al. | |
| 2006/0235269 A1 | 10/2006 | Waxman | |
| 2006/0253119 A1 | 11/2006 | Berberich et al. | |
| 2006/0259076 A1 | 11/2006 | Burkhart et al. | |
| 2007/0027476 A1 | 2/2007 | Harris et al. | |
| 2007/0038230 A1 | 2/2007 | Stone et al. | |
| 2007/0073320 A1 | 3/2007 | Mikkaichi et al. | |
| 2007/0173845 A1 | 7/2007 | Kim | |
| 2007/0185568 A1 | 8/2007 | Schwartz | |
| 2007/0239208 A1 | 10/2007 | Crawford | |
| 2007/0255317 A1 | 11/2007 | Fanton et al. | |
| 2007/0260223 A1* | 11/2007 | Scheibe ............ | A61M 25/0136 604/528 |
| 2008/0103527 A1 | 5/2008 | Martin et al. | |
| 2008/0140092 A1 | 6/2008 | Stone et al. | |
| 2008/0140093 A1 | 6/2008 | Stone et al. | |
| 2008/0208175 A1 | 8/2008 | Beckman et al. | |

(56) References Cited

U.S. PATENT DOCUMENTS

| | | |
|---|---|---|
| 2008/0300629 A1 | 12/2008 | Surti |
| 2009/0018654 A1 | 1/2009 | Schmieding et al. |
| 2009/0082632 A1 | 3/2009 | Voegele |
| 2009/0082806 A1 | 3/2009 | West, Jr. et al. |
| 2009/0149883 A1 | 6/2009 | Brunsvold |
| 2009/0157099 A1 | 6/2009 | Surti |
| 2009/0326461 A1* | 12/2009 | Gresham ............ A61B 17/3421 604/164.04 |
| 2009/0326561 A1 | 12/2009 | Carroll, II et al. |
| 2010/0023022 A1 | 1/2010 | Zeiner et al. |
| 2010/0094425 A1 | 4/2010 | Bentley et al. |
| 2010/0179573 A1 | 7/2010 | Levinsohn et al. |
| 2010/0211076 A1 | 8/2010 | Germain et al. |
| 2010/0249523 A1* | 9/2010 | Spiegal ............ A61B 17/3423 600/206 |
| 2010/0249832 A1 | 9/2010 | Stopek et al. |
| 2010/0268241 A1* | 10/2010 | Flom ................. A61B 17/3421 606/104 |
| 2010/0292731 A1 | 11/2010 | Gittings et al. |
| 2010/0305610 A1 | 12/2010 | Kim et al. |
| 2011/0144440 A1 | 6/2011 | Cropper et al. |
| 2011/0144444 A1 | 6/2011 | Sakai, Jr. et al. |
| 2012/0109130 A1 | 5/2012 | Casey et al. |
| 2012/0130424 A1 | 5/2012 | Sengun et al. |
| 2012/0165864 A1 | 6/2012 | Hernandez et al. |
| 2012/0290006 A1 | 11/2012 | Collins et al. |
| 2013/0030463 A1 | 1/2013 | Harris et al. |
| 2013/0110165 A1 | 5/2013 | Burkhart et al. |
| 2013/0123842 A1 | 5/2013 | Chan et al. |
| 2013/0144334 A1 | 6/2013 | Bouduban et al. |
| 2013/0165972 A1 | 6/2013 | Sullivan |
| 2013/0253581 A1 | 9/2013 | Robison |
| 2013/0261663 A1 | 10/2013 | Bittenson |
| 2013/0304034 A1* | 11/2013 | Cabiri ................ A61M 25/0147 604/528 |
| 2014/0018732 A1* | 1/2014 | Bagaoisan ......... A61M 25/0136 604/95.04 |
| 2014/0031863 A1 | 1/2014 | Gittings et al. |
| 2014/0221967 A1 | 8/2014 | Childs et al. |
| 2014/0316462 A1 | 10/2014 | Brady et al. |
| 2014/0364862 A1 | 12/2014 | Bennett et al. |
| 2015/0066061 A1 | 3/2015 | Caborn et al. |
| 2015/0073478 A1 | 3/2015 | Belson et al. |
| 2015/0142052 A1 | 5/2015 | Koogle, Jr. et al. |
| 2015/0250470 A1 | 9/2015 | Vargas |
| 2015/0257751 A1 | 9/2015 | Bachar et al. |
| 2015/0351739 A1 | 12/2015 | Napolitano |
| 2016/0074211 A1* | 3/2016 | Ko ........................ A61F 9/0008 604/513 |
| 2017/0290655 A1 | 10/2017 | Piccirillo et al. |
| 2017/0290656 A1 | 10/2017 | Piccirillo et al. |
| 2017/0303907 A1 | 10/2017 | Sengun et al. |
| 2017/0303908 A1 | 10/2017 | Sengun et al. |
| 2017/0303909 A1 | 10/2017 | Sengun et al. |
| 2017/0303914 A1 | 10/2017 | Sengun et al. |
| 2017/0332767 A1 | 11/2017 | Schreiber |
| 2017/0348006 A1 | 12/2017 | Lorenzo et al. |
| 2018/0004310 A1 | 1/2018 | Drum |
| 2018/0014839 A1 | 1/2018 | Fiedler et al. |
| 2018/0018482 A1 | 1/2018 | Jammet |
| 2018/0021502 A1 | 1/2018 | Guala |
| 2018/0042614 A1 | 2/2018 | Erdmann et al. |
| 2019/0014847 A1 | 1/2019 | da Silva et al. |
| 2019/0365367 A1 | 12/2019 | Sengun et al. |
| 2020/0146672 A1 | 5/2020 | Sengun et al. |
| 2020/0305861 A1 | 10/2020 | Sengun et al. |
| 2021/0154008 A1 | 5/2021 | Braile et al. |

FOREIGN PATENT DOCUMENTS

| | | |
|---|---|---|
| CN | 104997540 A | 10/2015 |
| EP | 1206924 A1 | 5/2002 |
| EP | 2455004 A2 | 5/2012 |
| EP | 1327425 B1 | 3/2013 |
| EP | 2572648 A1 | 3/2013 |
| EP | 2762099 A1 | 8/2014 |
| EP | 3260162 A1 | 12/2017 |
| JP | 2007513717 A | 5/2007 |
| JP | 4520085 B2 | 8/2010 |
| JP | 2011025036 A | 2/2011 |
| JP | 2012024607 A | 2/2012 |
| JP | 2013545528 A | 12/2013 |
| WO | WO-0032116 A1 | 6/2000 |
| WO | WO-0139671 A1 | 6/2001 |
| WO | WO-0243576 A2 | 6/2002 |
| WO | WO-2005058239 A2 | 6/2005 |
| WO | WO-2011072096 A1 | 6/2011 |
| WO | WO-2012151396 A2 | 11/2012 |
| WO | WO-2014022838 A1 | 2/2014 |
| WO | WO-2015095475 A1 | 6/2015 |
| WO | WO-2015193317 A1 | 12/2015 |
| WO | WO-2016138443 A2 * | 9/2016 ............. A61B 1/005 |
| WO | WO-2018195611 A1 | 11/2018 |
| WO | WO-2019028536 A1 | 2/2019 |
| WO | WO-2019033184 A1 | 2/2019 |

OTHER PUBLICATIONS

Barber et al., Biomechanical testing of suture-based meniscal repair devices containing ultrahigh-molecular-weight polyethylene suture: update 2011. Arthroscopy. Jun. 2012;28(6):827-34.

DePuy Mitek, Inc., OmniSpan Meniscal Repair System: Prominent in Strength, Subtle in Profile, 2010.

DePuy Mitek, Inc., OmniSpan Meniscal Repair Utilizing the CHIA Percpasser Suture Passer, 2010.

DePuy Mitek, Inc., Outside-In Meniscal Repair Using the CHIA Percpasser, 2010.

DePuy Mitek, Inc., Value Analysis Brief—OMNISPAN Meniscal Repair System, 2011.

Smith & Nephew, Inc., Fast-Fix 360 Meniscal Repair System: All Inside Meniscal Repair, 2010.

Spenciner. Biomechanical Comparison of the OMNISPAN Meniscal Repair System and Ultra Fast-Fix. DePuy Mitek, Inc. 2011.

Extended European Search Report for Application No. 17167361.9 dated Jul. 11, 2017.

Partial European Search Report for Application No. 17167362.7 dated Jul. 17, 2017.

European Search Report for Application No. 17167375.9 dated Aug. 31, 2017.

Extended European Search Report for Application No. 17167371.8 dated Oct. 20, 2017.

Partial European Search Report for Application No. 20179050.8 dated Sep. 10, 2020.

U.S. Appl. No. 16/899,961, filed Jun. 12, 2020, Mehmet Z. Sengun et al.

Japanese Office Action for JP App. No. 2017-082668 dated Feb. 24, 2021.

Japanese Office Action for JP App. No. 2017-082644 dated Mar. 2, 2021.

Japanese Office Action for JP App. No. 2017-082662 dated Mar. 16, 2021 (English translation).

* cited by examiner

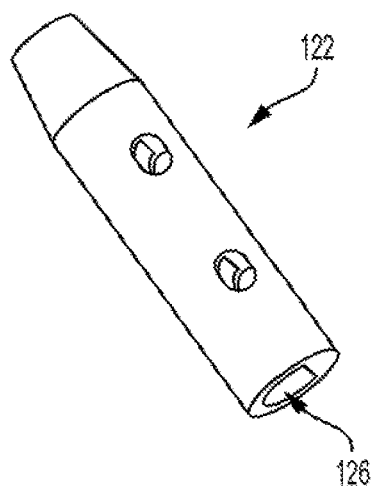
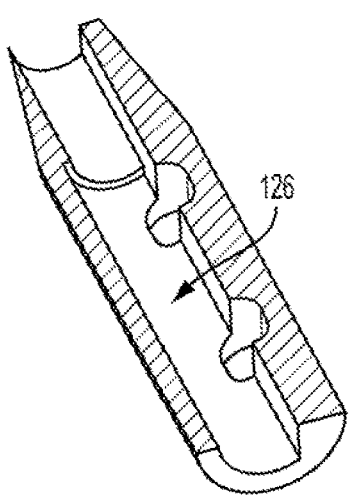
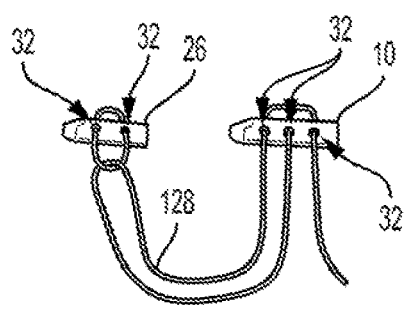
FIG. 27  FIG. 28  FIG. 29
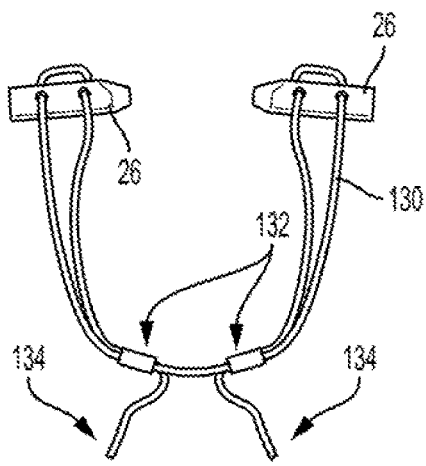
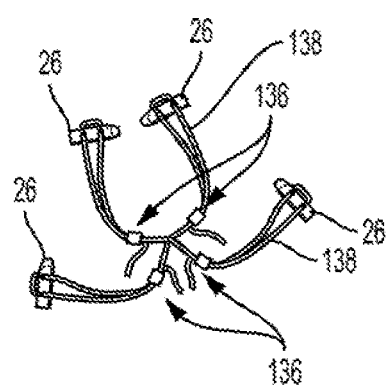
FIG. 30  FIG. 31
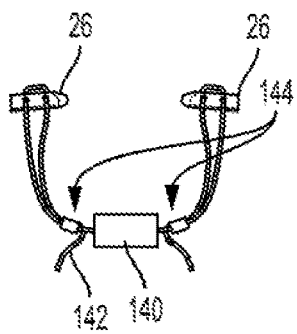
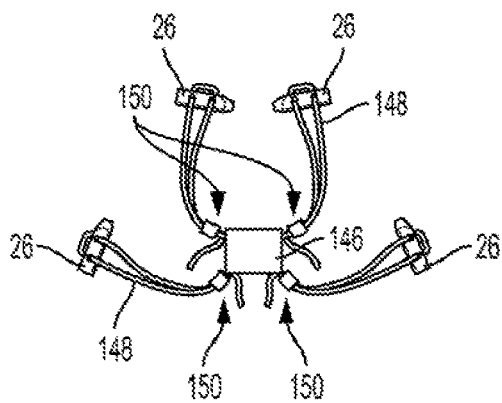
FIG. 32  FIG. 33

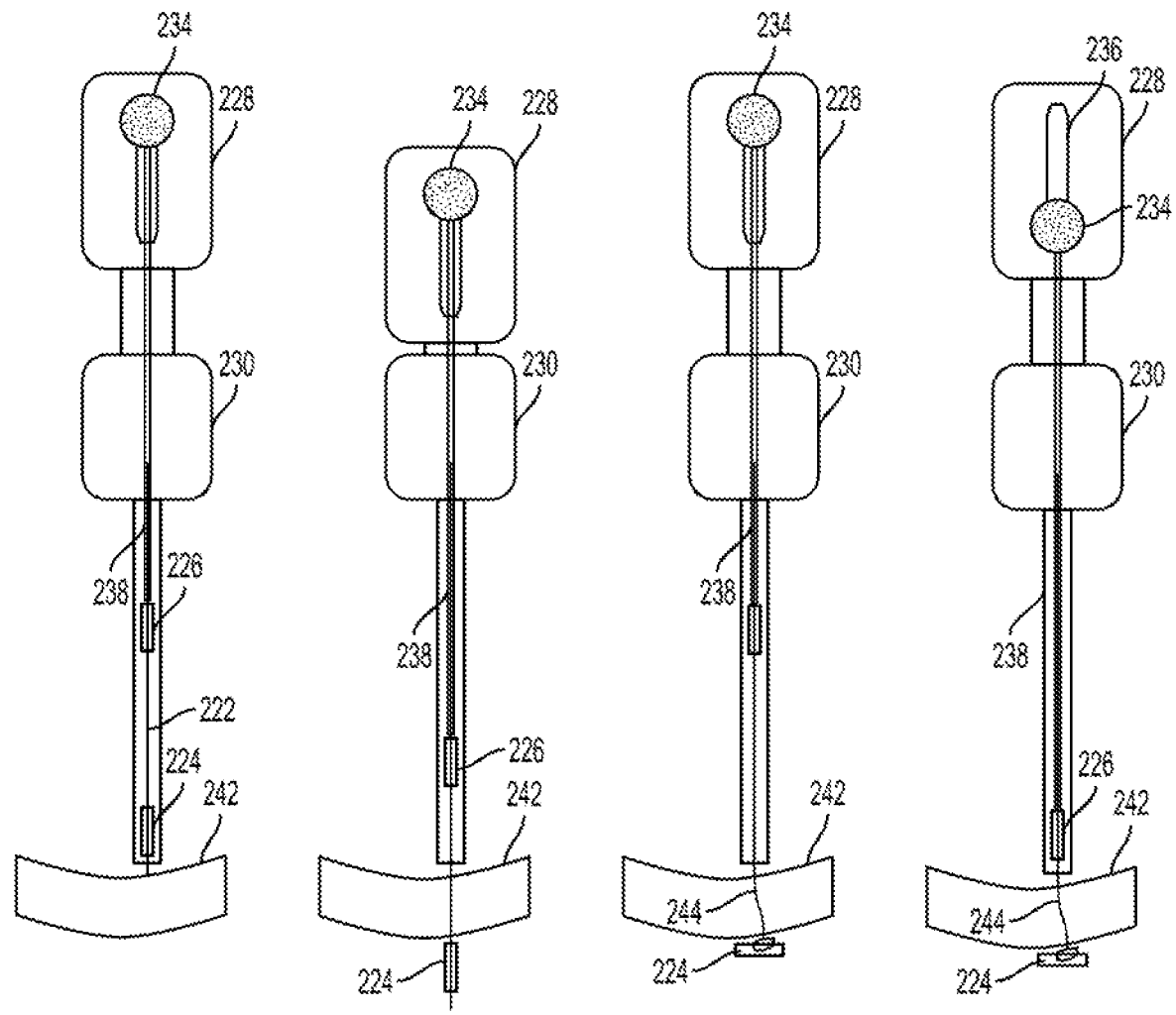

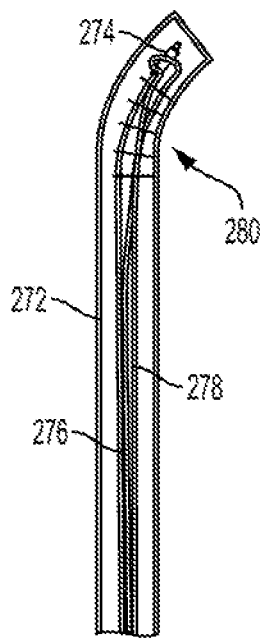 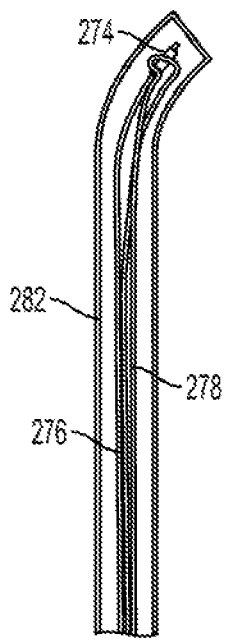 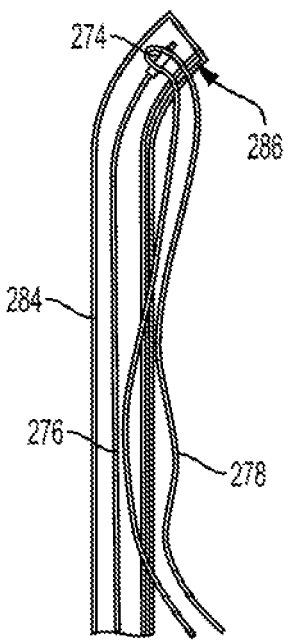
FIG. 91  FIG. 92  FIG. 93
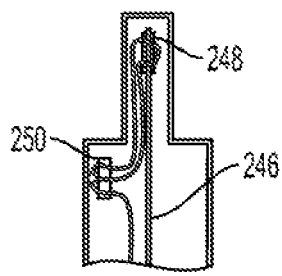 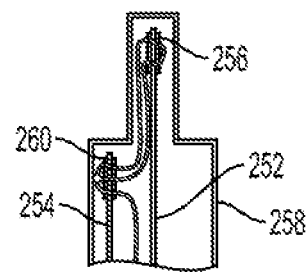
FIG. 94  FIG. 95

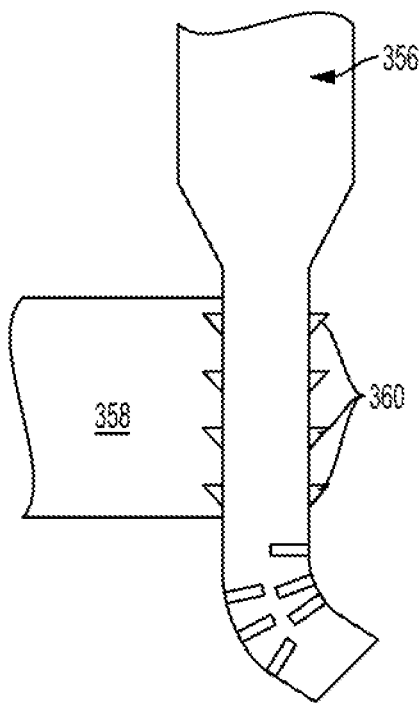
FIG. 109
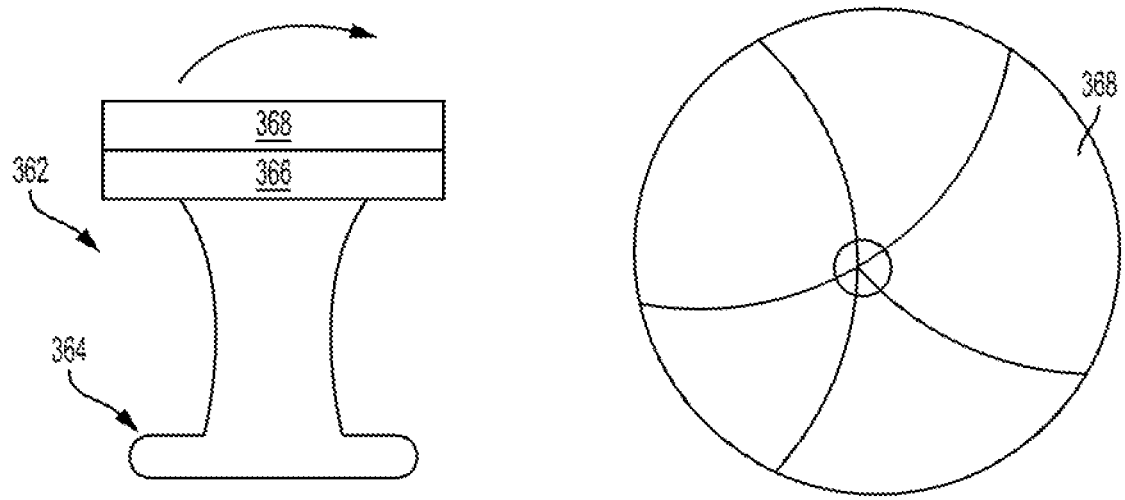
FIG. 110A
FIG. 110B

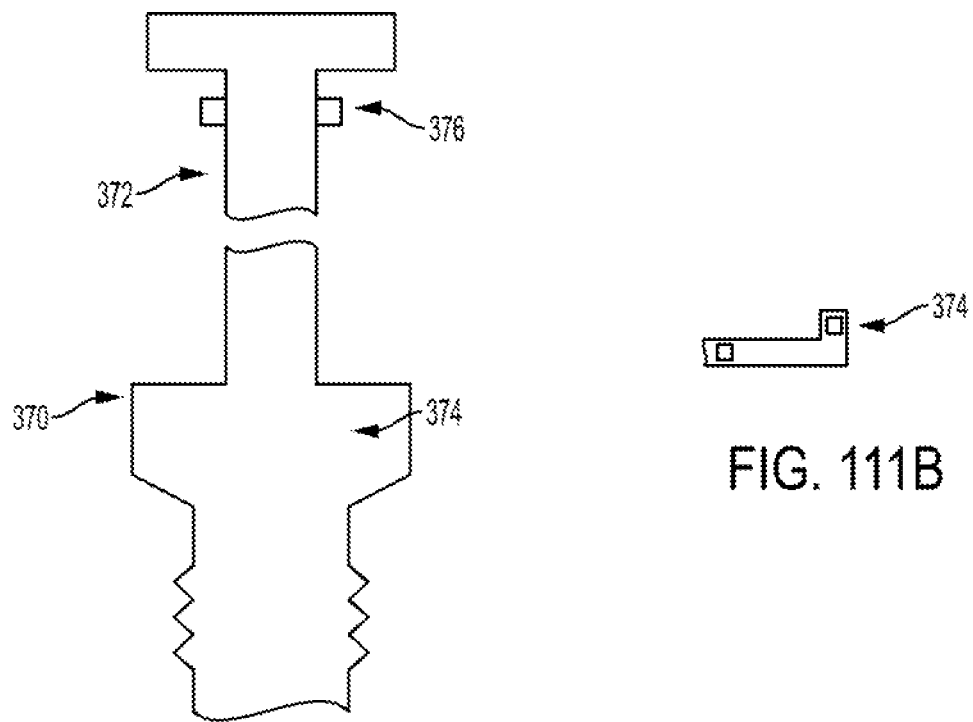
FIG. 111A
FIG. 111B
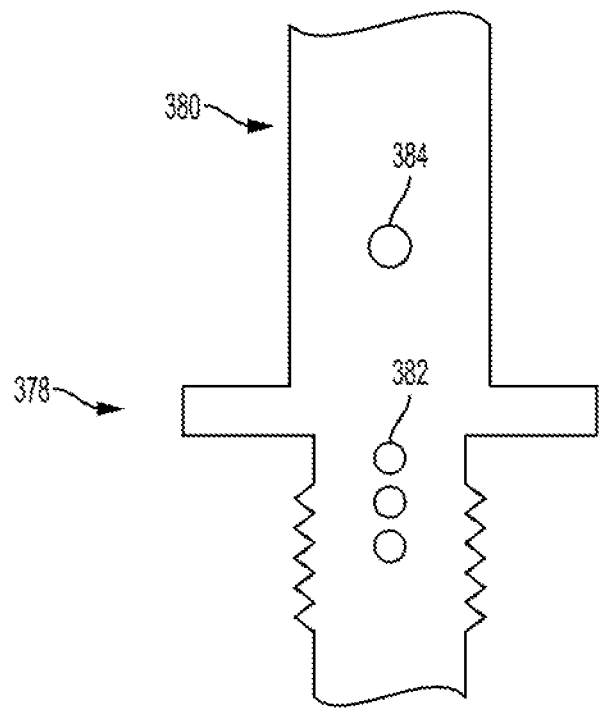
FIG. 112

MENISCAL REPAIR DEVICES, SYSTEMS, AND METHODS

CROSS-REFERENCE

The present application is a divisional of U.S. patent application Ser. No. 15/297,738, now U.S. Pat. No. 10,390,814, entitled "Meniscal Repair Devices, Systems, And Methods" filed Oct. 19, 2016, which claims priority to U.S. Provisional Patent Application No. 62/325,028 entitled "Meniscal Repair Devices, Systems, And Methods" filed Apr. 20, 2016, which are hereby incorporated by reference in their entireties.

FIELD

The present disclosure relates generally to meniscal repair devices, systems, and methods.

BACKGROUND

The meniscus is specialized tissue found between the bones of a joint. For example, in the knee the meniscus is a C-shaped piece of fibrocartilage which is located at the peripheral aspect of the joint between the tibia and femur. This tissue performs important functions in joint health including adding joint stability, providing shock absorption, and delivering lubrication and nutrition to the joint. As a result, meniscal injuries can lead to debilitating conditions such as degenerative arthritis.

Meniscal injuries, and in particular tears, are a relatively common injury. Such injuries can result from a sudden twisting-type injury such as a fall, overexertion during a work-related activity, during the course of an athletic event, or in any one of many other situations and/or activities. In addition, tears can develop gradually with age. In either case, the tears can occur in either the outer thick part of the meniscus or through the inner thin part. While some tears may involve only a small portion of the meniscus, others affect nearly the entire meniscus.

Unfortunately, a damaged meniscus is unable to undergo the normal healing process that occurs in other parts of the body. The peripheral rim of the meniscus at the meniscosynovial junction is highly vascular (red zone) whereas the inner two-thirds portion of the meniscus is completely avascular (white zone), with a small transition (red-white zone) between the two. Degenerative or traumatic tears to the meniscus which result in partial or complete loss of function frequently occur in the white zone where the tissue has little potential for regeneration. Such tears result in severe joint pain and locking, and in the long term, a loss of meniscal function leading to osteoarthritis.

Although several treatments currently exist for meniscal injuries, the treatment options provide little opportunity for meniscal repair or regeneration. The majority of meniscal injuries are treated by removing the unstable tissue during a partial meniscectomy. Once the tissue is removed no further treatment is conducted. Most patients respond well to this treatment in the short term but often develop degenerative joint disease several years (e.g., after more than about ten years) post operatively. The amount of tissue removed has been linked to the extent and speed of degeneration. When the majority of the meniscal tissue is involved in the injury, a total meniscectomy is conducted. If the patient experiences pain after a total meniscectomy without significant joint degeneration, a secondary treatment of meniscal allografts is possible. The use of allografts is limited by tissue availability and by narrow indications.

For meniscal tears that can be stabilized in vascularized areas of the meniscus, the tears can be repaired with suture or meniscal repair devices such as the Omnispan™ Meniscal Repair System (DePuy Mitek of Raynham, Mass.) and Fast-Fix™ 360 Meniscal Repair System (Smith & Nephew of London, UK). However, it can be difficult to deliver and position the devices at a desired angle and location relative to the meniscal tear, which may result in devices positioned at a compromised angle and location instead of a more desirable angle and location and/or may result in one or more failed attempts at device delivery before desired angle and location is achieved.

Accordingly, there remains a need for improved meniscal repair devices, systems, and methods.

SUMMARY

In general, meniscal repair devices, systems, and methods are provided.

In one aspect, a surgical system is provided that in one embodiment includes a pledget configured to be implanted in a body of a patient. The pledget has an inner lumen extending therethrough such that the pledget is cannulated, the pledget has a longitudinal axis, the pledget has a first plurality of holes formed through a sidewall of the pledget on a first side thereof, the pledget has a second plurality of holes formed through the sidewall of the pledget on a second side thereof, the first side is opposite to the second side, and each of the first plurality of holes is aligned with a corresponding one of the second plurality of holes.

The surgical system can vary in any number of ways. For example, the inner lumen can have a constant diameter. For another example, the inner lumen can have a first diameter in a distal portion of the pledget and a second, larger diameter in a proximal portion of the pledget. A junction between the first and second diameters can define a step within the inner lumen. For yet another example, the first plurality of holes and the second plurality of holes can each partially intersect with the inner lumen and the first plurality of holes and the second plurality of holes can each partially not intersect with the inner lumen. For still another example, the pledget can include a retention feature at a proximal end thereof, and the retention feature can include one of the proximal end being flared radially outward and a plurality of barbs spaced equidistantly around the pledget's perimeter.

For another example, the surgical system can include a suture configured to extend through each aligned pair of the first and second holes and extend across the inner lumen substantially perpendicular to the longitudinal axis such that the suture has at least two lengths thereof extending across the inner lumen. In some embodiments, the suture can have a length thereof passing through an interior of another length thereof to allow tensioning of the suture relative to the pledget. In some embodiments, the surgical system can include a second pledget. The second pledget can have an inner lumen extending therethrough such that the second pledget is cannulated, the second pledget can have a longitudinal axis, the second pledget can have a first plurality of holes formed through a sidewall of the second pledget on a first side thereof, the second pledget can have a second plurality of holes formed through the sidewall of the second pledget on a second side thereof, the first side of the second pledget can be opposite to the second side of the second pledget, and each of the first plurality of holes of the second pledget can be aligned with a corresponding one of the second plurality of holes. Simultaneously with the suture extending through each aligned pair of the first and second holes of the pledget, the suture can be configured to extend through each aligned pair of the first and second holes of the second pledget and extend across the inner lumen of the second pledget substantially perpendicular to the longitudinal axis of the second pledget such that the suture has at least two lengths thereof extending across the inner lumen of the second pledget. The suture can have a first length thereof passing through an interior of a second length thereof to allow tensioning of the suture relative to the pledget and can have a third length thereof passing through an interior of a fourth length thereof to allow tensioning of the suture relative to the second pledget independent of the tensioning of the suture relative to the pledget, and/or the first plurality of holes of the second pledget and the second plurality of holes of the second pledget can each partially intersect with the inner lumen of the second pledget and the first plurality of holes of the second pledget and the second plurality of holes of the second pledget can each partially not intersect with the inner lumen of the second pledget.

For yet another example, the surgical system can include a needle having the pledget slidably and releasably seated thereon, and can include a suture extending through the first plurality of holes and the second plurality of holes. The suture can be pinched in a press fit between the pledget and the needle. In some embodiments, the needle can have a flat surface, and the suture can be pinched in a press fit between the pledget and the flat surface of the needle. In some embodiments, the needle can have sharp distal tip that is located distally beyond the pledget slidably and releasably seated on the needle. In some embodiments, the surgical system can include a second pledget. The second pledget can have an inner lumen extending therethrough such that the second pledget is cannulated, the second pledget can have a longitudinal axis, the second pledget can have a first plurality of holes formed through a sidewall of the second pledget on a first side thereof, the second pledget can have a second plurality of holes formed through the sidewall of the second pledget on a second side thereof, the first side of the second pledget can be opposite to the second side of the second pledget, and each of the first plurality of holes of the second pledget can be aligned with a corresponding one of the second plurality of holes. The needle can also have the second pledget slidably and releasably seated thereon, the suture can also extend through the first plurality of holes of the second pledget and the second plurality of holes of the second pledget, and the suture can be pinched in a press fit between the second pledget and the needle. The pledget can be seated on the needle distal to the second pledget. The pledget can have an internal stop surface abutting an external stop surface of the needle. The second pledget can not have a stop surface that abuts the external stop surface of the needle.

For still another example, the surgical system can include a first needle having a first suture trailing therefrom. The first suture can be disposed in the inner lumen of the pledget, and a second suture can extend through the first plurality of holes and the second plurality of holes. The surgical system can also include a second pledget. The second pledget can have an inner lumen extending therethrough such that the second pledget is cannulated, the second pledget can have a longitudinal axis, the second pledget can have a first plurality of holes formed through a sidewall of the second pledget on a first side thereof, the second pledget can have a second plurality of holes formed through the sidewall of the second pledget on a second side thereof, the first side of the second pledget can be opposite to the second side of the second pledget, and each of the first plurality of holes of the second pledget can be aligned with a corresponding one of the second plurality of holes. The surgical system can further include a second needle having a third suture trailing therefrom. The third suture can be disposed in the inner lumen of the second pledget. The second suture can extend through the first plurality of holes of the second pledget and the second plurality of holes of the second pledget.

In another embodiment, a surgical system is provided that includes an implant having an open proximal end and having an external thread, and a driver including a distal portion configured to extend through the open proximal end of the implant to mate the implant to the driver. The driver is configured to rotate to drive the implant when mated thereto through tissue to move the implant from being located entirely within a first cavity on one side of a tissue to being located entirely within a second cavity on an opposite side of the tissue, and the driver is configured to be withdrawn from the implant to leave the implant entirely within the second cavity.

The surgical system can have any number of variations. For example, the implant can have a pointed distal tip and can be non-cannulated. For another example, the implant can have an inner lumen extending therethrough such that the implant is cannulated, and the driver can have a pointed distal tip that is located distal to the implant when the implant is mated to the driver. For yet another example, the implant can have a suture mating feature in an intermediate portion thereof that is configured to mate to a suture, and the rotation of the driver can be configured to cause the implant to rotate relative to the suture mated to the suture mating feature. The suture mating feature can include one of a soft coupling, a groove extending circumferentially around the implant, a plurality of sutures extending between proximal and distal rigid portions of the implant, a ring of material attaching together proximal and distal rigid portions of the implant and configured to flex radially inward in response to tension of the suture therearound, and a plurality of fabric strips extending between proximal and distal rigid portions of the implant. For another example, the surgical system can include a suture configured to couple to the implant and extend from the first cavity to the second cavity in response to the implant being moved to the second cavity. The surgical system can also include a second implant having the suture coupled thereto, and the rotation of the driver to drive the implant can not rotate the second implant.

In another embodiment, a surgical system is provided that includes a cannula configured to have a surgical device advanced therethrough. The cannula includes concentric inner and outer tubes that have distal ends fixed together. The outer tube is configured to move relative to the inner tube and thereby cause a distal portion of the cannula to articulate. The surgical system also includes an actuator configured to be actuated to cause the movement of the outer tube relative to the inner tube.

The surgical system can vary in any number of ways. For example, the inner tube can have a first plurality of slits formed in a distal portion thereof that are configured to facilitate the articulation, the outer tube can have a second plurality of slits formed in a distal portion thereof that are configured to facilitate the articulation, the first plurality of slits can be formed on a first side of the cannula, and the second plurality of slits can be formed on a second, opposite side of the cannula. For another example, the rotation of the actuator can be configured to cause translational movement of the outer tube along a longitudinal axis thereof. In some embodiments, the inner tube can not longitudinally translate in response to the actuation of the actuator. For yet another example, the surgical system can include a locking mechanism configured to lock the cannula in position relative to a tissue in which the cannula is positioned. For still another example, the surgical system can include a locking mechanism configured to lock the cannula in position relative to the surgical device advanced therethrough. For another example, the surgical system can include a first locking mechanism configured to lock the cannula in position relative to a tissue in which the cannula is positioned, and a second locking mechanism configured to lock the cannula in position relative to the surgical device advanced therethrough. For still another example, the surgical device can include a needle coupled to at least one pledget and at least one suture attached to the at least one pledget, and the needle can be configured to guide the at least one pledget and the at least one suture through a tissue.

In another embodiment, a surgical system is provided that includes a cannula configured to have a surgical device advanced therethrough and including at least one of a first locking mechanism configured to lock the cannula in position relative to a tissue in which the cannula is positioned, and a second locking mechanism configured to lock the cannula in position relative to the surgical device advanced therethrough.

The surgical system can have any number of variations. For example, the cannula can include at least the first locking mechanism, the first locking mechanism can include a plurality of protrusions on an external surface of the cannula, and the plurality of protrusions can be configured to contact the tissue. For another example, the cannula can include at least the first locking mechanism, and the first locking mechanism can include a distal retention feature having a proximal surface configured to abut a distal surface of the tissue. For yet another example, the cannula can include at least the first locking mechanism, and the first locking mechanism can include a proximal retention feature having a distal surface configured to abut a proximal surface of the tissue. For still another example, the cannula can include at least the second locking mechanism, and the second locking mechanism can include a soft material forming at least a proximal portion of the cannula. For another example, the cannula can include at least the second locking mechanism, and the second locking mechanism can include a mating feature configured to releasably engage a corresponding mating feature of the surgical device. For still another example, the surgical device can include a needle coupled to at least one pledget and at least one suture attached to the at least one pledget, and the needle can be configured to guide the at least one pledget and the at least one suture through a tissue.

For another example, a surgical method can be provided using the surgical system, and the surgical method can include advancing the cannula through tissue of a patient such that a proximal portion of the cannula is located outside of the patient and a distal portion of the cannula is located within the patient, and advancing the surgical device through the cannula. The surgical method can vary in any number of ways. For example, the cannula can include the first locking mechanism, and the cannula can be automatically locked in position relative to the tissue. For another example, the cannula can include the first locking mechanism, and the method can further include actuating an actuator to cause the cannula to be locked in position relative to the tissue. For yet another example, the cannula can include the second locking mechanism, and the cannula can be automatically locked in position relative to the surgical device advanced therethrough. For still another example, the cannula can include the second locking mechanism, and the method can further also include actuating an actuator to cause the cannula to be locked in position relative to the surgical device advanced therethrough.

In another embodiment, a surgical system is provided that includes a first implant configured to be implanted in a body of a patient, a second implant configured to be implanted in the body of the patient, a suture attached to each of the first and second implants, a needle having the first implant releasably mated thereto and having the second implant releasably mated thereto at a location that is proximal to the first implant, a cannula configured to guide the needle having the first and second implants releasably mated thereto with the suture attached to each of the first and second implants therethrough to a surgical site, and a first actuator configured to be actuated in a first actuation to advance the first implant and a distal portion of the needle out of the cannula and configured to be actuated in a second actuation after the first actuation to advance the second implant and the distal portion of the needle out of the cannula.

The surgical system can vary in any number of ways. For example, the first implant and the second implant can each be releasably mated to the needle by being slidably disposed thereon. For another example, the first actuator can be configured to be actuated in a third actuation between the first and second actuations to release the first implant from the needle. For yet another example, the surgical system can include a second actuator configured to be actuated in a third actuation to release the second implant from the needle. For still another example, the surgical system can include a pusher tube configured to be pushed distally in response to one or both of the first actuation to push the first implant distally along and off of the needle, and the second actuation to push the second implant distally along and off of the needle. For yet another example, the cannula can have a distal portion configured to be selectively adjusted in curvature. For another example, the cannula can have a distal portion with a fixed non-zero curvature. The surgical system can include one or more additional cannulas each configured to guide the needle having the first and second implants releasably mated thereto with the suture attached to each of the first and second implants therethrough to the surgical site, and each of the cannula and the one or more additional cannulas can have a distal portion with a different fixed non-zero curvature. For yet another example, the cannula can have a distal portion that has a fixed straight configuration. For still another example, the cannula can be configured to at least one of lock in position relative to the needle positioned therein and lock in position relative to a tissue through which the cannula extends.

For another example, a surgical method using the surgical system includes advancing the cannula into the body of the patient and positioning a distal end of the cannula adjacent to a target tissue of the patient, and advancing the needle through the cannula. The needle has the first and second implants releasably mated thereto with the suture attached to each of the first and second implants. The surgical method also includes actuating the actuator in the first actuation to advance the first implant and the distal portion of the needle out of the cannula and through the target tissue, and, after actuating the actuator in the first actuation, moving the cannula having the needle and the second implant disposed therein to a second location adjacent to the target tissue. The surgical method further includes, after moving the cannula, actuating the actuator in the second actuation to advance the second implant and the distal portion of the needle out of the cannula and through the target tissue. The suture is attached to each of the first and second implants extending through the target tissue. The surgical method can vary in any number of ways, such as the target tissue being a meniscus and/or the target tissue being at one of a knee, a hip, and a shoulder of the patient.

In another aspect, a surgical method is provided that in one embodiment includes advancing a needle having first and second pledgets releasably mated thereto through a tissue of a patient to move the first pledget through the tissue to a far side of the tissue. The first pledget is releasably mated to the needle by a press fit of a suture between the first pledget and the needle, and the second pledget is releasably mated to the needle by a press fit of the suture between the second pledget and the needle. The surgical method also includes retracting the needle through the tissue, the first pledget remaining on the far side of the tissue and the suture extending through the tissue from the first pledget, and, after the retraction of the needle, advancing the needle through the tissue again to move the second pledget through the tissue to the far side of the tissue. The surgical method further includes retracting the needle again through the tissue, the second pledget remaining on the far side of the tissue and the suture extending through the tissue from the second pledget.

The surgical method can have any number of variations. For example, the surgical method can include, after the retraction of the needle and before advancing the needle through the tissue again, repositioning the needle relative to the tissue. For another example, the retraction of the needle can overcome a force of the press fit of the suture between the first pledget and the needle, and the retraction of the needle can again overcome a force of the press fit of the suture between the second pledget and the needle.

For yet another example, the surgical method can include, after the retraction of the needle, tensioning the suture to toggle the first pledget relative to the tissue, and, after the retraction of the needle again, tensioning the suture to toggle the second pledget relative to the tissue. In some embodiments, the tensioning of the suture to toggle the first pledget and the tensioning of the suture to toggle the second pledget can occur simultaneously. In some embodiments, one of the tensioning of the suture to toggle the first pledget and the tensioning of the suture to toggle the second pledget can occur before the other. The suture can have a first length thereof passing through an interior of a second length thereof associated with the first pledget and has a third length thereof passing through an interior of a fourth length thereof associated with the second pledget. The interior passages can allow the one of the tensioning of the suture to toggle the first pledget and the tensioning of the suture to toggle the second pledget to occur before the other.

For still another example, the surgical method can include removing the needle from the patient, the first and second pledgets and the suture remaining in the patient. For another example, the tissue can be a meniscus. In some embodiments, the needle and the first pledget can be advanced through the meniscus on one side of a tear in the meniscus, and the needle and the second pledget can be advanced through the meniscus on an opposite side of the tear in the meniscus. For yet another example, the tissue can be at one of a knee, a hip, and a shoulder of the patient.

In another embodiment, a surgical method is provided that includes advancing a first needle having a first pledget releasably mated thereto through a tissue of a patient to move the first pledget through the tissue to a far side of the tissue. The first pledget is coupled to a suture that is also coupled to a second pledget. The method also includes removing the first needle from the patient, the first pledget remaining within the patient on the far side of the tissue and the suture extending through the tissue from the first pledget. The method also includes advancing a second needle having the second pledget releasably mated thereto through the tissue to move the second pledget through the tissue to the far side of the tissue, and removing the second needle from the patient, the second pledget remaining within the patient on the far side of the tissue and the suture extending through the tissue from the second pledget.

The method can have any number of variations. For example, the method can include, with the first pledget on the far side of the tissue, tensioning the suture to toggle the first pledget relative to the tissue, and, with the second pledget on the far side of the tissue, tensioning the suture to toggle the second pledget relative to the tissue. For another example, the first pledget can be releasably mated to the first needle via a second suture extending between the first pledget and the first needle, and the second pledget can be releasably mated to the second needle via a third suture extending between the second pledget and the second needle. In at least some embodiments, the method can also include cutting the second suture to release the first needle from the first pledget, and cutting the third suture to release the second needle from the second pledget. For yet another example, the tissue can be a meniscus. In at least some embodiments, the first needle and the first pledget can be advanced through the meniscus on one side of a tear in the meniscus, and the second needle and the second pledget can be advanced through the meniscus on an opposite side of the tear in the meniscus. For still another example, the tissue can be at one of a knee, a hip, and a shoulder of the patient.

In another embodiment, a surgical method is provided that includes rotating a driver to drive an implant mated thereto through tissue to move the implant from being located entirely within a first cavity on one side of a tissue to being located entirely within a second cavity on an opposite side of the tissue, and withdrawing the driver from the implant to move the driver from the second cavity to the first cavity, the implant remaining entirely within the second cavity. The implant has an open proximal end, and the driver being mated to the implant includes a distal portion of the driver extending through the open proximal end. The implant has an external thread that threads the tissue during the implant's passage therethrough.

The method can vary in any number of ways. For example, the implant can have a pointed distal tip and can be non-cannulated. For another example, the implant can have an inner lumen extending therethrough such that the implant is cannulated, and the driver can have a pointed distal tip that is located distal to the implant mated to the driver. For yet another example, the implant can have a suture mating feature in an intermediate portion thereof that is configured to mate to a suture, and the rotation of the driver can cause the implant to rotate relative to the suture mated to the suture mating feature. The suture mating feature can include one of a soft coupling, a groove extending circumferentially around the implant, a plurality of sutures extending between proximal and distal rigid portions of the implant, a ring of material attaching together proximal and distal rigid portions of the implant and configured to flex radially inward in response to tension of the suture therearound, and a plurality of fabric strips extending between proximal and distal rigid portions of the implant.

For still another example, a suture can be coupled to the implant and can extend from the first cavity to the second cavity in response to the implant being moved to the second cavity. The suture can be coupled to a second implant, and the rotation of the driver to drive the implant can not rotate the second implant. The surgical method can also include, after withdrawing the driver from the implant, mating the driver to the second implant, and rotating the driver to drive the second implant mated thereto through the tissue to move the implant from being located entirely within the first cavity to being located entirely within the second cavity. The rotation of the driver to drive the second implant can not rotate the implant.

For yet another example, the tissue can be a meniscus. For another example, the tissue can be at one of a knee, a hip, and a shoulder of the patient.

In another embodiment, a surgical method is provided that includes advancing a cannula through tissue of a patient such that a proximal portion of the cannula is located outside of the patient and a distal portion of the cannula is located within the patient. The cannula includes concentric inner and outer tubes that have distal ends fixed together. The surgical method also includes, with the distal portion of the cannula located within the patient, causing the distal portion to bend at an angle relative to a target tissue within the patient by moving the outer tube relative to the inner tube. The surgical method further includes, after causing the distal portion to bend, advancing a surgical device through the cannula.

The surgical method can vary in any number of ways. For example, the cannula can be advanced through the tissue with the distal portion at a zero angle, and the angle to which the cannula is bent can be a non-zero angle. For another example, the cannula can be bent from one non-zero angle to another non-zero angle. For yet another example, the cannula can be bent from a non-zero angle to a zero angle. For still another example, the surgical device can include a needle coupled to at least one pledget and at least one suture attached to the at least one pledget, and the needle can be configured to guide the at least one pledget and the at least one suture through a tissue. For another example, the target tissue can be a meniscus. For yet another example, the tissue can be at one of a knee, a hip, and a shoulder of the patient.

BRIEF DESCRIPTION OF DRAWINGS

This invention will be more fully understood from the following detailed description taken in conjunction with the accompanying drawings, in which:

FIG. 27 is a perspective view of the implant of FIG. 26;

FIG. 28 is a perspective cross-sectional view of the implant of FIG. 26;

FIG. 29 is a side view of the implant of FIG. 1 and the implant of FIG. 4 coupled to a suture;

FIG. 30 is a side view of two implants of FIG. 4 coupled to a suture including finger traps;

FIG. 31 is a side view of two implants of FIG. 4 coupled to a first suture including finger traps and two additional implants of FIG. 4 coupled to a second suture including finger traps;

FIG. 32 is a side view of two implants of FIG. 4 coupled to a suture including finger traps, the suture attached to a protective member;

FIG. 33 is a side view of two implants of FIG. 4 coupled to a first suture including finger traps and two additional implants of FIG. 4 coupled to a second suture including finger traps, the sutures attached to a protective member;

FIG. 83 is a side schematic view of meniscus tissue with the delivery system of FIG. 82 positioned adjacent thereto;

FIG. 84 is a side schematic view of the meniscus tissue of FIG. 83 with one of the implants advanced therethrough and with a needle of the delivery system advanced therethrough;

FIG. 85 is a side schematic view of the meniscus tissue of FIG. 84 with the needle withdrawn;

FIG. 86 is a side schematic view of the meniscus tissue of FIG. 85 with the other of the implants advanced within the shaft;

FIG. 91 is a side transparent schematic view of one embodiment of a steerable cannula having an implant, needle, and suture at least partially disposed therein;

FIG. 92 is a side transparent schematic view of one embodiment of a non-steerable cannula having the implant, needle, and suture of FIG. 91 at least partially disposed therein;

FIG. 93 is a side transparent schematic view of another embodiment of a non-steerable cannula having the implant, needle, and suture of FIG. 91 at least partially disposed therein;

FIG. 94 is a side transparent schematic view of another embodiment of a delivery system having a needle and two implants disposed therein;

FIG. 95 is a side transparent schematic view of another embodiment of a delivery system having two needles and two implants disposed therein;

FIG. 109 is a side schematic view of another embodiment of a lockable cannula;

FIG. 110A is a side schematic view of yet another embodiment of a lockable cannula;

FIG. 110B is a bottom view of the lockable cannula of FIG. 110A;

FIG. 111A is a partial side schematic view of another embodiment of a lockable cannula;

FIG. 111B is a side view of a lock of the lockable cannula of FIG. 111A;

FIG. 112 is a side schematic view of yet another embodiment of a lockable cannula.

DETAILED DESCRIPTION

Figure 1:
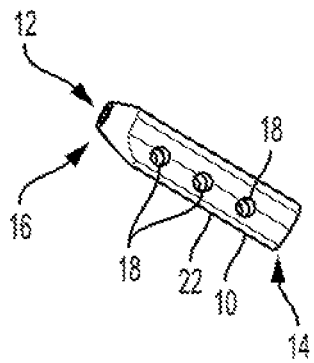
FIG. 1 is a perspective view of one embodiment of an implant.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Meniscal repair devices, systems, and methods are provided.

Implants

Implants, also referred to herein as pledgets, configured to be implanted in a body of a patient are discussed below. The implants are configured to couple to a suture and to be used in a meniscal repair procedure, and in particular for surgical procedures for repairing a meniscal tear at a knee. The implants discussed below are thus discussed with respect to meniscal repair although they can be used in other surgical procedures, e.g., procedures in which a suture is used to tie tissue and/or other structures, such as in tissue repair surgical procedure at a shoulder or a hip.

An implant can be absorbable or non-absorbable. An implant can be made from any of a variety of materials, e.g., Polyether ether ketone (PEEK), Polylactic acid or polylactide (PLA), BIOCRYL® RAPIDE®, stainless steel, etc. An implant can be formed by a variety of techniques, for example by an injection molding process such as overmolding or by a post-molding process such as post-molding machining.

An implant can have a variety of sizes. In an exemplary embodiment, the implant has an outer diameter of about 0.052 in., the inner lumen of the implant has a diameter of about 0.035 in. (e.g., the implant has an inner diameter of about 0.035 in.), the implant has a length of about 5.3 mm, and each of the implant's holes has an ovular shape and has a width that is about half a height thereof (e.g., a width of about 0.015 in. and a height of about 0.025 in., or a width of about 0.020 in. and a height of about 0.040 in.). A person skilled in the art will appreciate that for measurement values mentioned herein, the measurement value may not be precisely at a value (e.g., precisely at 0.035 in.) but nevertheless be considered to be at about that value due to one or more factors such as manufacturing tolerances and/or tolerances in measurement devices. The holes can each have a suture extending therethrough, as discussed further below, that in an exemplary embodiment has a diameter of up to about 0.020 in., e.g., in a range of about 0.018 to 0.025 in., which facilitates free sliding of the suture(s) through the holes after deployment of the implant and suture(s) into a patient's body, e.g., following deployment of the implant and suture(s) from a deployment device such as a delivery needle.

Figure 2:
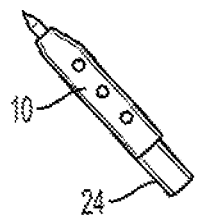
FIG. 2 is a perspective view of the implant of FIG. 1 coupled to a needle.
Figure 3:
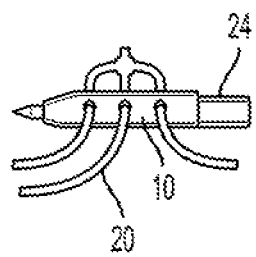
FIG. 3 is a perspective view of the implant and needle of FIG. 2 with the implant coupled to a suture.

FIGS. 1-3 illustrate one embodiment of an implant 10 configured to be implanted in a body of a patient to facilitate meniscal repair. FIG. 1 shows the implant 10 as a standalone element. The implant 10 has an inner lumen 12 (also referred to herein as an "inner passageway") extending therethrough so as to be cannulated and have open proximal and distal ends 14, 16.

The implant 10 has a plurality of holes 18 (also referred to herein as "through holes") formed through a sidewall thereof and in communication with the implant's inner lumen 12. The holes 18 are each configured to receive a suture 20 therethrough. The holes 18 each have a circular shape, although the holes 18 can have another shape (e.g., ovular, triangular, D-shaped, etc.). The holes 18 each having a circular shape or an ovular shape helps prevent the hole's walls from tearing or snagging of the suture 20 extending therethrough.

The implant 10 in this illustrated embodiment has six holes 18 with three holes 18 on one side of the implant 10 and three holes 18 on an opposite side of the implant 10. In an exemplary embodiment, the implant 10 has at least four holes 18 formed through its sidewall with a same number of holes 18 formed on opposed sides of the implant 10. In other words, at least two of the holes 18 are on one side of the implant 10 and at least two other holes 18 are on an opposite side of the implant 10. The holes 18 on one side of the implant 10 are aligned with the holes 18 on the other side of the implant 10 to facilitate passage of a suture 20 through aligned holes 18, and hence also through the implant's internal cannulation between the aligned holes 18 positioned substantially perpendicular to a longitudinal axis of the implant 10, and to facilitate balanced positioning of the implant 10 against tissue in response to tensioning the suture(s) 20 attached thereto. A person skilled in the art will appreciate that the suture 20 may not extend precisely perpendicular to the implant's longitudinal axis but nevertheless be considered to be perpendicular to the longitudinal axis due to one or more factors such as manufacturing tolerances and/or tolerances in measurement devices.

The implant 10 is symmetrical, e.g., its longitudinal halves are mirror images of one another. The implant 10 has different cross-sectional shapes along its longitudinal length. The implant 10 has an irregular cross-sectional shape along a substantial longitudinal length thereof that extends distally from the implant's proximal end to an axial position that is distal of all the holes 18. The irregular cross-sectional shape has a curved or arced portion and a rectangular portion that defines a fin 22 along this length of the implant 10 having the irregular cross-sectional shape. The implant 10 has a circular cross-sectional shape from the axial position where the irregular cross-sectional shape ends to a distal end of the implant. The circular cross-sectional shape has a varying diameter due to the implant 10 having a tapered distal end. The tapered distal end may facilitate passage of the implant 10 through tissue with the implant's distal end leading the implant's advancement through the tissue. The tapering can be entirely distal to the implant's holes 18, which may facilitate the pinching of suture(s) 20 extending through the implant's holes 18 by a needle also coupled to the implant 10.

The implant 10 can be delivered into a body of a patient and deployed therein in a variety of ways. FIG. 2 shows the implant 10 coupled to a needle 24 (also referred to herein as a "delivery needle," "stylette," and a "delivery tool") configured to deliver the implant 10 into a body of a patient and to deploy the implant 10 therein. The needle 24 extends coaxially through the implant 10 with a distal portion extending distally beyond the implant 10 and a proximal portion extending proximally beyond the implant. The needle 24 is a flexible needle, as will be discussed further below. As also discussed further below, the needle 24 pinches the suture(s) 20 extending through the implant's holes 18 against the sidewall of the implant 10 in a press fit that still allows deployment of the implant 10, with the suture(s) 20 attached thereto, from the needle 24. In an exemplary embodiment, the needle 24 is not cannulated.

FIG. 3 shows the implant 10 coupled to the needle 24 and to a suture 20 including a sliding knot. Each of the implant's through holes 18 has the suture 20 passed therethrough. One suture is shown coupled to the implant 10 and needle 24 in this illustrated embodiment, but a different number of sutures (e.g., two, three, four, etc.) can be coupled to the implant 10 and needle 24. As discussed further below, suture(s) coupled to an implant can be attached together in a variety of ways, such as via one or more knots or using one or more finger traps. As also discussed further below, the needle 24 is configured to deploy therefrom the implant 10 and the sutures 20.

Figure 4:
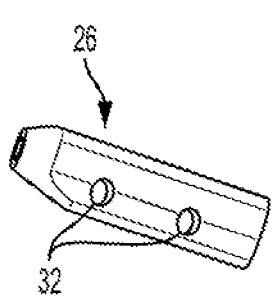
FIG. 4 is a perspective view of another embodiment of an implant.
Figure 5:
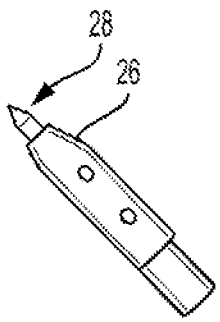
FIG. 5 is a perspective view of the implant of FIG. 5 coupled to a needle.
Figure 6:
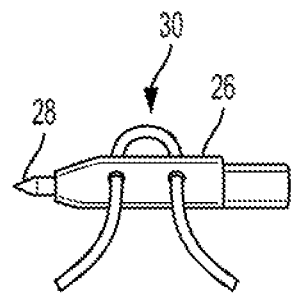
FIG. 6 is a perspective view of the implant and needle of FIG. 5 with the implant coupled to a suture.

FIGS. 4-6 illustrate another embodiment of an implant 26 configured to be implanted in a body of a patient to facilitate meniscal repair. FIG. 4 shows the implant 26 as a standalone element, FIG. 5 shows the implant 26 coupled to a needle 28 configured to deliver the implant 26 into a body of a patient and to deploy the implant 26 therein, and FIG. 6 shows the implant 26 coupled to the needle 28 and to a single suture 30. The implant 26 is similar to the implant 10 of FIGS. 1-3 except it has four holes 32 through its sidewall, two holes 32 on either side of the implant 26. The needle 28 is the same in FIGS. 2-3 and 5-6.

Figure 7:
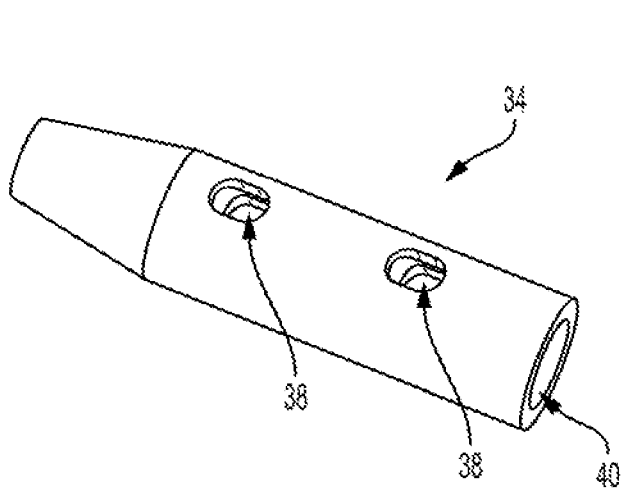
FIG. 7 is a perspective view of yet another embodiment of an implant.
Figure 7A:
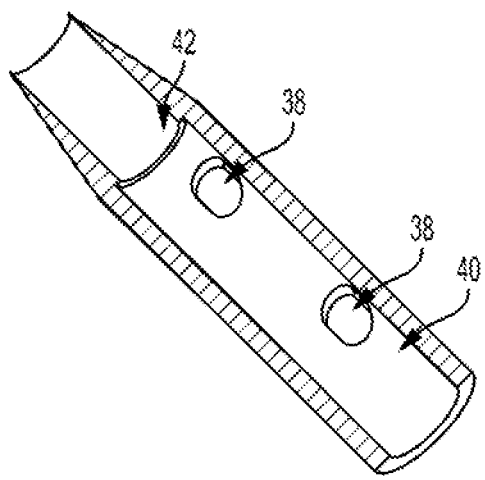
FIG. 7A is a cross-sectional view of the implant of FIG. 7.
Figure 8:
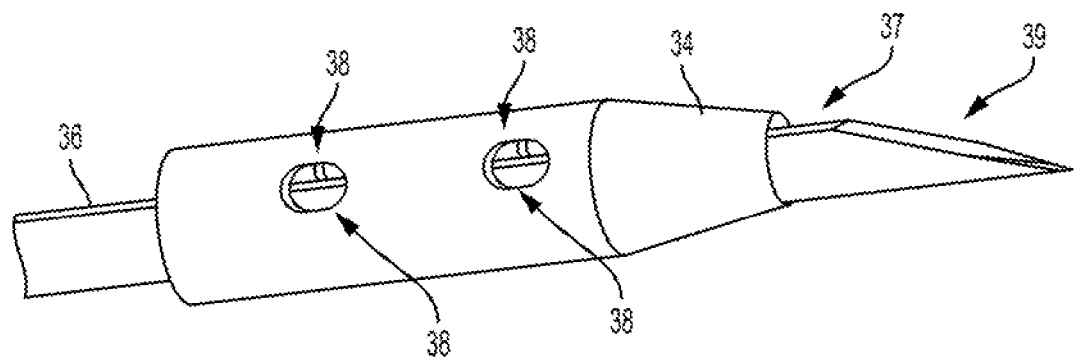
FIG. 8 is a perspective view of the implant of FIG. 7 coupled to a needle.
Figure 8A:
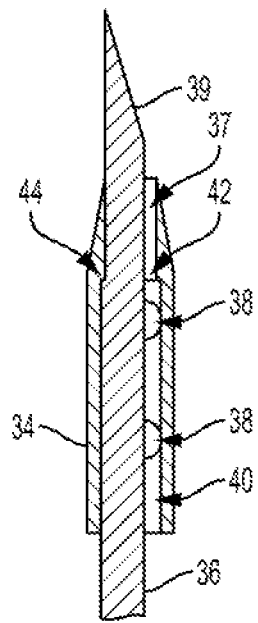
FIG. 8A is a side cross-sectional view of the implant and needle of FIG. 8.

FIGS. 7-8A illustrate another embodiment of an implant 34 configured to be implanted in a body of a patient to facilitate meniscal repair. FIGS. 7 and 7A show the implant 34 as a standalone element, and FIGS. 8 and 8A show the implant 34 coupled to a needle 36 configured to deliver the implant 34 into a body of a patient and to deploy the implant 34 therein. The implant 34 is similar to the implant 10 of FIGS. 1-3 except it (a) has four holes 38 through its sidewall, two holes 38 on either side of the implant 34, (b) the holes 38 each have an ovular or oblong shape instead of a circular shape, and (c) it has a circular cross-sectional shape along its entire longitudinal length. The holes 38 each having an elongated oblong shape may help reduce implant 34 disruption.

Figure 9A:
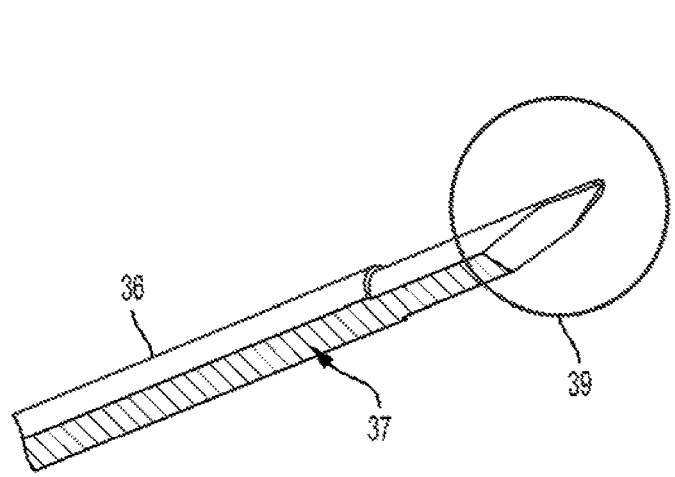
FIG. 9A is a perspective view of a distal portion of the needle of FIG. 8.
Figure 26:
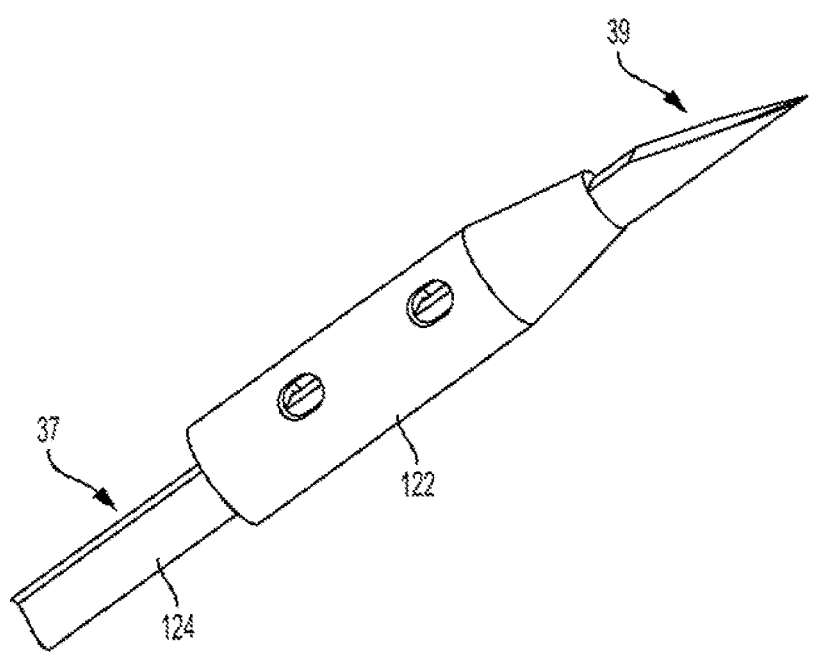
FIG. 26 is a perspective view of another embodiment of an implant coupled to a needle.

An inner lumen 40 of the implant 34 of FIG. 7 has a circular cross-sectional shape but can have another cross-sectional shape, such as a D-shaped cross-section (see, e.g., FIG. 26). As shown in the cross-sectional views of FIGS. 7A and 8A, the inner lumen 40 of the implant 34 has a constant first diameter in the proximal non-tapering portion of the implant 34 and a constant second diameter in the tapering distal portion of the implant 34, where the second diameter is less than the first diameter. The smaller distal diameter of the lumen 40 allows a stop surface 42 to be formed in the implant at a junction of the first and second diameters. The stop surface 42 extends circumferentially. The stop surface 42 is configured to abut a corresponding stop surface 44 of the needle 36, as shown in FIG. 8A. The needle 36 is also shown in FIG. 9A. The implant's stop surface 42 is a proximal-facing surface that engages the needle's stop surface 44, which is a distal-facing surface. The engaged stop surfaces 42, 44 may facilitate deployment of the implant 34 from the needle 36, as discussed further below.

Figure 10A:
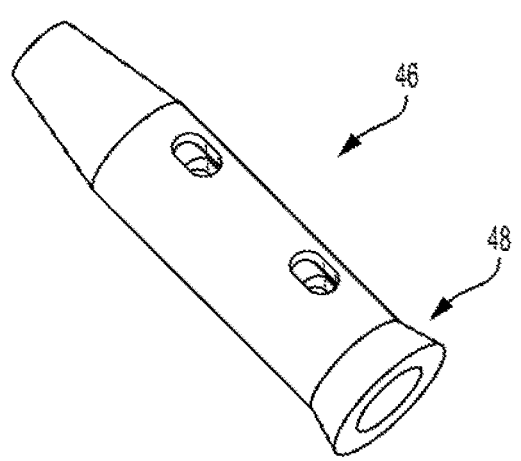
FIG. 10A is a perspective view of another embodiment of an implant.

FIG. 10A illustrates another embodiment of an implant 46 configured to be implanted in a body of a patient to facilitate meniscal repair. The implant 46 is similar to the implant 34 of FIGS. 7-8A except it includes a retention feature 48 at its proximal end. The retention feature 48 is configured to help retain the implant 46 on the side of the meniscus on which it is deployed, e.g., to prevent the implant 46 from backing out through the meniscus when the needle is backed out after deploying the implant 46. The retention feature in this illustrated embodiment is a flared proximal end such that the implant has a proximal end that tapers radially outward, unlike its distal end that tapers radially inward. The exemplary implant outer diameter above of about 0.052 in. is without the flared proximal end. The retention feature 48 may facilitate toggling of the implant 46 against tissue by helping to locate the toggled implant 46 appropriately against the surface of the tissue.

Figure 10B:
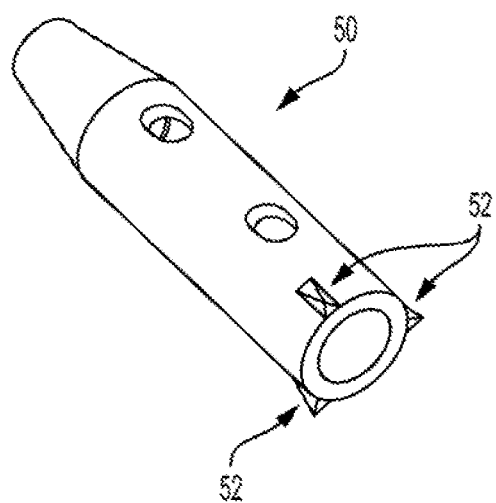
FIG. 10B is a perspective view of still another embodiment of an implant.

FIG. 10B illustrates another embodiment of an implant 50 configured to be implanted in a body of a patient to facilitate meniscal repair. The implant 50 is similar to the implant 46 of FIG. 10A except its retention feature 52 at a proximal end thereof is in the form of a plurality of barbs that extend radially outward. The implant 50 includes three barbs, but an implant can include another number of barbs. In an exemplary embodiment, the implant 50 includes a plurality of barbs spaced equidistantly around the implant's perimeter, which may facilitate balanced retention of the implant. The exemplary implant outer diameter above of about 0.052 in. is without the plurality of barbs.

Figure 11:
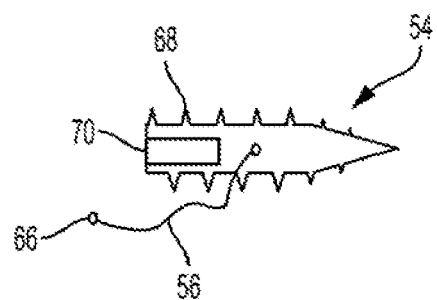
FIG. 11 is a side cross-sectional schematic view of another embodiment of an implant coupled to a suture including a noose.
Figure 12:
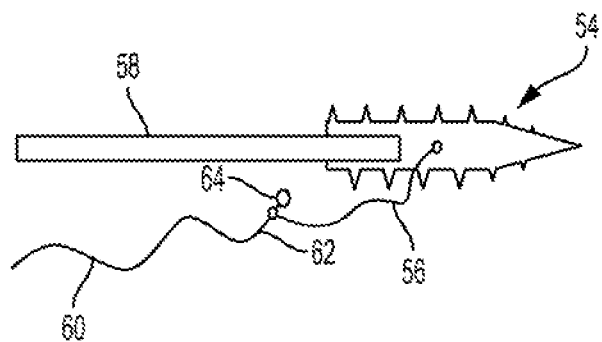
FIG. 12 is a side cross-sectional schematic view of the implant of FIG. 11 coupled to a driver and the suture of FIG. 11 coupled to another suture.

FIGS. 11-12 illustrate another embodiment of an implant 54 configured to be implanted in a body of a patient to facilitate meniscal repair. FIG. 11 shows (in cross-section) the implant 54 coupled to a suture 56 (also referred to herein as a "coupling filament"), and FIG. 12 shows (in cross-section) the implant 54 and the suture 56 coupled to a driver 58 configured to deliver the implant 54 into a body of a patient and to deploy the implant 54 therein. The suture 56 can be attached to the implant 54 in any of a variety of ways, as will be appreciated by a person skilled in the art, such as by being crimped thereon, attached thereto with adhesive, tied thereto, etc. FIG. 12 also shows a second suture 60 coupled to the suture 56, with the two sutures 56, 60 attached together via a swivel coupling 62. The second suture 60 includes a stopper knot 64 to facilitate coupling of the sutures 56, 60 at the swivel coupling 62 by coupling to a noose 66 (also referred to herein as a "swivel loop") of the suture 56 configured to cinch around the second suture 60. The swivel coupling 62 is configured to allow the driver 58 to rotate and thereby rotate the implant 54 coupled thereto without rotating the collapsible suture bridge 60 but instead only rotating the suture 56 attached to the implant 54 distal to the swivel coupling 62. In this way, another implant coupled to the collapsible suture bridge 60 will not rotate in response to the driver 58 being rotated to drive the implant 54 through tissue.

The implant 54 includes a thread 68 that spirals around an exterior surface thereof. The thread 68 may facilitate passage of the implant 54 through tissue by allowing the implant 54 to be self-propelling.

The implant 54 has a closed distal end such that the implant 54 is not cannulated. The distal end tapers distally, which may facilitate passage of the implant 54 through tissue. The distal tip of the implant is pointed, which may allow the implant 54 to puncture an opening in tissue through which the implant 54 may pass through manipulation of the driver 58 coupled thereto.

The implant 54 has a proximal drive feature 70 configured to releasably mate with a driver such as the illustrated driver 58. The drive feature 70 includes a bore formed in a proximal end of the implant 54 configured to receive a distal end of the driver 58 therein. The bore has a shape that matches the shape of the driver's distal end, which in this illustrated embodiment is a hex shape but that can be other shapes.

Figure 13:
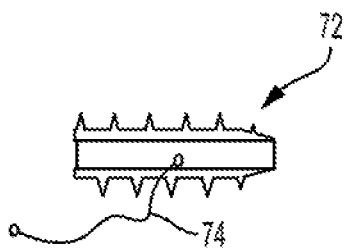
FIG. 13 is a side cross-sectional schematic view of yet another embodiment of an implant coupled to a suture including a noose.
Figure 14:
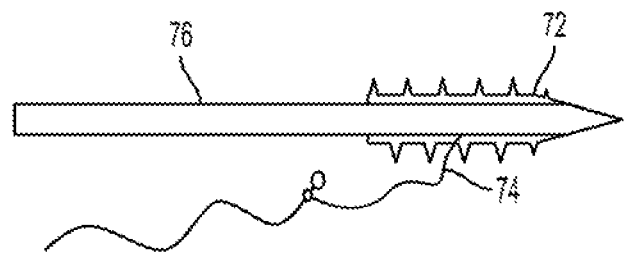
FIG. 14 is a side cross-sectional schematic view of the implant of FIG. 13 coupled to a driver and the suture of FIG. 13 coupled to another suture.

FIGS. 13-14 illustrate another embodiment of an implant 72 configured to be implanted in a body of a patient to facilitate meniscal repair. FIG. 13 shows (in cross-section) the implant 72 coupled to a suture 74, and FIG. 14 shows (in cross-section) the implant 72 and the suture 74 coupled to a driver 76 configured to deliver the implant 72 into a body of a patient and to deploy the implant 72 therein. The implant 72 is similar to the implant 54 of FIGS. 11-12 except it is cannulated.

Figure 15:
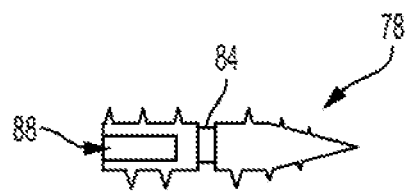
FIG. 15 is a side cross-sectional schematic view of another embodiment of an implant.
Figure 16:
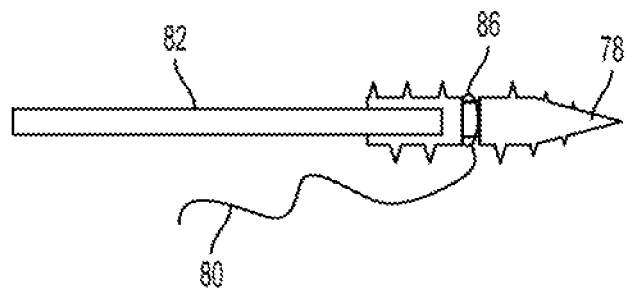
FIG. 16 is a side cross-sectional schematic view of the implant of FIG. 15 coupled to a driver and a suture.

FIGS. 15-16 illustrate another embodiment of an implant 78 configured to be implanted in a body of a patient to facilitate meniscal repair. FIG. 15 shows (in cross-section) the implant 78 as a standalone element, and FIG. 16 shows (in cross-section) the implant 78 and coupled to a suture 80 and to a driver 82 configured to deliver the implant 78 into a body of a patient and to deploy the implant 78 therein. The implant 78 is similar to the implant 54 of FIGS. 11-12 except it includes a suture mating feature 84 in the form of a groove extending circumferentially therearound. The groove 84 can be configured to seat a suture therein, as shown in FIG. 12 in which a suture loop 86 of the suture 80 is seated therein. The suture 80 is in the form of a collapsible suture configured to be collapsed so as to cinch the suture loop 86 around the implant 78 within the groove 84. The groove 84 is located distal to the bore 88 formed in the implant 78 that mates with a driver, which may allow the suture 80 to be cinched around a solid portion of the implant 78 and thereby be cinched around a more structurally stable portion of the implant 78 than the hollowed portion of the implant 78 that includes the bore 88. The groove 84 is configured to allow the driver 82 to rotate and thereby rotate the implant 78 coupled thereto without rotating the collapsible suture bridge 80 but instead only rotating the implant 78 within the noose 86 seated in the groove 54. In this way, another implant coupled to the collapsible suture bridge 80 will not rotate in response to the driver 82 being rotated to drive the implant 78 through tissue.

Figure 17:
FIG. 17 is a side cross-sectional schematic view of still another embodiment of an implant.
Figure 18:
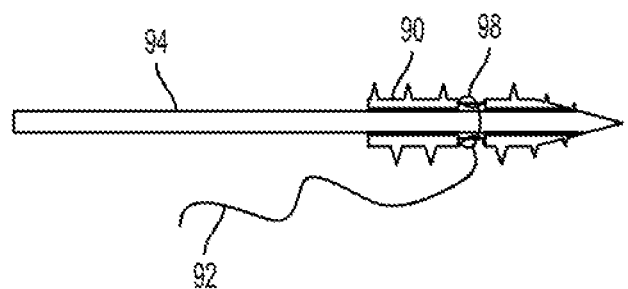
FIG. 18 is a side cross-sectional schematic view of the implant of FIG. 17 coupled to a driver and a suture.

FIGS. 17-18 illustrate another embodiment of an implant 90 configured to be implanted in a body of a patient to facilitate meniscal repair. FIG. 17 shows (in cross-section) the implant 90 as a standalone element, and FIG. 18 shows (in cross-section) the implant 90 and coupled to a suture 92 and to a driver 94 configured to deliver the implant 90 into a body of a patient and to deploy the implant 90 therein. The implant 90 is similar to the implant 72 of FIGS. 13-14 except it includes a suture mating feature 96 in the form of a soft coupling extending circumferentially therearound. The soft coupling 96 is configured to allow the driver 94 to rotate and thereby rotate the implant 90 coupled thereto without rotating the collapsible suture bridge 92 but instead only rotating the implant 90 within the noose 98 seated in the soft coupling 96. In this way, another implant coupled to the collapsible suture bridge 92 will not rotate in response to the driver 94 being rotated to drive the implant 90 through tissue.

The soft coupling 96 can be configured to seat a suture, as shown in FIG. 18 in which a suture loop 98 of the suture 92 is seated by the soft coupling 96 by being tied therearound. The suture 92 is in the form of a collapsible suture configured to be collapsed so as to cinch the suture loop 98 around the implant 90 and collapse the soft coupling 96 to a smaller diameter than rigid portions of the implant 90 on either side of the soft coupling 96. The suture 92 can be coupled to the soft coupling 96 after the driver 94 has been advanced through the inner lumen thereof at least so the driver 94 extends within the implant 90 throughout a longitudinal length of the soft coupling 96. In this way, the suture 92 will not be cinched too tightly to allow passage of the driver 94 through the implant 90. The soft coupling 96 can have a variety of configurations, such as a plurality of sutures extending between the proximal and distal rigid portions of the implant, a ring of material (e.g., fabric, a biocompatible polymer, etc.) attaching together the proximal and distal rigid portions of the implant 90 and configured to flex radially inward in response to tension of the suture 92 therearound, a plurality of fabric strips extending between the proximal and distal rigid portions of the implant 90, etc.

Figure 19:
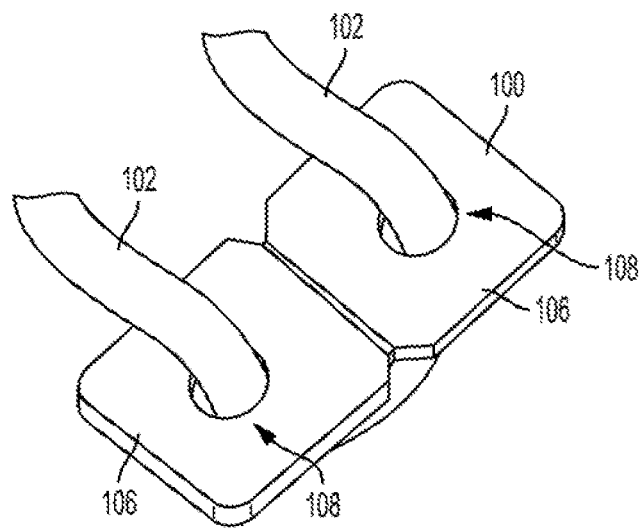
FIG. 19 is a perspective view of another embodiment of an implant coupled to a suture, the implant being in a deployed orientation.
Figure 20:
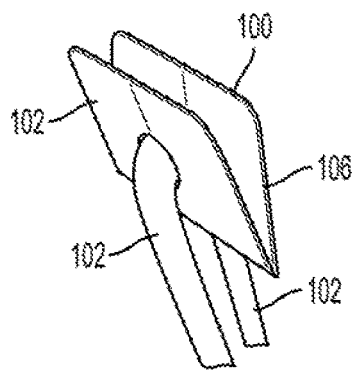
FIG. 20 is a perspective view of the implant and suture of FIG. 19, the implant being in a delivery orientation.
Figure 21:
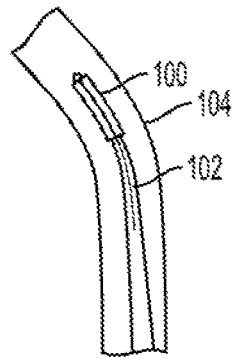
FIG. 21 is a perspective, partially transparent view of the implant and suture of FIG. 20 coupled to a needle.

FIGS. 19-21 illustrate another embodiment of an implant 100 configured to be implanted in a body of a patient to facilitate meniscal repair. FIGS. 19-20 show the implant 100 coupled to a suture 102, and FIG. 21 shows the implant 100 coupled to the suture 102 and to a needle 104 configured to deliver the implant 100 into a body of a patient and to deploy the implant 100 therein.

The implant 100 is configured to move from a delivery orientation (shown in FIGS. 20-21), in which the implant 100 is configured to be delivered into a body of a patient, to a deployed orientation (shown in FIG. 19), in which the implant 100 is configured to be implanted at a desired position within the patient's body. The implant 100 has a fold zone (e.g., a scored area, a weakened area, an area more flexible than wings 106 of the implant 100 on either size thereof, etc.) in a mid-portion thereof at which the implant 100 is configured to fold. The implant 100 in the delivery orientation is folded at the fold zone, and the implant 100 in the deployed configuration is not folded at the fold.

The implant 100 has a plurality of holes 108 formed therethrough. The holes 108 are each configured to receive a suture therethrough. The holes 108 each have a circular shape, although the holes 108 can have another shape (e.g., ovular, triangular, etc.), similar to that discussed above regarding the implant 10 of FIG. 1. The implant 100 in this illustrated embodiment has one hole 108 through one wing 106 of the implant 100 and one hole 108 through the other wing 106 of the implant 100, but each wing 106 can have another number of holes 108 same as one another. The holes 108 on one wing 106 of the implant 100 are aligned with the holes 108 on the other wing 106 of the implant 100 when the implant 100 is in the delivery orientation to facilitate passage of a suture through aligned holes 108 and to facilitate balanced positioning of the implant 100 against tissue in response to tensioning the suture(s) attached thereto.

Only one suture 102 is shown coupled to the implant 100 in this illustrated embodiment, but a plurality of sutures can be coupled to the implant 100, e.g., a plurality of sutures passing through a hole 108, a plurality of holes 108 each having one suture passing therethrough, or both.

The implant 100 can be soaked in a biological substance, such as blood, platelet-rich plasma (PRP), or cytokines.

Figure 22:
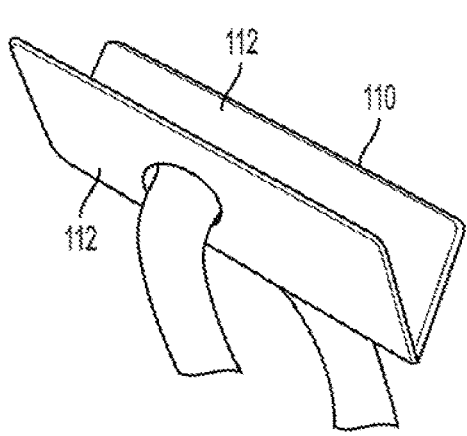
FIG. 22 is a perspective view of still another embodiment of an implant coupled to a suture, the implant being in a deployed orientation.

FIG. 22 illustrates another embodiment of an implant 110 configured to be implanted in a body of a patient to facilitate meniscal repair. The implant 110 is similar to the implant 100 of FIGS. 19-21 except instead of having square-shaped wings to form a square-shaped folded implant, its wings 112 on either size of its fold zone each have a rectangular shape such that when the implant 110 is folded, the implant 110 has a rectangular shape.

Figure 23:
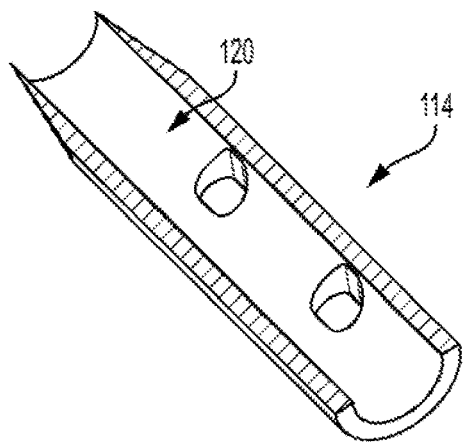
FIG. 23 is a perspective cross-sectional view of another embodiment of an implant.
Figure 24:
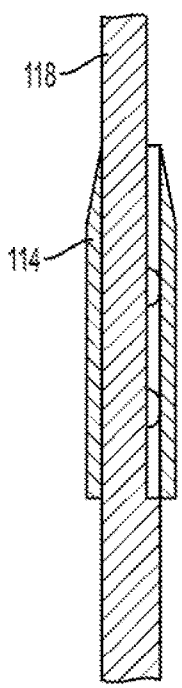
FIG. 24 is a side cross-sectional view of the implant of FIG. 23 coupled to a needle.
Figure 25:
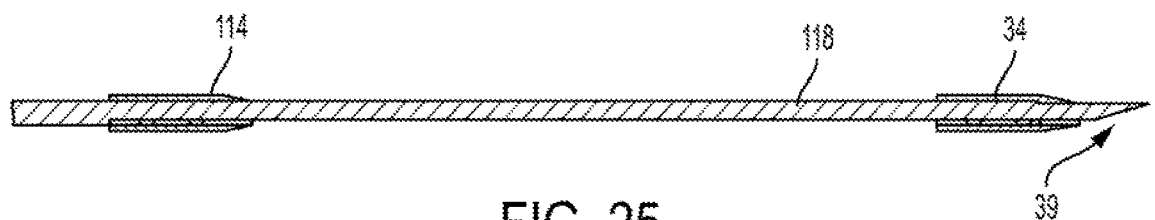
FIG. 25 is a side cross-sectional view of the implant of FIG. 23 and the implant of FIG. 7 coupled to a needle.

FIGS. 23-25 illustrate another embodiment of an implant 114 configured to be implanted in a body of a patient to facilitate meniscal repair. FIG. 23 shows (in cross-section) the implant 114 as a standalone element, and FIGS. 24-25 show (in cross-section) the implant 114 coupled to a needle 118 configured to deliver the implant 114 into a body of a patient and to deploy the implant 114 therein. FIG. 25 also shows the implant 34 of FIG. 7 coupled to the needle 118, with the implant 114 of FIG. 23 on a left side of the needle 116 as viewed in FIG. 25 and the implant 34 of FIG. 7 on a right side of the needle 116 as viewed in FIG. 25. The implant 114 of FIG. 23 is similar to the implant 34 of FIG. 7, except its inner lumen 120 has a constant diameter along its length. The implant 114 of FIG. 23 thus does not have a stop surface, unlike the implant 34 of FIG. 7.

FIGS. 26-28 illustrate another embodiment of an implant 122 configured to be implanted in a body of a patient to facilitate meniscal repair. FIG. 26 shows the implant 122 coupled to a needle 124 configured to deliver the implant into a body of a patient and to deploy the implant 122 therein, and FIGS. 27-28 show (FIG. 28 in cross-section) the implant 120 as a standalone element. The needle 124 of FIG. 26 is the same as the needle 116 of FIGS. 24-25. The implant 122 of FIG. 26 is similar to the implant 34 of FIG. 7, except its inner lumen 126, instead of having a circular cross-sectional shape, has a D-shaped cross-section. The D-shaped cross-section allows more material to form the implant 122, e.g., less of the implant 122 is hollow than the implant 34 of FIG. 7, which may make the implant 122 stronger, e.g., more structurally stable, and thus less likely to break during deployment or after implantation. In other words, an implant having an outer diameter and having an inner lumen having a D-shaped cross section will be made of more material than another implant having that same outer diameter but having a circular cross-sectional shape. The D-shaped cross-section allows a distal tip (e.g., a beveled end or sharp tip) of a stylette to be broader than would be advanceable through another shaped cross-section of the implant's inner lumen, such as a circular shape. The broader distal tip may reduce dag on the implant as the stylette advances the implant through tissue.

Sutures

Meniscus repair typically uses a plurality of implants attached together via one or more sutures. The suture(s) can be attached to the implants in a variety of ways. Various techniques of attaching a suture to a plurality of implants are discussed below. The suture(s) can have any of a variety of sizes, such as a size in a range of about size #0 to #2-0.

Following delivery of the implants into a body of a patient, the suture(s) attached to the implants are tensioned to secure the implants in position. The sutures being able to slide relative to the implants after the delivery of the implants into the patient's body thus facilitates the tensioning of the sutures and hence facilitates secure positioning of the implants within the patient's body to help facilitate proper healing.

One technique for attaching a suture to a plurality of implants uses a collapsible suture, such as the technique used in the OMNISPAN™ Surgical Repair System (Depuy Mitek, Inc. of Raynham, Mass.). FIG. 29 illustrates one embodiment of such an OMNISPAN™ style technique. FIG. 29 shows the implant 10 of FIG. 1 on the right and the implant 26 of FIG. 4 on the left. A collapsible suture 128 that includes a sliding knot is passed through the holes 18 of the implant 10 of FIG. 1 on the right, and a suture loop having the suture 128 looped therethrough is passed through the holes 32 of the implant 26 of FIG. 4 on the left.

Another technique for attaching a suture to a plurality of implants uses a plurality of finger traps. FIG. 30 illustrates one embodiment of such a technique. The technique of FIG. 30 is illustrated using two implants 26 of FIG. 4 but can be similarly used with other embodiments of implants. The implants used with a plurality of finger traps only need four holes (two each on opposite sides thereof) but can have more holes, e.g., to facilitate manufacturing and/or to facilitate use of the implants with different suture techniques.

A single suture 130 is coupled to each of the implants 26, with the suture 130 including a number of finger traps 132 equal to the number of implants 26, which in this illustrated embodiment is two. In general, each of the finger traps 132 is an area of the suture 130 that is hollow and through which the suture 130 passes through itself, is slidable uni-directionally, and is locked from sliding in the other direction. Using a single suture 130 that is looped through each of the implants 26 may facilitate advancement of the implants 26 and the suture 130 into a patient's body by taking up less space than multiple sutures, may be less likely to tear meniscus because less material need be passed therethrough than if multiple sutures were used, and/or may make the suture 130 less likely to snag on an instrument and/or other matter than if multiple sutures were used, as each of the sutures could potentially snag on matter.

After the implants 26 are advanced through the meniscus (or other tissue with which they are being used), the suture 130 is tensioned by pulling on each of the suture's two tails 134, thereby sliding the suture 130 through the finger traps 132. The suture tails 134 can be independently pulled so as to independently secure each of the implants 26, which may help ensure that each of the implants 26 is appropriately positioned via the tension since each implant 26 may be more desirably positioned with different tensions applied to the different suture tails. The suture tails 134 can, however, be pulled together if so desired. The suture 130 being pulled through a finger trap 132 allows the suture 130 to simply slide longitudinally along itself in the area of the finger trap 132, which exerts less stress on the suture 130 than the suture 130 being pulled through a tortuous path, such as when a knot is used instead of a finger trap.

After the suture 130 is tensioned, the tails 134 can be trimmed to allow removal of excess material from the patient's body. The tails 134 can be trimmed after the suture 130 is pulled through all of the finger traps 132 or can be trimmed for any individual finger trap 132 after the suture tail 134 associated with that finger trap 132 has been pulled. Each tail 134 is trimmed as close as possible to the finger trap 132. Thus, a minimal amount, if any, suture tail will remain present in the body and thereby minimize damage to cartilage adjacent thereto by rubbing thereagainst during post-surgery movement of the patient since the tail will be minimally present, if present at all, unlike sutures secured with knots that need some tail present when the suture is trimmed to help prevent the knot from unraveling post-surgery.

FIG. 31 illustrates another embodiment of a technique for attaching a suture to a plurality of implants uses a plurality of finger traps. The technique of FIG. 31 is illustrated using four implants 26 of FIG. 4 but can be similarly used with other embodiments of implants. The technique of FIG. 31 uses two sets of the construct of FIG. 30, e.g., a first set of two implants 26 and two finger traps 136 and a suture 138 and a second set of two implants 26 and two finger traps 136 for a total of four implants 26 and four finger traps 136. The two sutures 138 are tied or otherwise secured together between the four finger traps 136 to secure the four implants 26 together.

FIG. 32 illustrates another embodiment of a technique for attaching a suture to a plurality of implants uses a plurality of finger traps. The technique of FIG. 32 is illustrated using two implants 26 of FIG. 4 but can be similarly used with other embodiments of implants. The technique of FIG. 32 is similar to the construct of FIG. 30 but includes a protective member 140 (e.g., a patch, tape, etc.) on the suture 142 between the two finger traps 144. The protective member 140 can be attached to the suture 142 in any of a variety of ways, such as by having the suture 142 sewn thereto, tied thereto, adhered thereto with adhesive, etc. The protective member 140 is configured to abut a surface of the meniscus (or other tissue with which the implants 26 are used) after the suture 142 is tensioned, thereby helping to prevent the suture 142 extending along that surface from causing damage to the meniscus (or other tissue) by rubbing thereagainst and/or cheese-wiring therethrough. The suture 142 can be embedded within the protective member 140 so as to not contact the meniscus (or other tissue) therealong, can be partially embedded within the protective member 140 so as to contact the meniscus (or other tissue) therealong less than if the protective member 140 was not present, can extend along the protective member 140 on an opposite side thereof than abuts the meniscus/tissue surface so as to not contact the meniscus (or other tissue) therealong, or can extend along the protective member 140 on the same side thereof that abuts the meniscus/tissue surface so as to contact the meniscus (or other tissue) therealong but be less likely to cut into or otherwise damage the meniscus/tissue. The protective member 140 has a rectangular shape in this illustrated embodiment but can have other shapes.

FIG. 33 illustrates another embodiment of a technique for attaching a suture to a plurality of implants uses a plurality of finger traps. The technique of FIG. 33 is illustrated using four implants 26 of FIG. 4 but can be similarly used with other embodiments of implants. The technique of FIG. 33 is similar to the construct of FIG. 31 but includes a protective member 146 (e.g., a patch, tape, etc.) on the suture 148 between the four finger traps 150. The protective member 146 is similar to the protective member 140 of FIG. 32. The protective member 140 has a square shape in this illustrated embodiment but can have other shapes. The protective member 146 can be biologically active.

Another technique for attaching a suture to a plurality of implants uses a suture loop. A first suture in the form of a loop extends through holes formed through a first implant's sidewall, and a second suture in the form of a strand is coupled to the loop and extends to a second implant, e.g., to a third suture in the form of a loop extending through holes formed through the second implant's sidewall. The second suture is configured to be pulled to toggle the implant against tissue, as discussed herein. The second suture is configured to slide around the first suture loop and around the third suture loop, which may reduce friction of the second suture against the implant when the second suture is pulled to toggle the implant since the second suture is not being pulled through the holes formed in the implant.

Figure 34:
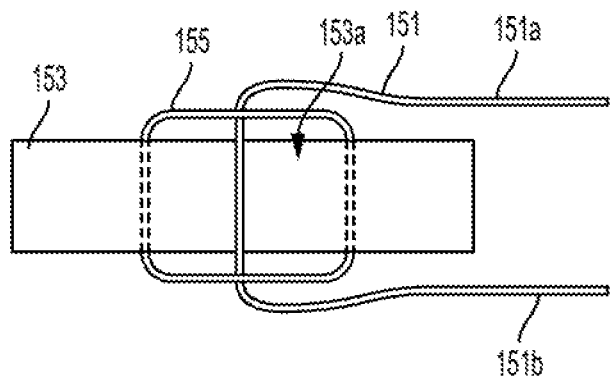
FIG. 34 is a top schematic view of one embodiment of a suture and a suture loop coupled to an implant.
Figure 35:
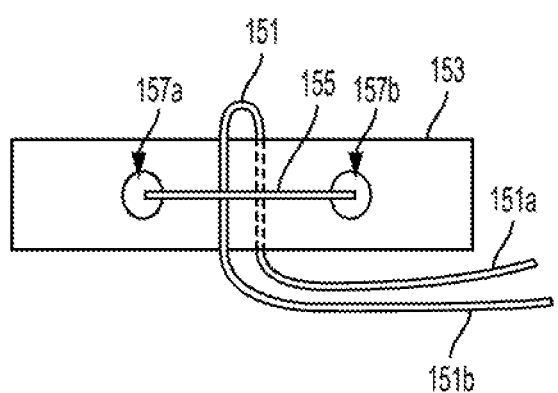
FIG. 35 is a side schematic view of the implant, suture, and suture loop of FIG. 34.
Figure 36:
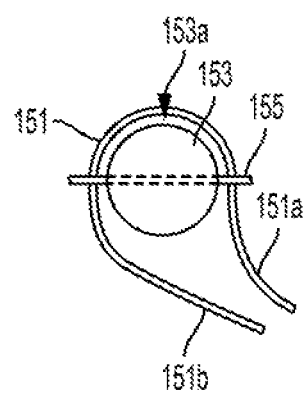
FIG. 36 is an end schematic view of the implant, suture, and suture loop of FIG. 34.

FIGS. 34-36 illustrate one embodiment of a technique for attaching a suture 151 to an implant 153 using a suture loop 155 that extends through holes 157*a*, 157*b* extending through a sidewall of the implant 153. Trailing ends 151*a*, 151*b* of the suture 151 trail away from the implant 153 in a direction opposite to a side 153a of the implant 153 along which the suture 151 extends around a partial outer perimeter of the implant 153.

Figure 37:
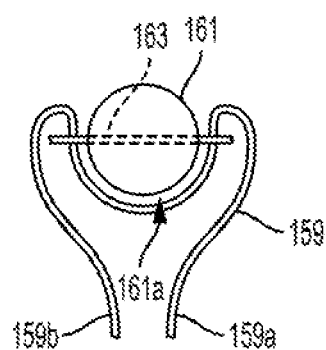
FIG. 37 is an end schematic view of another embodiment of a suture and a suture loop coupled to an implant.

FIG. 37 illustrates another embodiment of a technique for attaching a suture 159 to an implant 161 using a suture loop 163 that extends through holes extending through a sidewall of the implant 161. Trailing ends 159a, 159b of the suture 159 trail away from the implant 161 in a direction toward a side 161a of the implant 161 along which the suture 159 extends around a partial outer perimeter of the implant 161.

Figure 38:
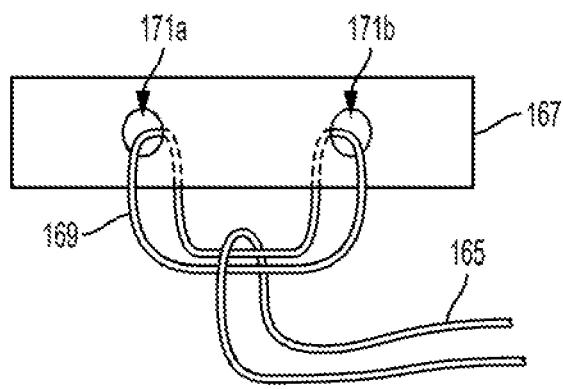
FIG. 38 is a side schematic view of yet another embodiment of a suture and a suture loop coupled to an implant.

FIG. 38 illustrates another embodiment of a technique for attaching a suture 165 to an implant 167 using a suture loop 169 that extends through holes 171a, 171b extending through a sidewall of the implant 167. The suture 165 is configured to not slide against any surface of the implant 167 when the suture 165 is pulled to toggle the implant 167 against tissue such that no friction exists between the suture 165 and the implant 167 during the pulling that may damage the suture 165 and/or the implant 167.

Figure 39:
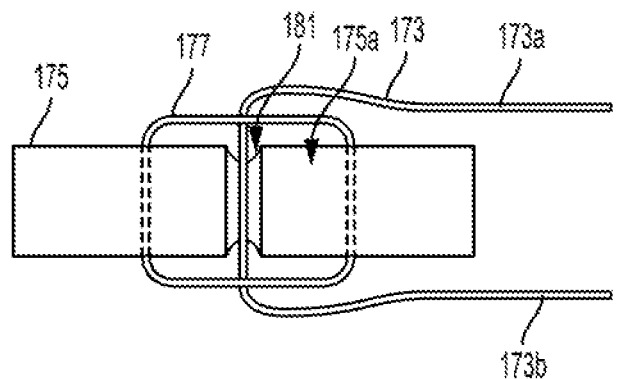
FIG. 39 is a top schematic view of still another embodiment of a suture and a suture loop coupled to an implant.
Figure 40:
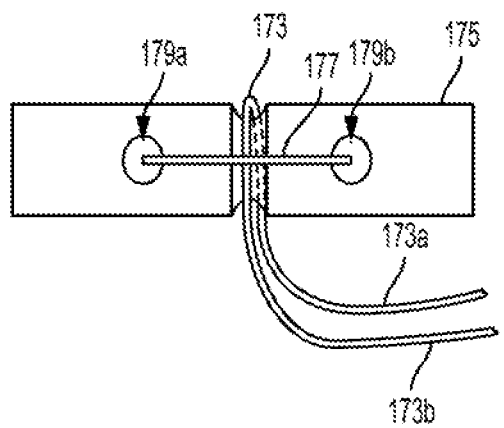
FIG. 40 is a side schematic view of the implant, suture, and suture loop of FIG. 39.
Figure 41:
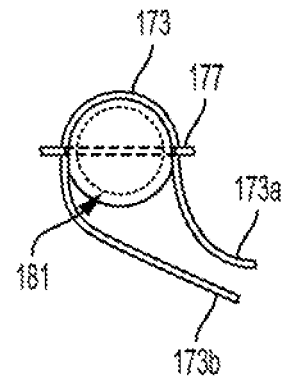
FIG. 41 is an end schematic view of the implant, suture, and suture loop of FIG. 39.

FIGS. 39-41 illustrate another embodiment of a technique for attaching a suture 173 to an implant 175 using a suture loop 177 that extends through holes 179a, 179ab extending through a sidewall of the implant 175. This embodiment is similar to the embodiments of FIGS. 34-36 in that trailing ends 173a, 173b of the suture 173 trail away from the implant 175 in a direction opposite to a side 175a of the implant 175 along which the suture 173 extends around a partial outer perimeter of the implant 175. The implant 175 in this embodiment, however, has a groove 181 formed in an outer surface thereof that is configured to seat the suture 173 therein. The suture 173 is configured to slide within the groove 181 when the suture 173 is pulled to toggle the implant 167, which may provide a smooth and predictable surface against which the suture 173 may slide while the suture 173 is being pulled, thereby reducing chances of the suture 173 and/or the implant 175 being damaged during the suture pulling. The groove 181 extends circumferentially around an entire perimeter of the implant 175, which may allow the suture 173 to be seated in the groove 181 regardless of a direction the suture's trailing ends 173a, 173b extend from the implant 175. The groove 181 can, however, extend around less than the entire perimeter of the implant 175.

Needles

The implants described herein can be advanced through tissue in any of a variety of ways. For example, the implants can be delivered to a surgical site using one or more needles. The one or more needles can be configured to cut tissue (e.g., meniscus) to facilitate passage of the implant(s) associated therewith through the tissue since the implants may not be configured to cut tissue. An implant not being configured to cut tissue (e.g., the implant lacks a cutting surface) may help reduce chances of the implant inadvertently damaging tissue and/or other matter within the patient's body post-surgery.

In some embodiments, each of a plurality of implants coupled together with one or more sutures can be coupled to its own needle configured to advance its associated implant through tissue (e.g., meniscus in a meniscal repair procedure) such that multiple needles are used to advance the implants through the tissue. Using multiple needles may require multiple incisions to be made in the patient, one incision for each needle, and may require an additional incision to facilitate the tying together of sutures threaded through tissue with the needles. In a meniscus repair procedure, needles may be inserted through the sides of the knee instead of through the back of the knee in order to avoid possible damage to vital structures including veins and nerves at the back of the knee. In meniscus repair, use of multiple needles is generally referred to as an inside-out surgical technique.

An embodiment of advancing any of the constructs of FIGS. 29-33 is illustrated in FIGS. 44-48 in which a plurality of flexible needles are used to advance the plurality of implants, with each of the needle associated with one of the implants, through meniscus tissue in a meniscus repair procedure, although the method of FIGS. 44-48 can be used in other types of surgical procedures.

Figure 44:
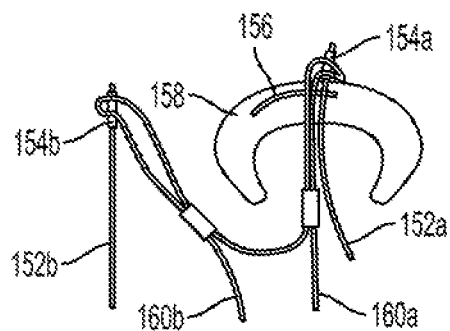
FIG. 44 is a schematic view of meniscus tissue with a first needle and a first implant advanced therethrough.
Figure 45:
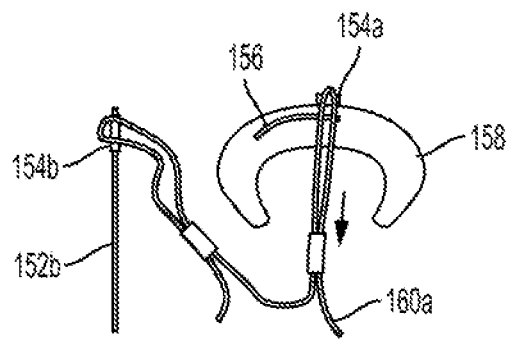
FIG. 45 is a schematic view of the meniscus tissue of FIG. 44 with the first needle withdrawn therefrom and the first implant being tensioned.
Figures 46, 47, 48:
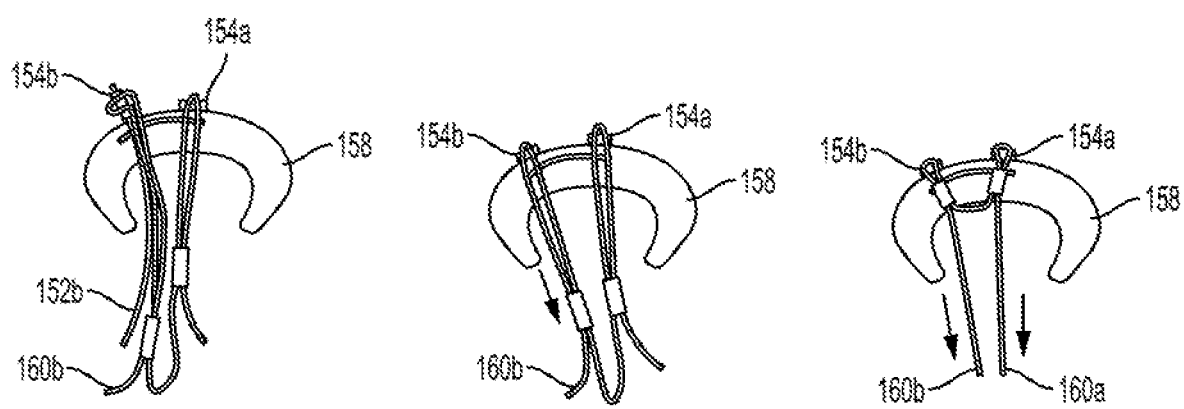
FIG. 46 is a schematic view of the meniscus tissue of FIG. 45 with a second needle and a second implant advanced therethrough.
FIG. 47 is a schematic view of the meniscus tissue of FIG. 46 with the second needle withdrawn therefrom and the second implant being tensioned.
FIG. 48 is a schematic view of the meniscus tissue of FIG. 46 with the first and second implants being tensioned.

FIG. 44 shows a first one of the needles 152a and its associated first implant 154a advanced through the meniscus on one side of a tear 156 in the meniscus 158. FIG. 45 shows the first needle 152a having been advanced back out of the meniscus and removed and the suture tail 160a associated with the first implant 154a being tensioned to toggle the first implant 154a into position against the meniscus 158. FIG. 46 shows a second one of the needles 152b and its associated second implant 154b advanced through the meniscus 158 on the other side of the tear 156 in the meniscus 158. FIG. 47 shows the second needle 152b having been advanced back out of the meniscus 158 and removed and the suture tail 160b associated with the second implant 154b being tensioned to toggle the second implant 154b into position against the meniscus 158. FIG. 48 shows the first and second suture tails 160a, 160b being tensioned to secure their associated first and second implants 154a, 154b in position against the meniscus 158 on either side of the tear 156. As shown in FIGS. 44-48, the needles 152a, 152b need not pass through skin to outside of the patient's body prior to the sutures being tensioned and the implants 154a, 154b secured in position against the meniscus 158.

Figure 42:
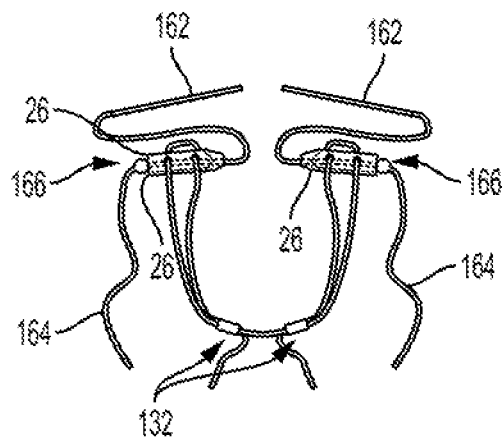
FIG. 42 is a side view of two implants of FIG. 30 each coupled to a needle and a suture shuttle including a protrusion.

FIG. 42 illustrates one embodiment of a construct for advancing a plurality of implants through tissue using a plurality of needles, each needle being flexible and being associated with one of the implants. The construct of FIG. 42 is illustrated using two implants 26 of FIG. 4 attached together using the technique of FIG. 30 that includes finger traps 132 but can be similarly used with other embodiments of implants and suture attachment techniques, such as the techniques of FIGS. 29 and 31-33.

In the construct of FIG. 42, each of the needles 162 has a suture shuttle 164 trailing distally therefrom, and the suture shuttle 164 includes a protrusion 166 (e.g., a knot, a bead, etc.) at a point along a length thereof. Each of the needles 162 is located distal to its associated implant 26 with the protrusion 166 of the associated suture 164 having a diameter greater than the diameter of the implant's inner lumen so as to act as a stop limiting distal advancement of the needle 162 relative to its associated implant 26. The protrusion 166 also helps ensure that the implant 26 associated therewith is pulled by the needle 162 when the needle 162 is advanced in a distal direction through tissue.

Figure 43:
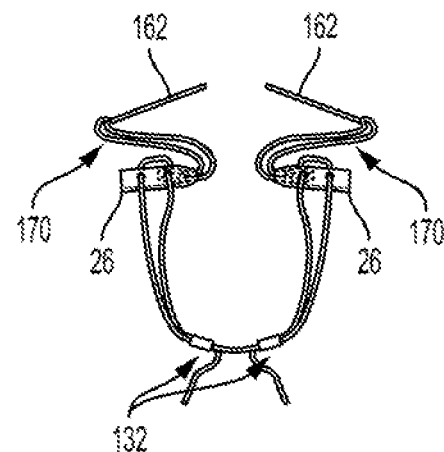
FIG. 43 is a side view of two implants of FIG. 30 each coupled to a needle and a suture shuttle.

FIG. 43 illustrates another embodiment of a construct for advancing a plurality of implants through tissue using a plurality of needles, each needle being flexible and being associated with one of the implants. The construct of FIG. 43 is illustrated using two implants 26a, 26b of FIG. 4 attached together using the technique of FIG. 30 that includes finger traps 132 but can be similarly used with other embodiments of implants and suture attachment techniques, such as the techniques of FIGS. 29 and 31-33. In the construct of FIG. 43, each of the needles 168 has a suture shuttle 170 trailing distally therefrom. Each of the suture shuttles 170 is coupled to its associated one of the implants 26a, 26b, which in this illustrated embodiment is accomplished by looping the suture shuttle 170 through one pair of holes 32 formed through the sidewall of the implant 26a, 26b.

An embodiment of use of the construct of FIG. 43 is illustrated in FIGS. 49-55 in which the needles 168 are used to advance the implants 26a, 26b through meniscus tissue 172 in a meniscus repair procedure, although the construct can be used in other types of surgical procedures. In general, this use may ensure that the implant 26a, 26b is properly seated before cutting the suture shuttle 170. The construct of FIG. 42 can be used similar to that discussed below regarding FIGS. 49-55.

Figure 49:
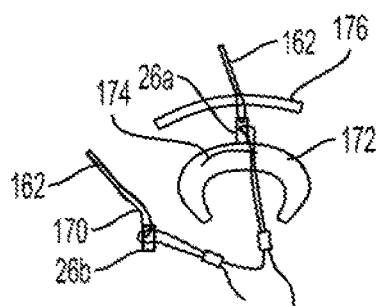
FIG. 49 is a schematic view of meniscus tissue with one of the needles of FIG. 43 and one of the implants of FIG. 43 advanced therethrough.
Figure 50:
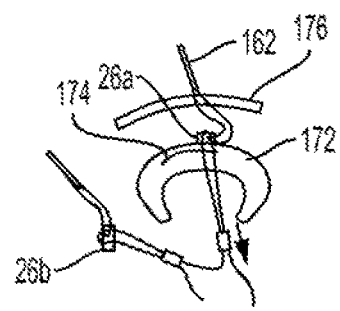
FIG. 50 is a schematic view of the meniscus tissue of FIG. 49 with the one of the implants being tensioned.
Figure 51:
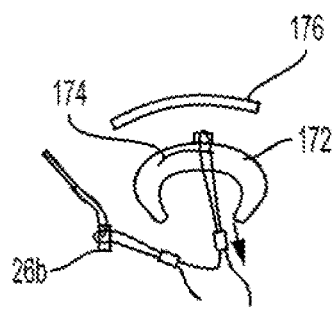
FIG. 51 is a schematic view of the meniscus tissue of FIG. 50 with the one of the needles removed and the one of the implants being tensioned.
Figure 52:
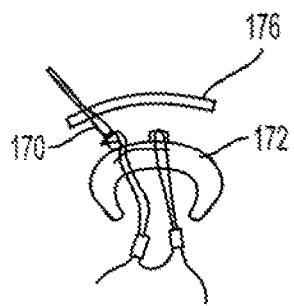
FIG. 52 is a schematic view of the meniscus tissue of FIG. 51 with another of the needles of FIG. 35 and another of the implants of FIG. 35 advanced therethrough.
Figure 53:
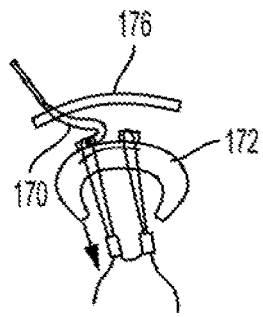
FIG. 53 is a schematic view of the meniscus tissue of FIG. 52 with the other of the implants being tensioned.
Figure 54:
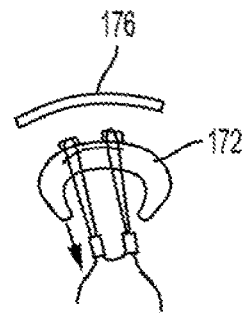
FIG. 54 is a schematic view of the meniscus tissue of FIG. 53 with the other of the needles removed and the other of the implants being tensioned.
Figure 55:
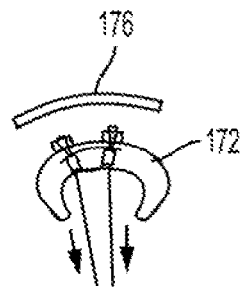
FIG. 55 is a schematic view of the meniscus tissue of FIG. 54 with the two implants being tensioned.

FIG. 49 shows a first one of the needles 162 and its associated first implant 26a advanced through the meniscus 172 on one side of a tear 174 in the meniscus 172 with the first needle 162 being advanced out of the patient's body through the patient's skin 176. FIG. 50 shows the suture loop associated with the first implant 26a being pulled down (e.g., tensioned) to toggle the first implant 26a sideways against the meniscus 172. If the implant 26a pulls out during this pulling and toggling, the first needle 162 can be pulled repeatedly until the first implant 26a is secure in place. FIG. 51 shows the suture shuttle 170 associated with the first needle 162 having been cut to allow removal of the first needle 162 and suture shuttle 170 from the patient's body by being pulled out through the skin 176. FIG. 51 also shows the suture loop associated with the first implant 26a being pulled down to toggle the implant 26a sideways against the meniscus 172 since the cutting of the suture shuttle 170 and/or the removal of the suture shuttle 170 and needle 162 may have jostled the first implant 26a out of position. FIG. 52 shows a second one of the needles 162 and its associated second implant 26b advanced through the meniscus 172 on the other side of the tear 174 in the meniscus 172 with the second needle 162 being advanced out of the patient's body through the patient's skin 176. FIG. 53 shows the suture loop associated with the second implant 26b being pulled down to toggle the second implant 26b sideways against the meniscus 172. FIG. 54 shows the suture shuttle 170 associated with the second needle 168 having been cut to allow removal of the second needle 138 and suture shuttle 170 from the patient's body by being pulled out through the skin 176. FIG. 54 also shows the suture loop associated with the second implant 26b being pulled down to toggle the implant 26b sideways against the meniscus 172 since the cutting of the suture shuttle 170 and/or the removal of the suture shuttle 170 and needle 168 may have jostled the second implant 26b out of position. FIG. 55 shows the first and second suture tails being tensioned to secure their associated first and second implants 26a, 26b in position against the meniscus 172 on either side of the tear 174. The method of FIGS. 49-55 can be performed using a steerable cannula, although one is not illustrated in FIGS. 49-55.

Figure 70:
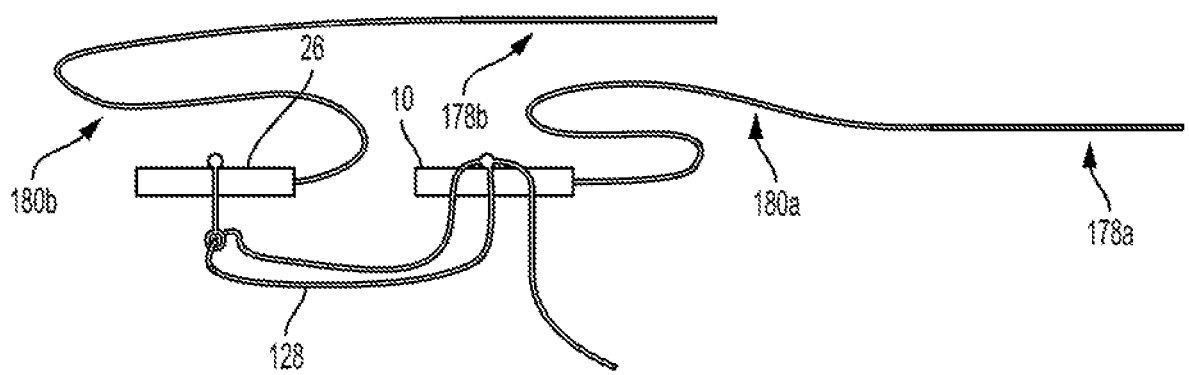
FIG. 70 is a side cross-sectional view of two of the implants of FIG. 1 each coupled to a needle.

FIG. 70 illustrates another embodiment of a construct for advancing a plurality of implants through tissue using a plurality of needles, each needle being flexible and being associated with one of the implants. The construct of FIG. 70 is illustrated using the implants 10, 26 of FIGS. 1 and 4 attached together using the technique of FIG. 29 but can be similarly used with other embodiments of implants and suture attachment techniques, such as the techniques of FIGS. 30-33. In the construct of FIG. 70, each of the needles 178a, 178b has a suture 180a, 180b trailing distally therefrom. Each of the sutures 180a, 180b is coupled to its associated one of the implants 10, 26.

Figure 71:
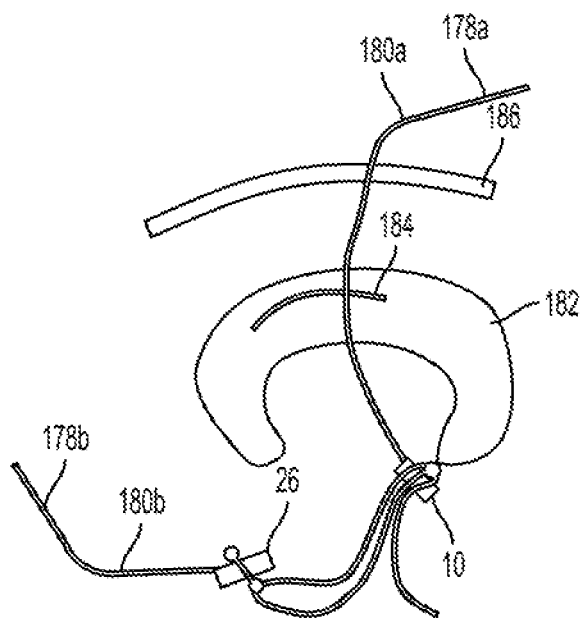
FIG. 71 is a schematic view of meniscus tissue with one of the needles of FIG. 70 advanced therethrough.
Figure 72:
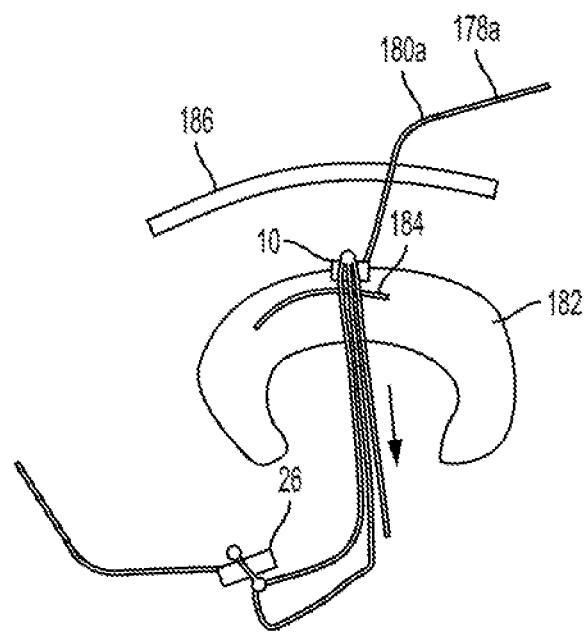
FIG. 72 is a schematic view of the meniscus tissue of FIG. 71 with one of the implants of FIG. 70 advanced therethrough and with the one of the implants being tensioned.
Figure 73:
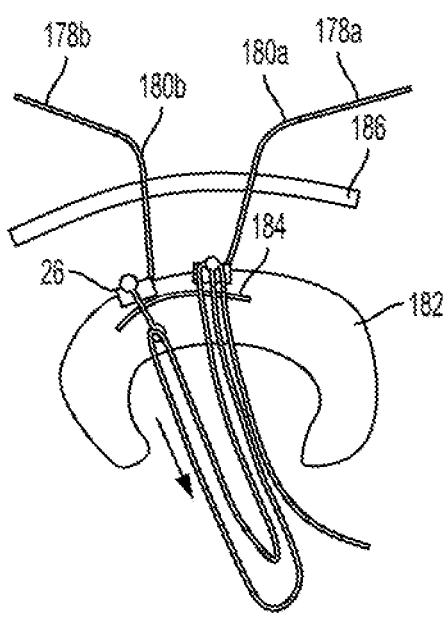
FIG. 73 is a schematic view of the meniscus tissue of FIG. 72 with the other of the needles of FIG. 70 and the other of the implants of FIG. 70 advanced therethrough.
Figure 74:
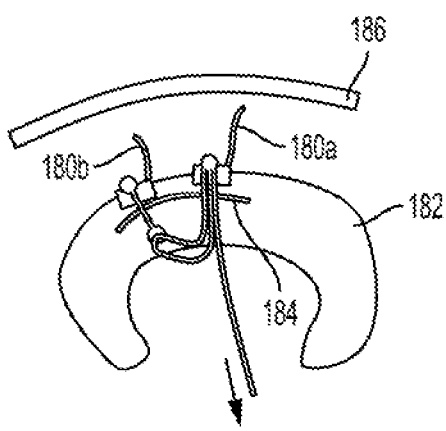
FIG. 74 is a schematic view of the meniscus tissue of FIG. 73 with the needles removed and with the implants being tensioned.

An embodiment of use of this construct is illustrated in FIGS. 71-74 in which the needles 178a, 178b are used to advance the implants 10, 26 through meniscus tissue 182 in a meniscus repair procedure, although the construct can be used in other types of surgical procedures. FIG. 71 shows a first one of the needles 178a advanced through the meniscus 182 on one side of a tear 184 in the meniscus 182 with the first needle 178a being advanced out of the patient's body through the patient's skin 186. FIG. 72 shows the suture loop associated with the first implant 10 being pulled down (e.g., tensioned) to toggle the first implant 10 sideways against the meniscus 182. FIG. 73 shows a second one of the needles 178b and its associated second implant 26 advanced through the meniscus 182 on the other side of the tear 184 in the meniscus 182 with the second needle 178b being advanced out of the patient's body through the patient's skin 186. FIG. 73 also shows the suture loop associated with the second implant 26 being pulled down to toggle the second implant 26 sideways against the meniscus 182. FIG. 74 shows the suture bridge extending between the first and second implants 10, 26 being tensioned by pulling the suture tail to secure the first and second implants 10, 26 in position against the meniscus 182 on either side of the tear 184. FIG. 74 also shows the first and second sutures 180a, 180b associated with the first and second needles 178a, 178b having been cut to allow removal of the first and second needles 178a, 178b from the patient's body by being pulled out through the skin 186, with FIG. 74 showing the needles 178a, 178b already having been removed. The method of FIGS. 71-74 can be performed using a steerable cannula, although one is not illustrated in FIGS. 71-74.

In other embodiments, instead of using a plurality of needles to deliver a plurality of pledgets, each of a plurality of implants coupled together with one or more sutures can be coupled to a single needle configured to sequentially advance each of the implants through tissue (e.g., meniscus in a meniscal repair procedure) such that only one needle is used to advance the implants through the tissue. Using a single needle may require only one incision to be made in the patient, which may provide any number of benefits over using multiple needles, such as improved cosmesis and less tissue trauma. In meniscus repair, use of a single needle is generally referred to as an all-inside surgical technique.

The needles described herein that are configured to deliver multiple implants, e.g., in an all-inside procedure, can have a variety of sizes, shapes, and configurations. The needle can be made from any of a variety of materials, e.g., stainless steel, nitinol, etc. In an exemplary embodiment, the needle is a solid member and is flexible. The needle being solid may help provide structural stability to the needle. The needle being flexible may facilitate desired positioning of the needle relative to tissue through which it is desired to be advanced and/or may compensate for an angle of approach to the desired tissue not being ideal because the needle can be directed to tissue at another angle due to its flexibility such as with a steerable cannula, as discussed further below. The needle, while flexible so as to allow flexing thereof, such as for use with a steerable cannula that bends the needle, has sufficient structural stability along its longitudinal length due to being solid and/or due to the material(s) from which the needle is made to allow the needle to be advanced longitudinally through tissue to deliver implant(s) therethrough.

The needle can have a variety of sizes. The needle can be configured to be advanced through a steerable cannula, as discussed further below, and can have a length that is long enough to allow a distal portion of the needle to be advanced distally beyond the steerable cannula. In an exemplary embodiment, the needle has a maximum outer diameter of in a range of about 0.020 in. to 0.050 in., e.g., about 0.035 in.

A distal tip of the needle can have a variety of configurations. In an exemplary embodiment, such as with the needle 36 of FIGS. 9A-9B, the distal tip can be sharp and configured to pierce through tissue, such as by being beveled or having a sharp triangular tip similar to a trocar tip. The needle having a sharp distal tip may facilitate penetration of the needle through tissue (e.g., meniscus).

In an exemplary embodiment, the needle has a D-shape cross section in at least a portion thereof. The needle can thus have a substantially flat surface extending along a length thereof. A person skilled in the art will appreciate that a surface may not be precisely flat but nevertheless be considered to be substantially flat due to, e.g., manufacturing tolerances and/or tolerances in measurement devices. In some embodiments, the flat surface can extend along an entire length of the needle except at a tapering distal tip thereof (e.g., where the needle is beveled, has a trocar-like tip, etc.). In some embodiments, the flat surface can extend along a partial length of the needle in a distal portion thereof except at a tapering distal tip of the needle. In some embodiments, the flat surface can extend along the entire length of the needle, including the distal tip thereof. In other exemplary embodiments, the substantially flat surface can instead be slightly domed. In this way, a radius of curvature on this surface would be higher (e.g., about 2 times higher) than a radius of curvature for an outer diameter of the needle.

One embodiment of a needle configured to deliver a plurality of implants is the needle 24 of FIGS. 2-3 and the needle 28 of FIGS. 5-6. The needle 24, 28 in this illustrated embodiment has a cone-shaped pointed distal tip.

Figure 9B:
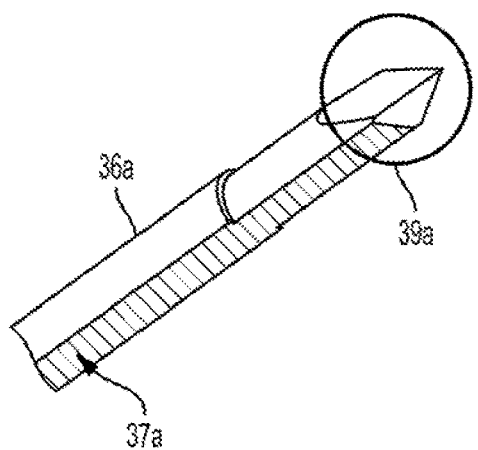
FIG. 9B is a perspective view of a distal portion of another embodiment of a needle.

Another embodiment of a needle configured to deliver a plurality of implants is the needle 36 of FIGS. 8-9A and the needle 118 of FIGS. 24-26. The needle 36, 118 in this illustrated embodiment has a flat surface 37 extending along a length thereof and has a beveled distal tip 39. FIG. 9B illustrates another embodiment of a needle 36a that similarly includes a flat surface 37a extending along a length thereof and has a beveled distal tip 39a.

Figure 56:
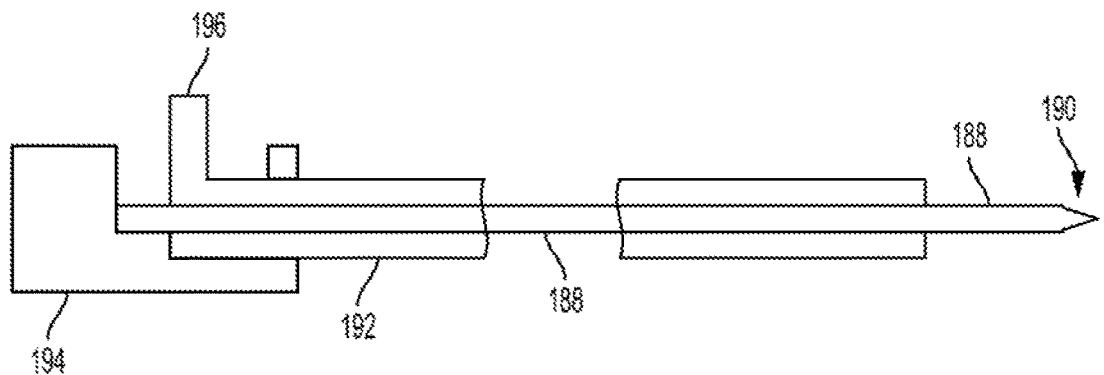
FIG. 56 is a side cross-sectional, partial schematic view of another embodiment of a needle.

Another embodiment of a needle 188 configured to deliver a single implant (not shown) is illustrated in FIG. 56. The needle 188 in this illustrated embodiment is flexible, is in the form of a wire, has a flat surface along a length thereof, and has a sharp distal tip 190. FIG. 56 shows the needle 188 as part of a delivery system configured to deliver the implant. A flexible tube 192 of the delivery system extends distally from a handle 194 of the delivery system and is slidably disposed around the needle 188. The handle 194 has an actuator 196 in the form of a thumb drive coupled thereto that is operatively coupled to the flexible tube 192. The thumb drive 196 is configured to be manipulated by a user (directly by hand or through another tool such as a grasper or a robotic surgical system) to cause slidable movement of the tube 192 relative to the needle 188, e.g., distal sliding of the thumb drive 196 causes the tube 192 to slide distally and proximal sliding of the thumb drive 196 causes the tube 192 to slide proximally.

Figure 57:
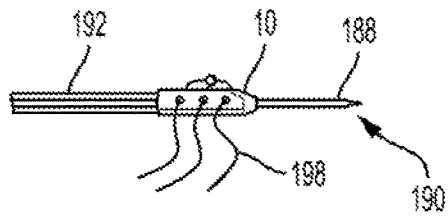
FIG. 57 is a side, partially cross-sectional view of the implant of FIG. 1 coupled to the needle of FIG. 56.

FIG. 57 shows a distal portion of the delivery system with an implant coupled thereto. The implant is the implant 10 of FIG. 1, but another type of implant can be similarly coupled to and delivered by the delivery system. The implant 10 is mounted on the needle 188 with the needle 188 extending through the cannulated interior of the implant 10 with a distal portion of the needle 188, including the sharp distal tip 190, extending distally beyond the implant 10. The needle 188 extending distally beyond the implant 10 may allow the needle 188 to reach a farthest penetration depth into tissue (e.g., meniscus) without the implant 10. A proximal end surface of the implant 10 abuts a distal end surface of the tube 192.

The suture 198 coupled to the implant 10 is pinched within the implant's inner lumen 12 in a press fit between the implant 10 (e.g., an inner surface thereof) and the needle 188 (e.g., the flat surface thereof). The press fit holds the implant 10 in position on the needle 188 before deployment therefrom. The actuation of the thumb drive 196 to push the tube 192 distally exerts enough force on the implant 10 to overcome the force of the press fit, thereby causing the implant 10 to move distally over the needle 188 and be released therefrom. The flat surface of the needle 188 can extend along the needle 188 at least along an entire length of the needle 188 along which the implant 10 is seated pre-deployment with its proximal end surface abutting the tube 192. This location of the flat surface may help ensure that the suture 198 coupled to the implant 10 is pinched in the press fit between the implant 10 and the needle's flat surface.

Figure 58:
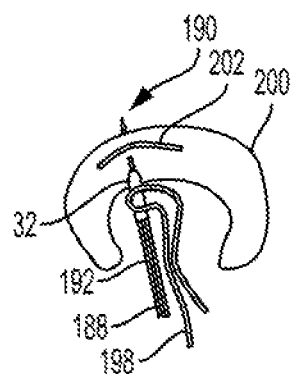
FIG. 58 is a schematic view of meniscus tissue with the needle of FIG. 56 advanced therethrough, the needle having the implant of FIG. 1 loaded thereon.
Figure 59:
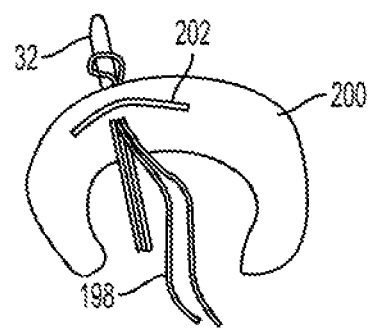
FIG. 59 is a schematic view of the meniscus tissue of FIG. 58 with the implant advanced therethrough.
Figure 60:
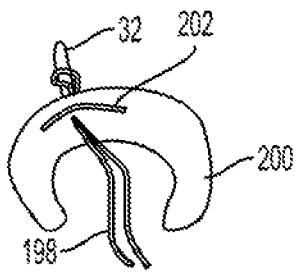
FIG. 60 is a schematic view of the meniscus tissue of FIG. 59 with the needle withdrawn.
Figure 61:
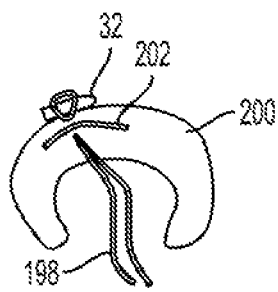
FIG. 61 is a schematic view of the meniscus tissue of FIG. 60 with the implant having been tensioned.

FIGS. 58-61 illustrate an embodiment of use of the delivery system of FIG. 56 to deliver the implant 32 (see FIG. 4) loaded thereon as in FIG. 57. The use is illustrated for a meniscus repair procedure but can be similarly performed in another type of surgical procedure. FIG. 58 shows the needle 188 advanced through the meniscus 200 at a location of a tear 202 in the meniscus 200 with a distal tip 190 of the needle 188 on a far side of the meniscus 200 and the implant 32 on a near side of the meniscus 200. FIG. 59 shows the implant 32 having been advanced through the meniscus 200 to the far side of the meniscus 200 in response to actuation of the thumb drive 196 distally advancing the tube 192. The thumb drive 196 is advanced distally to cause distal advancement of the tube 192 relative to the needle 188, thereby causing the implant 32 loaded on the needle 188 to be pushed distally off the needle 188. FIG. 60 shows the delivery system having been removed by being pulled distally, leaving the implant 32 (and suture 198 attached thereto) within the patient's body. FIG. 61 shows the implant 32 having been toggled into position against the meniscus 200 by tensioning the suture 198 attached thereto. The suture tails can then be trimmed, as discussed above.

Figure 62:
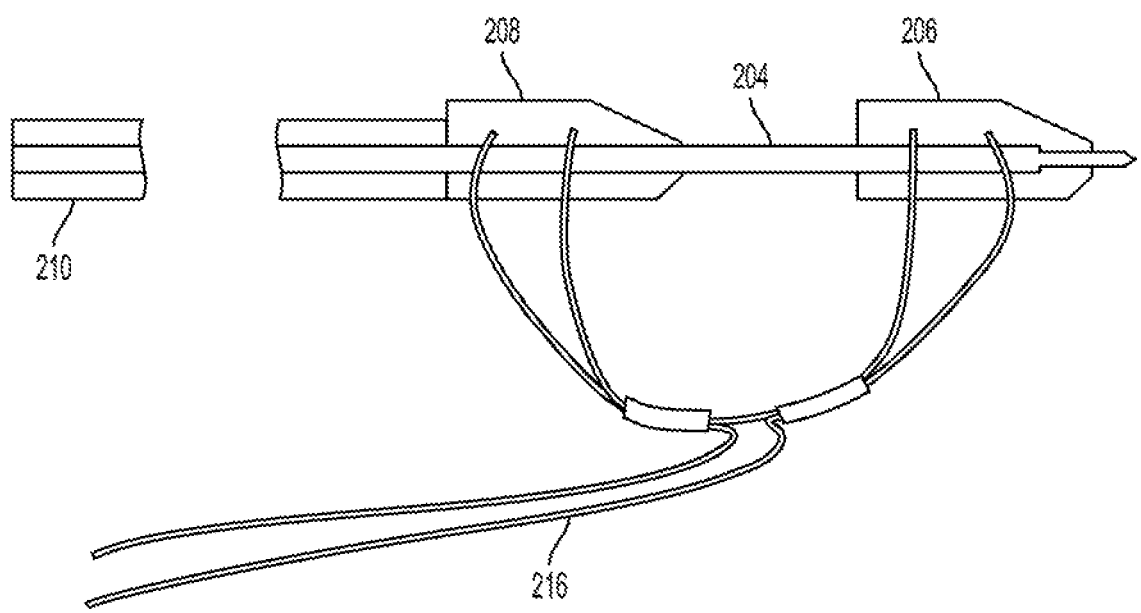
FIG. 62 is a side cross-sectional, partial view of embodiments of two implants coupled to another embodiment of a needle.
Figure 69:
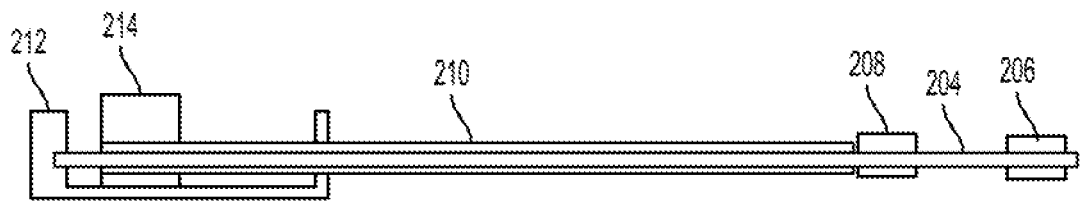
FIG. 69 is a side cross-sectional view of the implants and the needle of FIG. 62.

Another embodiment of a needle 204 configured to deliver a plurality of implants 206, 208 is illustrated in FIGS. 62 and 69. The needle 204 in this illustrated embodiment is flexible, has a flat surface along a length thereof, and has a sharp distal tip. FIGS. 62 and 69 show the needle 204 as part of a delivery system configured to deliver the implants 206, 208. The delivery system is similar to the delivery system of FIG. 56 and includes a flexible tube 210, a handle 212, and an actuator 214 in the form of a sleeve knob.

FIGS. 62 and 69 also show first and second implants 206, 208 coupled to the needle 204. The first implant 206 is loaded on the needle 204 distal to the second implant 208 and is configured to be deployed from the needle 204 before the second implant 208 is deployed therefrom. The needle 204 includes a stop surface that abuts a stop surface of the first implant 206. The implant 34 of FIG. 7 is one example of the first implant 206. The needle 204 does not include a stop surface for the second implant 208. A proximal end surface of the second implant 208 abuts a distal end surface of the tube 210. The implant 114 of FIG. 23 is one example of the second implant 208. The first and second implants 206, 208 are coupled together with a suture 216 according to the construct of FIG. 30, although the first and second implants 206, 208 can be coupled together with a suture in other ways. FIG. 62 also shows the suture 216 pinched in a press fit between the needle 204 (e.g., the flat surface thereof) and each of the first and second implants 206, 208, similar to that discussed above regarding the implant 10 and needle 188 of FIG. 57.

Figure 63:
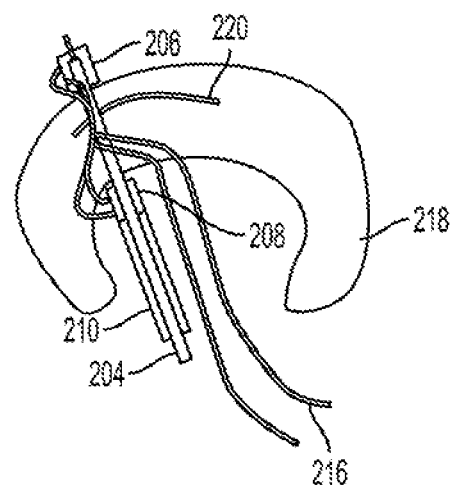
FIG. 63 is a schematic view of meniscus tissue with the needle and one of the implants of FIG. 62 advanced therethrough.

FIG. 63-68 illustrate an embodiment of use of the delivery system of FIGS. 62 and 69 to deliver the implants 206, 208 loaded thereon. The use is illustrated for a meniscus repair procedure but can be similarly performed in another type of surgical procedure. FIG. 63 shows the needle 204 advanced through the meniscus 218 on one side of a tear 220 in the meniscus 218 with a distal tip of the needle 204 on a far side of the meniscus 218, the first implant 206 also on the far side of the meniscus 218, and the second implant 208 on a near side of the meniscus 218. The stop surfaces of the first implant 206 and the needle 204 facilitate the advancement of the first implant 206 through the meniscus 218 with the needle 204.

Figure 64:
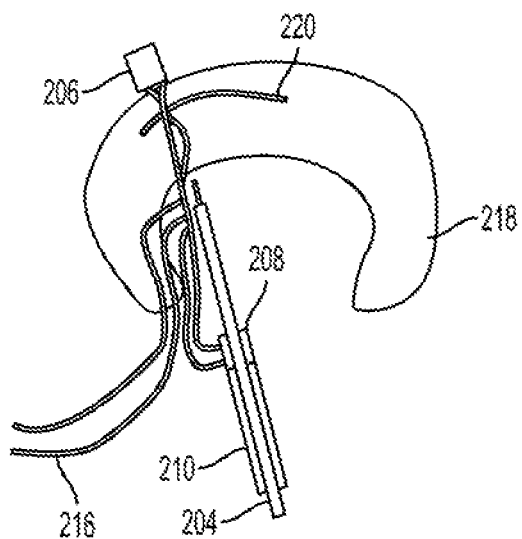
FIG. 64 is a schematic view of the meniscus tissue of FIG. 63 with the needle withdrawn.

FIG. 64 shows the needle 204 retracted from the far side of the meniscus 218 to the near side of the meniscus 218 with the first implant 206 remaining on the far side of the meniscus 218. The stop surfaces of the first implant 206 and the needle 204 become disengaged when the needle 204 is pulled in a proximal direction to move the needle 204 to the near side of the meniscus 218. The pull force of the needle 204 in the proximal direction is enough to overcome the press fit force, so the first implant 206 is not drawn back through the meniscus 218 with the needle 204. Additionally, as mentioned above, the first implant 206 can include a retention feature at its proximal end to help keep the first implant 206 on the far side of the meniscus 218 when the needle 204 is retracted therefrom.

Figure 65:
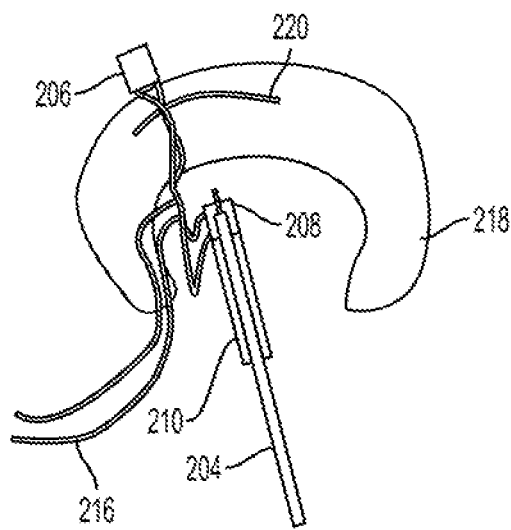
FIG. 65 is a schematic view of the meniscus tissue of FIG. 64 with the other of the implants advanced along the needle.

FIG. 65 shows the second implant 208 having been advanced distally along the needle 204 to the previous position of the first implant 206 on the needle 204. The needle 204 can include a detent (not shown), such as a ball, pin, etc., configured to engage a corresponding indentation (not shown), such as a hole, a socket, a depression, etc., formed in an inner lumen of the second implant 208 to temporarily hold the second implant 208 in this advanced position on the needle 204. Alternatively, the second implant 208 can include the detent and the needle 204 can include the corresponding indentation. As yet another alternative, the tube 210 can be locked to the needle 204 (e.g., using a detent and a corresponding indentation) instead of locking the second implant 208 to the needle 204 using a detent or indentation. The second implant 208 is advanced to this advanced position by the tube 210 pushing the second implant 208 distally in response to actuation of the actuator 214 moving the tube 210 distally. Similar to that discussed above, the tube 210 can exert enough force on the second implant 208 to overcome the press fit force holding the second implant 208 on the needle 204, thereby allowing the second implant 208 to advance along the needle 204 and be deployed therefrom.

Figure 66:
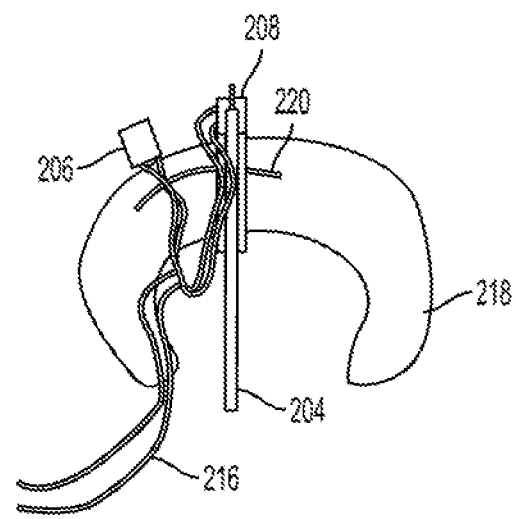
FIG. 66 is a schematic view of the meniscus tissue of FIG. 65 with the needle and the other of the implants advanced therethrough.

The needle 204 back on the near side of the meniscus 218 can be adjusted in position to deploy the second implant 208 on the other side of the tear in the meniscus 218. FIG. 66 shows the needle 204 advanced together with the tube 210 through the meniscus 218 on the other side of the tear 220 in the meniscus 218 with the distal tip of the needle 204 on the far side of the meniscus 218 and the second implant 208 as well as the distal tip of the tube 210 also on the far side of the meniscus 218.

Figure 67:
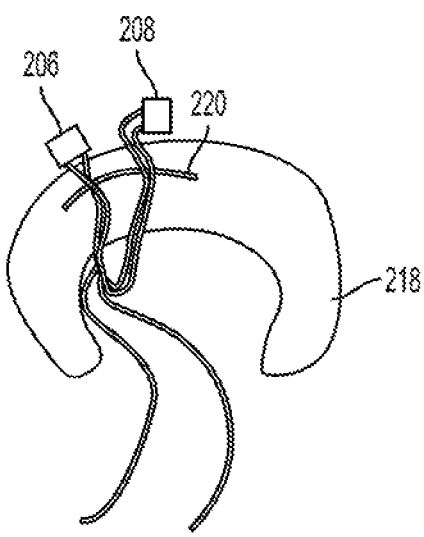
FIG. 67 is a schematic view of the meniscus tissue of FIG. 66 with the needle withdrawn.

FIG. 67 shows the delivery system retracted from the far side of the meniscus 218 to the near side of the meniscus 218 with the second implant 208 remaining on the far side of the meniscus 218. The pull force of the needle 204 in the proximal direction is enough to overcome the press fit force, so the second implant 208 is not drawn back through the meniscus 218 with the needle 204. Additionally, as mentioned above, the second implant 208 can include a retention feature at its proximal end to help keep the second implant 208 on the far side of the meniscus 218 when the needle 204 is retracted therefrom.

Figure 68:
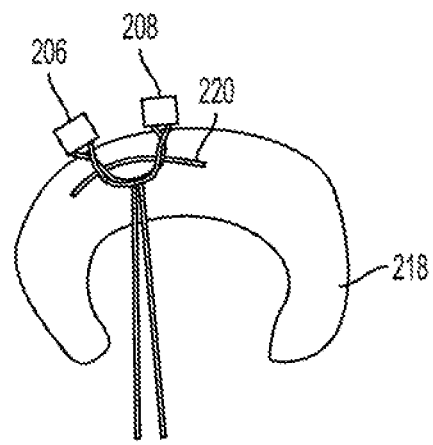
FIG. 68 is a schematic view of the meniscus tissue of FIG. 67 with the two implants having been tensioned.

FIG. 68 shows the first and second implants 206, 208 having been toggled into position against the meniscus 218 by tensioning the suture tails attached thereto. As mentioned above, the suture tails can be tensioned sequentially or can be tensioned simultaneously. The suture tails can then be trimmed, as discussed above.

Figure 82:
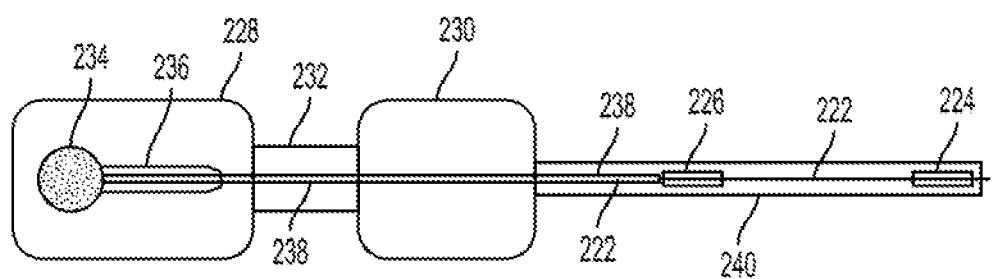
FIG. 82 is a partially transparent side schematic view of one embodiment of a delivery system having two implants disposed in a shaft thereof.

Another embodiment of a needle 222 configured to deliver a plurality of implants 224, 226 is illustrated in FIG. 82. The needle 222 in this illustrated embodiment is flexible, has a flat surface along a length thereof, and has a sharp distal tip. FIG. 82 shows the needle 222 as part of a delivery system configured to deliver the implants 224, 226. The delivery system is similar to the delivery system of FIG. 56 and includes a movable handle 228, a stationary handle 230, a spacer 232 along which the movable handle 228 is configured to selectively slide proximally and distally, an actuator 234 in the form of a knob selectively slidable proximally and distally in a slot 236 formed in the movable handle 228, a flexible tube 238 extending distally from the movable handle 228 and configured to slide in response to sliding movement of the actuator 234, and an elongate shaft 240 extending distally from the stationary handle 230.

FIG. 82 also shows first and second implants 224, 226 coupled to the needle 222. The first implant 224 is loaded on the needle 222 distal to the second implant 226 and is configured to be deployed from the needle 222 before the second implant 226 is deployed therefrom. The needle 222 includes a stop surface (too small to be visible in FIG. 82) that abuts a stop surface (too small to be visible in FIG. 82) of the first implant 224. The implant 34 of FIG. 7A is one example of the first implant 224. The needle 222 does not include a stop surface for the second implant. A proximal end surface of the second implant 226 abuts a distal end surface of the tube 238. The implant 114 of FIG. 23 is one example of the second implant 226. The first and second implants 224, 226 are coupled together with a suture (not shown), such as according to the construct of FIG. 30 or in another way. The suture is pinched in a press fit between the needle 222 (e.g., the flat surface thereof) and each of the first and second implants 224, 226, similar to that discussed above regarding the implant 10 and needle 188 of FIG. 57.

FIG. 83-90 illustrate an embodiment of use of the delivery system of FIG. 82 to deliver the implants 224, 226 loaded thereon. The use is illustrated for a meniscus repair procedure but can be similarly performed in another type of surgical procedure. FIG. 83 shows the delivery system with a distal end thereof (e.g., a distal end of the elongate shaft) positioned adjacent meniscus tissue 242. A distal end of the needle 222 can extend distally beyond the distal end of the shaft 240, as shown in FIGS. 82 and 83, or the distal end of the needle 222 can be contained within an inner lumen of the elongate shaft 240 in which the needle 222 is slidably disposed.

FIG. 84 shows the needle 222 advanced through the meniscus 242 with a distal tip of the needle 222 on a far side of the meniscus 242, the first implant 224 also on the far side of the meniscus 242, and the second implant 226 on a near side of the meniscus 242 and still contained within the inner lumen of the elongate shaft 240 and having been pushed forward to keep its distance to the first implant 224. The stop surfaces of the first implant 224 and the needle 222 facilitate the advancement of the first implant 224 through the meniscus 242 with the needle 222. The needle 222 and the first implant 224 have been advanced through the meniscus 242 by moving the movable handle 228 distally toward and relative to the stationary handle 230.

FIG. 85 shows the needle 222 retracted from the far side of the meniscus 242 to the near side of the meniscus 242 with the first implant 224 remaining on the far side of the meniscus 242. The stop surfaces of the first implant 224 and the needle 222 become disengaged when the needle 222 is pulled in a proximal direction to move the needle 222 to the near side of the meniscus 242. The pull force of the needle 222 in the proximal direction is enough to overcome the press fit force, so the first implant 224 is not drawn back through the meniscus 242 with the needle 222. Additionally, as mentioned above, the first implant 224 can include a retention feature at its proximal end to help keep the first implant 224 on the far side of the meniscus 242 when the needle 222 is retracted therefrom. The needle 222 has been retracted back through the meniscus 242 by moving the movable handle 228 proximally away from and relative to the stationary handle 230.

FIG. 86 shows the second implant 226 having been advanced distally along the needle 222 by sliding the knob 234 distally in the slot 236 to slide the tube 238 distally and thereby push the second implant 226 distally. The tube 238 is now locked to the movable handle 228 (by detents, etc.), holding the second implant 226 in position on the needle 222 which is the initial position of the first implant 224.

Figure 87:
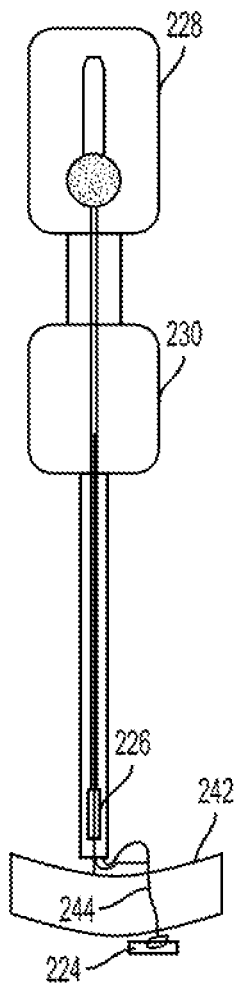
FIG. 87 is a side schematic view of the meniscus tissue of FIG. 86 with the delivery system changed in position relative thereto.
Figure 88:
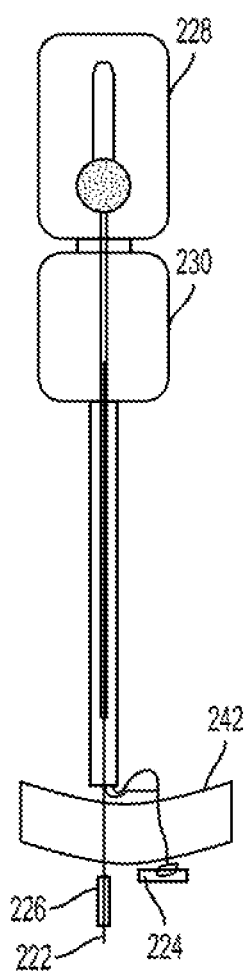
FIG. 88 is a side schematic view of the meniscus tissue of FIG. 87 with the needle and the other of the implants advanced therethrough.

FIG. 87 shows the delivery system moved to another location relative to the meniscus 242 with a distal end of the delivery system (e.g., the distal end of the elongate shaft 240) positioned adjacent meniscus tissue 242. FIG. 88 shows the needle 222 advanced through the meniscus 242 on the other side of the tear in the meniscus 242 with the distal tip of the needle 222 on the far side of the meniscus 242 and the second implant 226 also on the far side of the meniscus 242. The engaged tube 238 facilitates the advancement of the second implant 226 through the meniscus 242 with the needle 222. The needle 222, the tube 238, and the second implant 226 have been advanced through the meniscus 242 by moving the movable handle 228 distally toward and relative to the stationary handle 230. For clarity of illustration of the needle 22, second implant 226, and sutures 244, the tube 238 is shown in FIG. 88 in a distal, non-advanced position instead of its actual, advanced position with a distal end thereof abutting a proximal end of the second implant 226.

Figure 89:
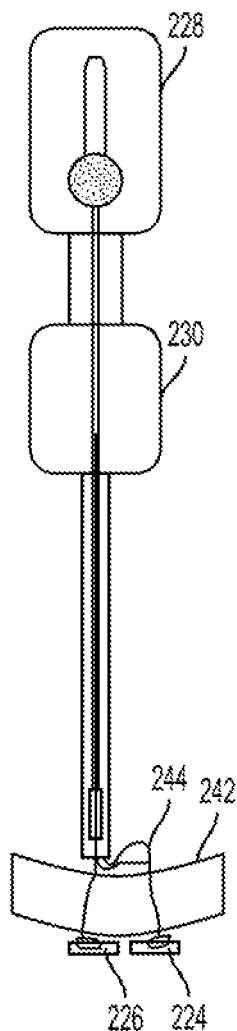
FIG. 89 is a side schematic view of the meniscus tissue of FIG. 88 with the needle withdrawn.

FIG. 89 shows the needle 222 retracted from the far side of the meniscus 242 to the near side of the meniscus 242 with the second implant 226 remaining on the far side of the meniscus 242 and with the suture 244 extending between the first and second implants 224, 226. The pull force of the needle 222 in the proximal direction is enough to overcome the press fit force, so the second implant 226 is not drawn back through the meniscus 242 with the needle 222. Additionally, as mentioned above, the second implant 226 can include a retention feature at its proximal end to help keep the second implant 226 on the far side of the meniscus 242 when the needle 222 is retracted therefrom. The needle 222 has been retracted back through the meniscus 242 by moving the movable handle 228 proximally away from and relative to the stationary handle 230.

Figure 90:
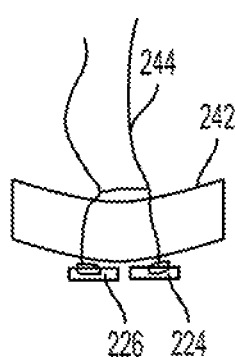
FIG. 90 is a side schematic view of the meniscus tissue of FIG. 89 with the delivery system removed.

FIG. 90 shows the first and second implants 224, 226 having been toggled into position against the meniscus 242 by tensioning the suture tails attached thereto. As mentioned above, the suture tails can be tensioned sequentially or can be tensioned simultaneously. The suture tails can then be trimmed, as discussed above.

FIG. 94 illustrates an embodiment of a delivery system configured to be reloadable. The delivery system includes only one needle 246. In use, a first implant 248 loaded on the needle 246 is deployed by pushing the needle 246 forward (e.g., distally) and then pulling the needle 246 back (e.g., proximally). The needle 246 is pulled back far enough to pick up a second implant 250 on a tip of the needle 246. The second implant 250 is deployed by pushing the needle 246 forward.

FIG. 95 illustrates an embodiment of a delivery system configured to be stackable. The delivery system includes two needles 252, 254. In use, a first implant 256 loaded on the first needle 252 is deployed by pushing the first needle 252 forward (e.g., distally) and then pulling back (e.g., proximally) on the first needle 252. The first needle 252 is then moved away from a center of the instrument 258 and the second needle 254 having a second implant 260 loaded thereon is moved into the center of the instrument 258. The second implant 260 is deployed by pushing the second needle 254 forward.

Delivery Devices

The implants described herein can be advanced through tissue in any of a variety of ways. For example, the implants can be delivered to a surgical site using a driver. The implant can be configured to cut tissue (e.g., meniscus) to facilitate passage of the implant and the driver associated therewith through the tissue.

Figure 75:
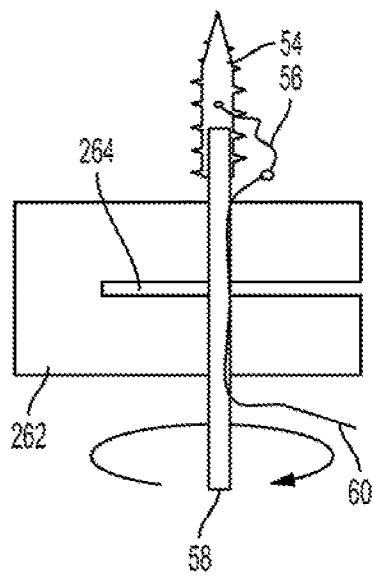
FIG. 75 is a schematic view of meniscus tissue with the implant and driver of FIG. 12 advanced therethrough.
Figure 76:
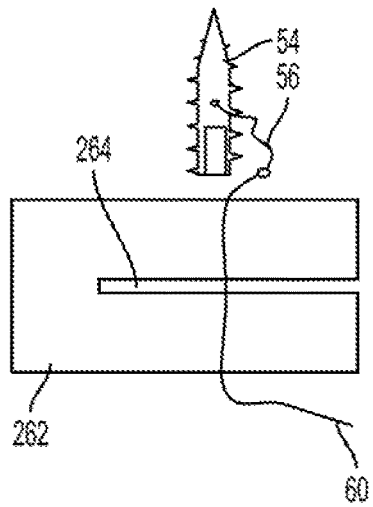
FIG. 76 is a schematic view of the meniscus tissue of FIG. 75 with the driver withdrawn.
Figure 77:
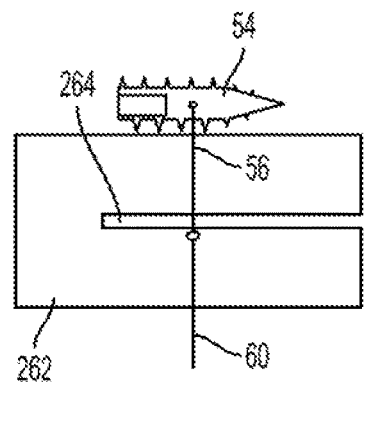
FIG. 77 is a schematic view of the meniscus tissue of FIG. 76 with the implant tensioned.

An embodiment of advancing the implant 54 of FIG. 11 through meniscus tissue 262 using the driver 58 of FIG. 12 is illustrated in FIGS. 75-78. Although the method of FIGS. 75-78 is shown with respect to a meniscus repair procedure, the method can be used in other types of surgical procedures. FIG. 75 shows the implant 54 and a distal portion of the driver 58 advanced through the meniscus 262 on one side of a tear 264 in the meniscus 262. The driver 58 has been rotated about a longitudinal axis thereof to correspondingly rotate the implant 54 and thereby drive the implant 54 through the meniscus 262. The suture attached to the implant 54 extends from the implant 54 on a far side of the meniscus 262 and through the meniscus 262 to a near side of the meniscus 262. FIG. 76 shows the driver 58 removed from the implant 54. The driver 58 can be so removed by pulling it proximally. As mentioned above, the implant 54 can include a retention feature at its proximal end to help keep the first implant 54 on the far side of the meniscus 262 when the driver 58 is retracted therefrom. FIG. 77 shows the implant 54 having been toggled into position against the meniscus 262 by tensioning the suture attached thereto. As shown, the thread of the implant 54 is not within the tissue 262 but is instead located substantially outside of the tissue 262, as the thread facilitates passage of the implant 54 through the tissue, with the suture and not the thread holding the implant 54 in position relative to the tissue 262. A person skilled in the art will appreciate that the thread may minimally dig into the tissue 262 but nevertheless be considered to be located substantially outside of the tissue 262 due to the thread not being threaded into the tissue 262 and/or not damaging the tissue 262 due to the minimal digging.

Figure 78:
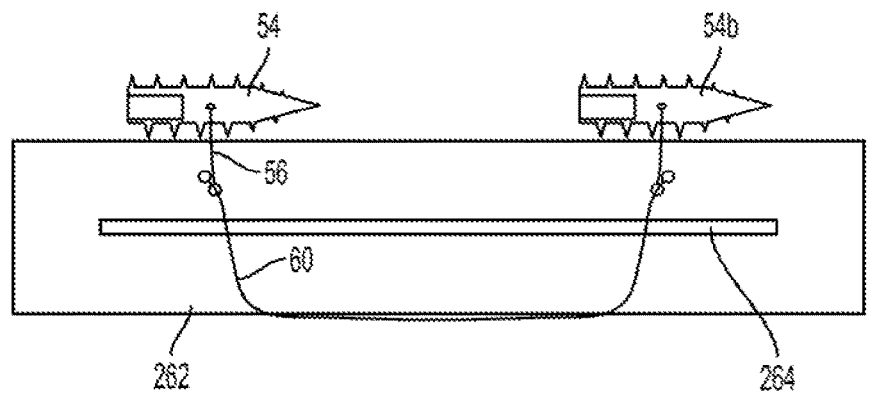
FIG. 78 is a schematic view of the meniscus tissue of FIG. 77 with another implant coupled thereto.

The suture attached to the implant 54 can be attached to a second implant 54b. The driver 58 can be used to drive the second implant 54b through the meniscus 262 (similar to FIG. 75) on another side of the meniscal tear 264, the driver 58 can be removed from the second implant 54b (similar to FIG. 76), and the suture can be tensioned to toggle the second implant 54b into position (similar to FIG. 77). Two implants 54, 54b can thus be positioned on either side of the tear 264, as shown in FIG. 78. Instead of using the same driver 58 to drive each of the two implants 54, 54b, a different driver can be used for each of the implants 54, 54b. As shown, the thread of the second implant 54b is not within the tissue 262 but is instead located substantially outside of the tissue 262, as the thread facilitates passage of the second implant 54b through the tissue 262, with the suture and not the thread holding the second implant 54b in position relative to the tissue 262.

Figure 79:
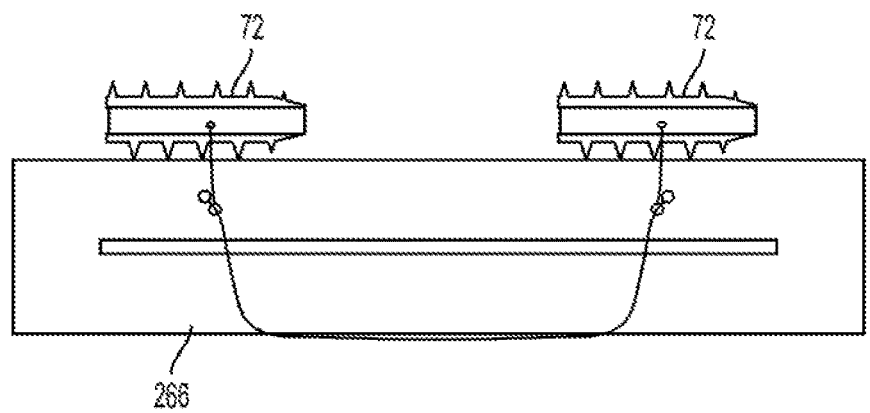
FIG. 79 is a schematic view of meniscus tissue with two of the implants of FIG. 13 coupled thereto.

An embodiment of advancing two of the implants 72 of FIG. 13 through meniscus tissue 266 using the driver 76 of FIG. 14 is illustrated in FIG. 79. Although the method of FIG. 79 is shown with respect to a meniscus repair procedure, the method can be used in other types of surgical procedures. The driver 76 can sequentially deliver the implants 72 through the meniscus, and the suture attached to the implants 72 can be tensioned, similar to that discussed above regarding FIGS. 75-78. As shown, the implants 72 are not within the tissue 266 but are instead located substantially outside of the tissue 266, as the threads facilitate passage of their respective implants 72 through the tissue, with the suture and not the threads holding the implants in position relative to the tissue 266.

Figure 80:
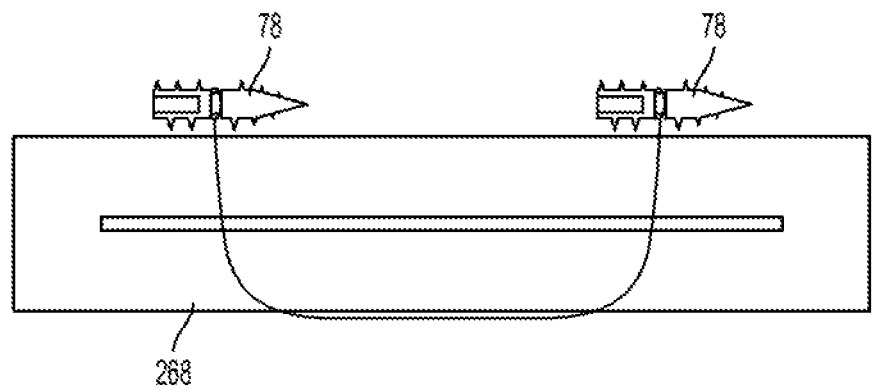
FIG. 80 is a schematic view of meniscus tissue with two of the implants of FIG. 15 coupled thereto.

An embodiment of advancing two of the implants 78 of FIG. 15 through meniscus tissue 268 using the driver 82 of FIG. 16 is illustrated in FIG. 80. Although the method of FIG. 80 is shown with respect to a meniscus repair procedure, the method can be used in other types of surgical procedures. The driver 82 can sequentially deliver the implants 78 through the meniscus 268, and the suture attached to the implants 78 can be tensioned, similar to that discussed above regarding FIGS. 75-78. As shown, the threads of the implants 78 are not within the tissue 268 but are instead located substantially outside of the tissue 268, as the threads facilitate passage of their respective implants 78 through the tissue 268, with the suture and not the threads holding the implants 78 in position relative to the tissue 268.

Figure 81:
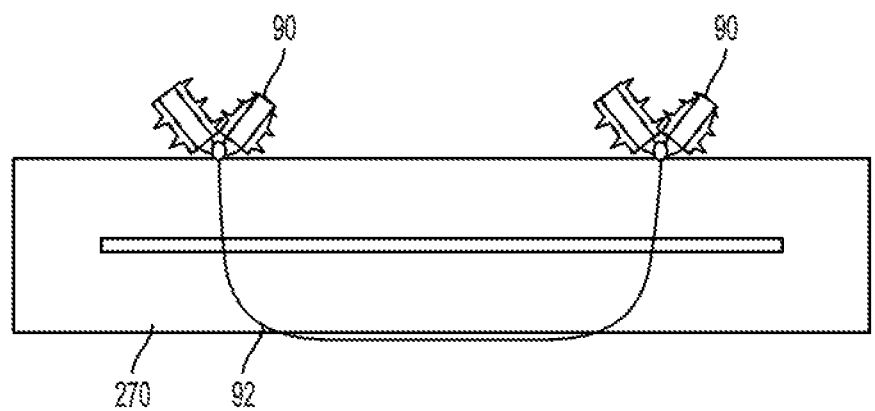
FIG. 81 is a schematic view of meniscus tissue with two of the implants of FIG. 17 coupled thereto.

An embodiment of advancing two of the implants 90 of FIG. 17 through meniscus tissue 270 using the driver 94 of FIG. 18 is illustrated in FIG. 81. Although the method of FIG. 81 is shown with respect to a meniscus repair procedure, the method can be used in other types of surgical procedures. The driver 94 can sequentially deliver the implants 90 through the meniscus 270, and the suture 92 attached to the implants 90 can be tensioned, similar to that discussed above regarding FIGS. 75-78. As shown, the threads of the implants 90 are not within the tissue 270 but are instead located substantially outside of the tissue 270, as the threads facilitate passage of their respective implants 90 through the tissue 270, with the suture 92 and not the threads holding the implants 90 in position relative to the tissue 270.

Cannulas

As mentioned above, one or more needles can be configured to deliver one or more implants to a surgical site. The one or more needles and the one or more implants can be advanced to the surgical site through a cannula. In an exemplary embodiment, the cannula can be configured to have advanced therethrough a delivery system that delivers one or more needles and one or more implants, such as the delivery systems of FIGS. 56, 62, 69, and 82.

The cannula through which the needle(s) and implant(s) are advanced can be configured to be re-used in a same surgical procedure to deliver multiple needles and implants (e.g., have multiple needles and multiple implants simultaneously or sequentially loaded therein) and/or can be configured to be re-used in different surgical procedures to deliver needles and implants to different patients.

In use, a distal end of the cannula can be positioned substantially at tissue through which the needle(s) and the implant(s) are to be delivered, e.g., adjacent to a meniscus tissue. The distal end of the cannula being substantially at the tissue includes the distal end of the cannula abutting the tissue so as to be in contact with a surface of the tissue, which may help ensure that the needle(s) and the implant(s) are advanced through the tissue at a desired point, e.g., the point at which the cannula's distal end contacts the tissue. The cannula's distal end may be near but not abut the tissue so as to be in contact therewith but nevertheless be considered to be substantially at the tissue.

In an exemplary embodiment, the distal end of the cannula is normal to the tissue surface through which the implant(s) and needle(s) being advanced from the cannula are to be advanced, thereby allowing the implant(s) and needle(s) to be advanced through the tissue at the intended point and providing a mechanical advantage because the implant(s) being delivered are supported.

The cannula through which the needle(s) and implant(s) are advanced can have a gripping feature at a distal end surface thereof. The gripping feature may facilitate secure positioning of the cannula's distal end substantially at the tissue in a normal position relative thereto by increasing a coefficient of friction of the cannula's distal end surface, thereby helping to reduce slippage of the cannula's distal end on the tissue. The gripping feature can have any of a variety of configurations, such as a textured surface, a sticky surface, a fabric on the cannula's distal end, etc.

An angle at which the distal end of the cannula is positioned adjacent to the tissue defines an angle at which the implant(s) and needle(s) advanced through the cannula are advanced into the tissue. Different angles may be appropriate in different surgical procedures due to any one or more factors, such as different patient sizes, different tissue surface geometries between patients, and different implant sizes. A cannula may be advanced into a patient to achieve the cannula angle desired for the surgical procedure being performed. However, a cannula may not be advanced into the patient to achieve the desired cannula angle for any one or more reasons, such as unexpected patient anatomy, surgeon inexperience, improper visualization of the surgical space, the cannula is being used to deliver devices that need different angles of approach, etc. The cannula may therefore need to be advanced into the patient multiple times before the desired cannula angle is achieved, which may prolong a length of the surgical procedure, cause unnecessary tissue trauma, and/or increase chances of causing patient injury.

The cannula through which the needle(s) and implant(s) are advanced can be non-steerable or steerable. In general, a non-steerable cannula has a fixed angulation at its distal end. In general, a steerable cannula has a variable angulation at its distal end. The angle at which the distal end of the cannula approaches a tissue may thus be adjusted within a patient's body, which may facilitate desired angular positioning of the cannula's distal end relative to the tissue and help the cannula's distal end be positioned normal to the tissue's surface. The variable angle can, in an exemplary embodiment, be in a range of −90 to 90 degrees, e.g., in a range of about −60 to 60 degrees.

A steerable cannula can include a feedback mechanism configured to provide at least one of a visual, tactile, and audible signal to a user of the steerable cannula indicating a current angle of the steerable cannula's distal end. The current angle can be indicated, for example, audibly (e.g., via clicks that occur every 15° or some other predetermined increment) and visually (e.g., with a marking line on the rotary knob and indicial markings on the static handle).

A steerable cannula can include an outer tube and an inner tube concentrically disposed in the outer tube. The distal ends of the inner and outer tubes can be fixed together, e.g., welded together, attached together with adhesive, being integrally formed together, etc. The outer tube can be configured to move relative to the inner tube and thereby causing a distal portion of the cannula to articulate at an angle. The movement of the outer tube can include rotation of the outer tube about a longitudinal axis thereof, with a direction of the outer tube's rotation, e.g., clockwise or counterclockwise, defining whether the cannula's distal portion articulates right or left. In another embodiment, the movement of the outer tube can include pushing the outer tube distally and pulling the outer tube proximally, the direction (proximal or distal) defining whether the cannula's distal portion articulates right or left.

FIG. 91 illustrates one embodiment of an inner tube 272 of a steerable cannula (shown transparent for ease of illustration). FIG. 91 also illustrates disposed in an inner lumen of the inner tube 272 an implant 274 coupled to a needle 276 and to a suture 278. The inner tube 272 has a plurality of slits 280 formed in one side thereof in a distal portion thereof. The inner tube 272 includes five slits 280 but can have another number of slits 280. The plurality of slits 280 are configured to allow bending of the inner tube 272 along a length of the cannula including the slits 280, e.g., allow bending in the distal portion of the cannula that includes the slits 280. The deeper the slits 280 and the wider the slits 280, the easier it is to bend the inner tube 272 at the slits 280 (e.g., the less force that need be applied to move the outer tube) because the slits 280 provide less resistance to bending of the inner tube 272. In an exemplary embodiment, the slits 280 are shallow and have a narrow width so as to make it more difficult to bend the inner tube 272. Making the inner tube 272 more difficult to bend may help reduce kickback of the cannula when advancing the needle 276 and the implant 274 disposed therein through tissue at which the cannula's distal end is positioned, thereby helping to ensure that the needle 276 and implant 274 are advanced through the tissue at the desired point.

The steerable cannula also includes an outer tube (not shown) having a distal end fixed to a distal end of the inner tube 272. The outer tube can have a plurality of slits formed in one side thereof opposite to the side in which the plurality of slits 280 are formed in the inner tube 272, e.g., offset 180° from the slits 280 of the inner tube 272. As mentioned above, depending on a movement of the outer tube relative to the inner tube 272, the cannula will either bend one way in response to the slits 280 of the inner tube being compressed and allowing bending or in an opposite way in response to the slits of the inner tube 272 being separated and allowing bending.

FIG. 92 illustrates one embodiment of a non-steerable cannula 282. FIG. 92 also illustrates disposed in an inner lumen of the cannula 282 an implant 274 coupled to a needle 276 and to a suture 278 (the same implant, needle, and suture as in FIG. 91). The non-steerable cannula 282 has a fixed curvature in a distal portion thereof so as to be bent at a non-zero angle relative to its longitudinal axis. The non-steerable cannula 282 can be provided in a kit including one or more additional non-steerable cannulas with each non-steerable cannula in the kit having a different fixed curvature (all non-zero curvatures, or one zero curvature and one or more non-zero curvatures) in a distal portion thereof. A surgeon may select one of the non-steerable cannulas having a desired curvature for use in a performance of a particular surgical procedure being performed on a particular patient. Different ones of the non-steerable cannulas can be used in the course of that same surgical procedure, thereby allowing different angles of approach to be achieved.

FIG. 93 illustrates another embodiment of a non-steerable cannula 284. FIG. 93 also illustrates disposed in an inner lumen of the cannula 284 an implant 274 coupled to a needle 276 and to a suture 278 (the same implant, needle, and suture as in FIG. 91). The cannula 284 is the same as the cannula 282 of FIG. 92 except that the cannula 284 of FIG. 93 has a longitudinal slot 286 formed through a sidewall thereof that is in communication with an inner lumen of the cannula 284. The slot 286 can be configured to have a suture extend therethrough, as shown in FIG. 93 in which the suture 278 extends through the slot 286. In an exemplary embodiment, the slot 286 extends along an entire longitudinal length of the cannula 284, thereby allowing the needle(s) and implant(s) couple to the suture 278 to be inserted into the cannula 284 through an open proximal end thereof with the suture 278 extending through the slot 286 as the needle(s) and implant(s) are advanced to the distal end of the cannula 284 and, eventually, out of the cannula 284. The slot 286 is straight in this illustrated embodiment, but the slot 286 may spiral around the cannula 284 or otherwise not be straight along the cannula 284. The slot 286 may reduce chances of the suture 278 tangling with the needle(s) and implant(s) as the needle and implant are advanced through and out of the cannula 284, may facilitate delivery of a protective member coupled to the suture 278 since the protective member (e.g., the protective member of FIG. 32 or FIG. 33) can be located outside of the cannula 284, and/or may facilitate delivery of a suture coupled to multiple implants since a length of the suture connecting the implant within the cannula 284 to one or more other implants outside the cannula 284 can extend through the slot 286. The protective member may be too large to fit within the cannula 284 without increasing a diameter of the cannula 284, which is generally undesirable since it would require a larger incision to be made in the patient to insert the cannula 284 into the patient and/or would make the cannula 284 more difficult to desirably position within a tight surgical space. The slot 286 thus allows a construct including a protective member to be delivered using a cannula 284.

The cannula 284 of FIG. 93 may be provided in a kit similar to that discussed above regarding the cannula 282 of FIG. 92. A kit can include any number (including zero) non-steerable cannulas having a longitudinal slot and any number (including zero) non-steerable cannulas lacking a longitudinal slot, as long as the kit includes at least two non-steerable cannulas.

Figure 96:
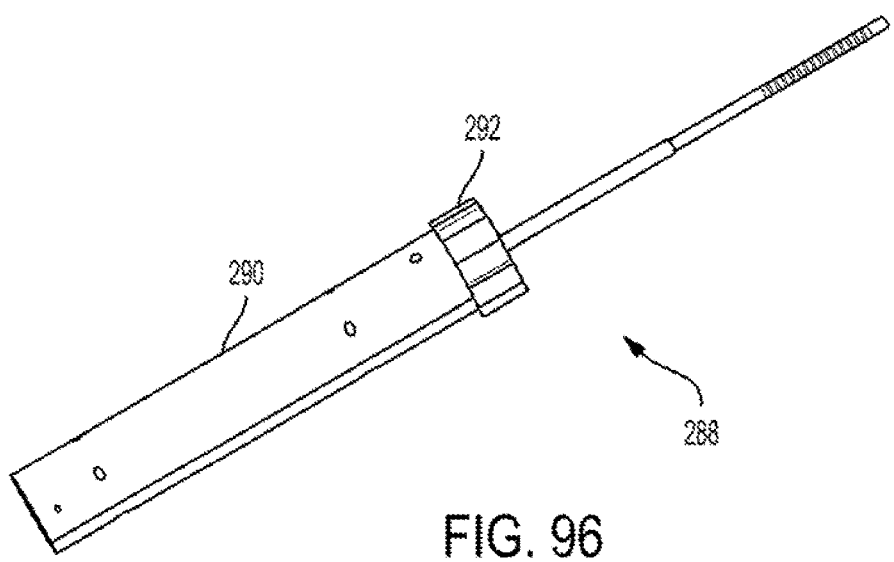
FIG. 96 is a perspective view of another embodiment of a steerable cannula.
Figure 97:
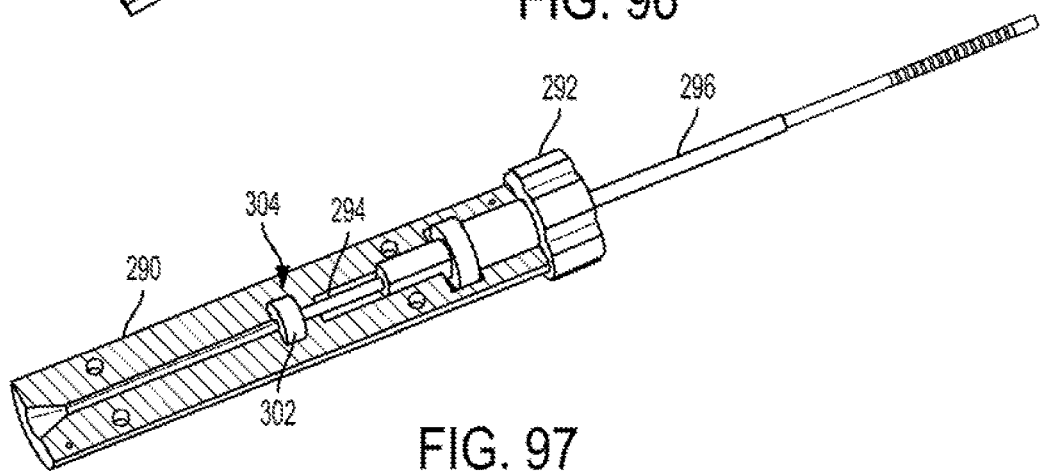
FIG. 97 is a perspective cross-sectional view of the steerable cannula of FIG. 96.
Figure 98:
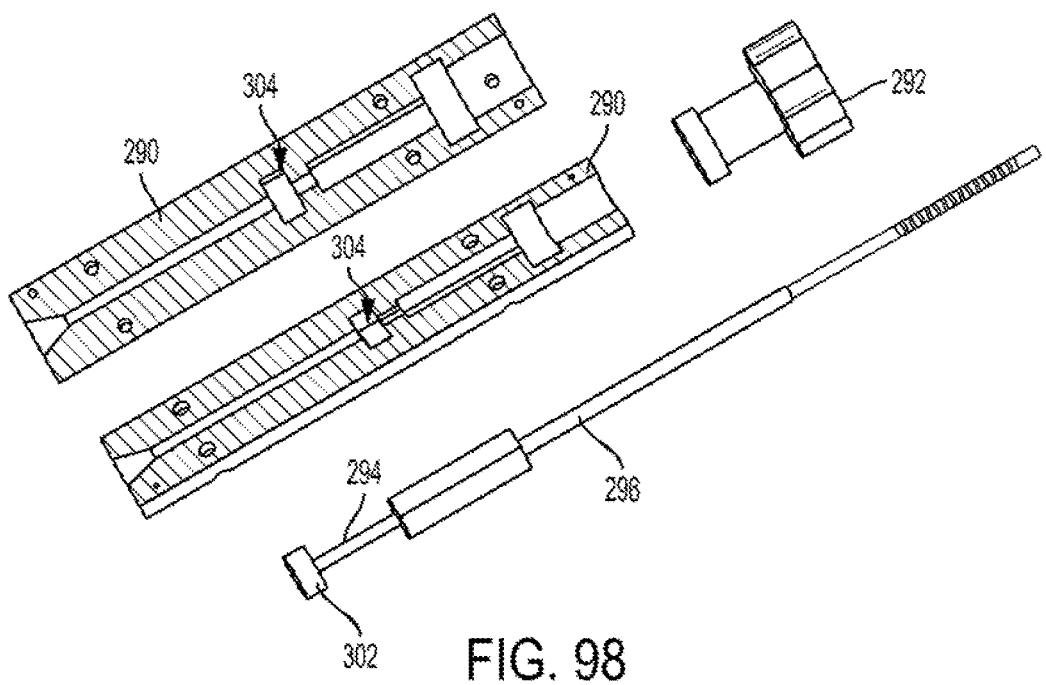
FIG. 98 is a perspective exploded view of the steerable cannula of FIG. 96.
Figure 99:
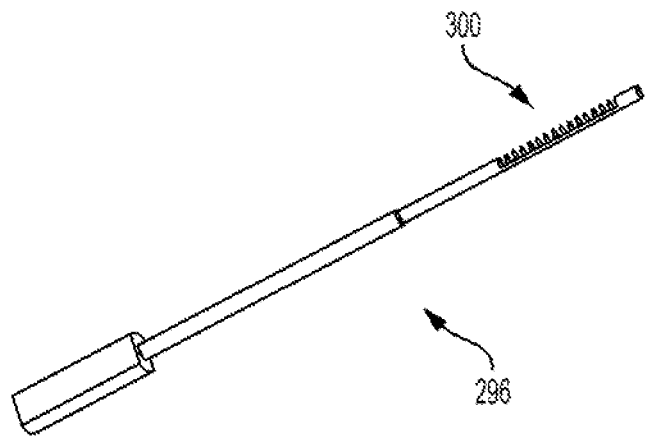
FIG. 99 is a perspective view of an outer tube of the steerable cannula of FIG. 96.
Figure 100:
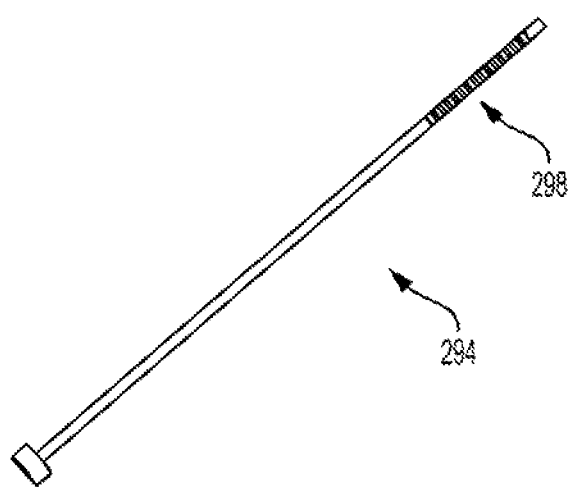
FIG. 100 is a perspective view of an inner tube of the steerable cannula of FIG. 96.
Figure 101:
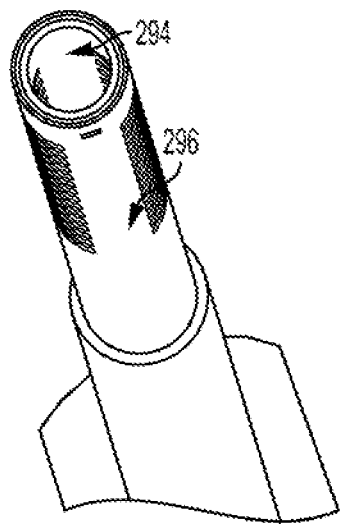
FIG. 101 is a perspective view of a distal portion of the steerable cannula of FIG. 96.
Figure 102:
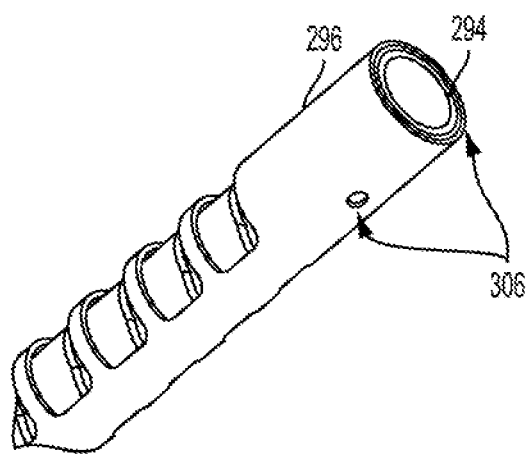
FIG. 102 is another perspective view of the distal portion of the steerable cannula of FIG. 96.

FIGS. 96 and 97 illustrate an embodiment of a steerable cannula 288 that includes a handle 290, an actuator in the form of a steering knob 292, and inner and outer tubes 294, 296 extending distally from the handle 290 and knob 292. FIG. 97 shows the cannula 288 of FIG. 96 with the handle 290 in cross-section. FIG. 98 shows the cannula 288 of FIG. 96 in an exploded view. FIG. 99 shows the outer tube 296 of the cannula 288 of FIG. 96 as a standalone element. FIG. 100 shows the inner tube 294 of the cannula 288 of FIG. 96 as a standalone element. FIG. 101 shows a perspective view of a distal portion of the cannula 288 of FIG. 96. FIG. 102 shows a perspective view of a distal portion of the inner and outer tubes 294, 296 of the cannula 288 of FIG. 96.

As shown in FIGS. 99 and 100, the inner tube 294 has a plurality of cutouts 298 in the form of slits formed in one side thereof in a distal portion thereof, and the outer tube 296 has a plurality of cutouts 300 in the form of slits formed in an opposite side thereof in a distal portion thereof. The distal ends of the inner and outer tubes 294, 296 are attached together via welding 306, as shown in FIG. 102, although the tubes 294, 296 can be attached together in other ways, as mentioned above. The outer tube 296 of the cannula 288 is configured to move relative to the inner tube 294 to articulate a distal end of the cannula 288. The knob 292 is operatively coupled to the outer tube 296 via corresponding threads on the knob 292 and the outer tube 296. The knob 292 is configured to be actuated, e.g., rotated, to cause the outer tube's movement relative to the inner tube 294 by threadably moving the outer tube 296. The inner tube 294 is held in a fixed position relative to the handle 290 due to a proximal coupling element 302 at a proximal end of the inner tube 294, shown in FIGS. 97, 98 and 100, being seated at a fixed position along the cannula's longitudinal axis in a depression 304 formed in the handle 290, as shown in FIG. 97. Thus, the inner tube 294 stays at a fixed axial position while the outer tube 296 rotates and moves longitudinally in response to the actuation of the knob 292, thereby causing the distal portion of the cannula 288 to articulate in the area of the cutouts 298, 300.

Figure 103:
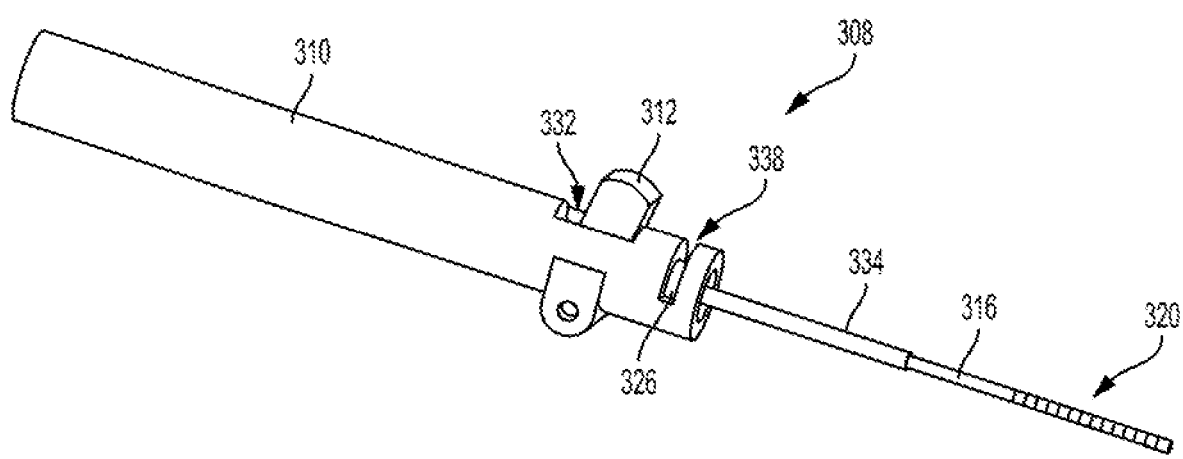
FIG. 103 is a perspective view of anther embodiment of a steerable cannula.
Figure 104:
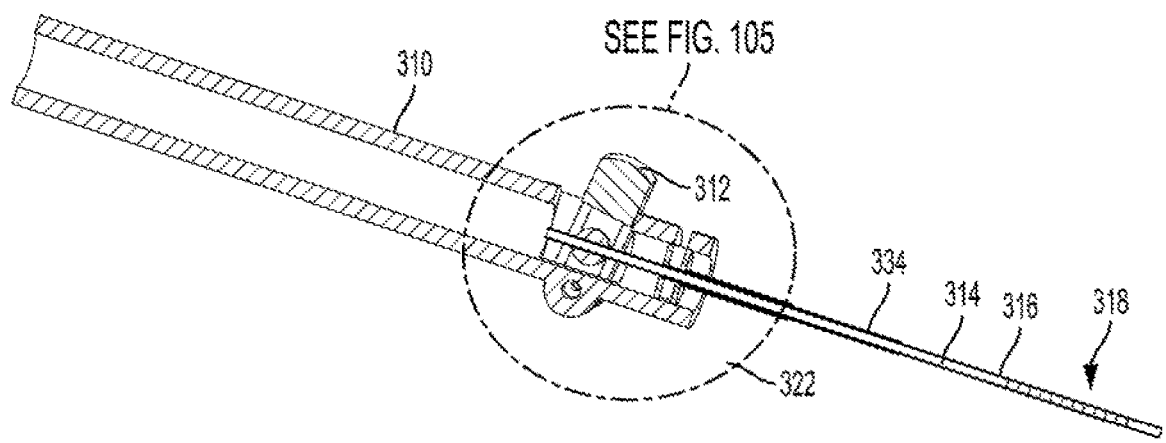
FIG. 104 is a cross-sectional view of the steerable cannula of FIG. 103.

FIGS. 103 and 104 illustrate an embodiment of a steerable cannula 308 that includes a handle 310, an actuator 312 in the form of a lever, and inner and outer tubes 314, 316 extending distally from the handle 310. FIG. 104 shows the cannula 308 of FIG. 103 in cross-section. The inner tube 314 has a plurality of cutouts 318 in the form of slits formed in one side thereof in a distal portion thereof, and the outer tube 316 has a plurality of cutouts 320 in the form of slits formed in an opposite side thereof in a distal portion thereof. Distal ends of the inner and outer tubes 314, 316 are fixed together, e.g., welded together, attached together with adhesive, being integrally formed together, etc.

Figure 105:
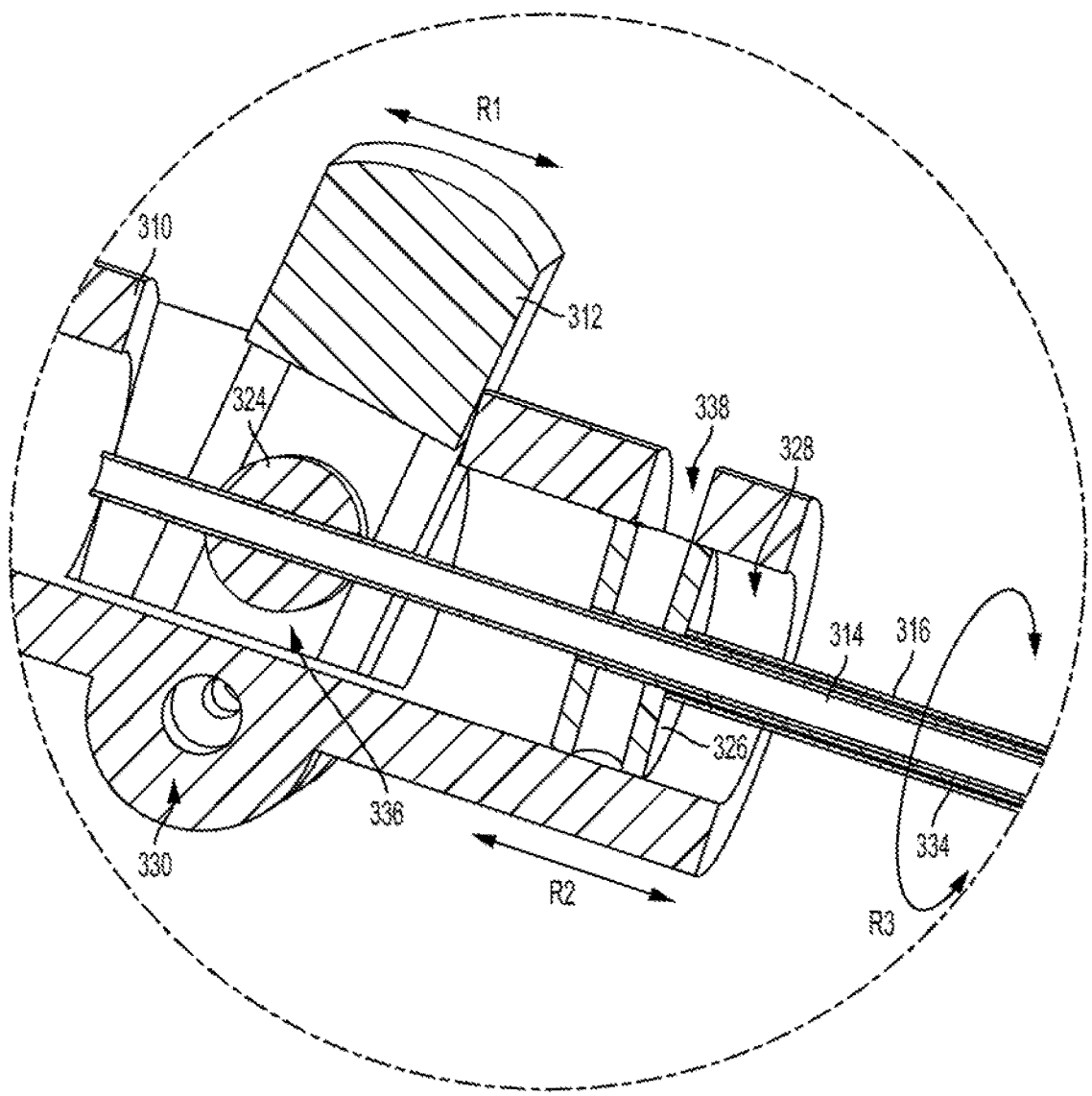
FIG. 105 is a view of a portion of the steerable cannula of FIG. 104 including arrows indicative of movement.

The outer tube 316 is configured to move relative to the inner tube 314 to articulate a distal end of the cannula 308, similar to the articulation of steerable cannulas discussed above. The cannula 308 includes a drive assembly 322 configured to facilitate the articulation of the distal end of the cannula 308 by causing movement of the inner tube 314 relative to the outer tube 316. The drive assembly 322 includes, as also shown in FIG. 105, the lever 312 and a coupling element 324 in the form of a spherical ball. The coupling element 324 is fixed to the inner tube 314 with the inner tube 314 extending through the ball 324, as shown in FIG. 105.

Figure 106:
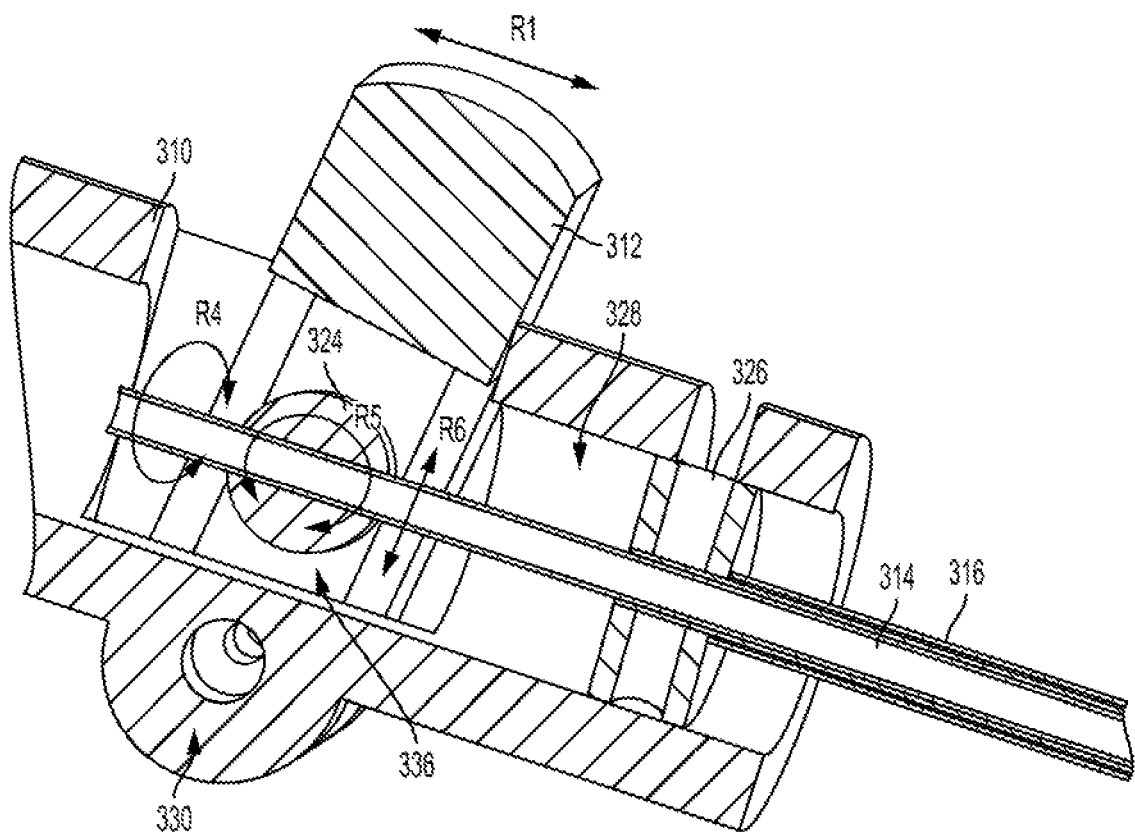
FIG. 106 is another view of the portion of the steerable cannula of FIG. 105 including arrows indicative of movement.

The lever 312 is configured to be actuated, e.g., moved proximally and distally as shown by arrow R1 in FIGS. 105 and 106, to cause the inner tube's movement relative to the outer tube 316 by translating the inner tube 314 proximally (in response to the lever 312 being moved proximally) and distally (in response to the lever 312 being moved distally). The lever 312 is pivotally attached to the handle 310 at a pivot point 330 about which the lever 312 pivots in response to movement of the lever 312 from outside the handle 310, e.g., from user movement of the lever 312 selectively back and forth. The pivoting of the lever 312 may provide a mechanical advantage that eases articulation of the cannula's distal end. The lever 312 extends from within the handle 310 through a slot 332 (see FIG. 103) formed in the handle 310 to facilitate user access to and manipulation of the lever 312. The outer tube 316 is held in a fixed position relative to the handle 310 due to a distal coupling element 326 at a distal end of the outer tube 316. The distal coupling element 326 is fixed to the handle 310 within an inner cavity 328 thereof so as to hold the outer tube 316 at a fixed position along the cannula's longitudinal axis. Thus, the outer tube 316 stays at a fixed axial position while the inner tube 314 translates and moves longitudinally, as shown by arrow R2 in FIG. 105, in response to the actuation of the lever 312, thereby causing the distal portion of the cannula 308 to articulate in the area of the cutouts 318, 320. The ball 324 and a bottom portion of the lever 312 are also disposed in the handle's inner cavity 328, as shown in FIGS. 105 and 106.

The inner and outer tubes 314, 316 are configured to rotate about a shared longitudinal axis thereof relative to the handle 310, as shown by arrow R3 in FIG. 105 and arrow R4 in FIG. 106. This rotation may facilitate positioning of the cannula's distal end at a desired orientation relative to a target tissue. A support tube 334 disposed around a distal portion of the outer tube 316, and having a distal end thereof fixed to the distal coupling element 326, is also configured to rotate with the inner and outer tubes 314, 316 about the shared longitudinal axis of the inner and outer tubes 314, 316. The lever 312 has an inner cavity 336 therein in which the ball 324 is movably disposed, as shown by arrows R4, R5, R6 in FIG. 106, so as to allow for the rotation of the inner tube 314 without causing corresponding rotation of the lever 312. The lever 312 is thus configured to remain stationary during the rotation of the inner tube 314 to maintain a longitudinal position of the inner tube 314 during its rotation. The rotation of the inner and outer tubes 314, 316 can be accomplished by manual rotation thereof, such as by manually rotating the support tube 334 from outside of the handle 310, manually rotating the outer tube 316 from outside of the handle 310, or by manually rotating the distal coupling element 326 from outside of the handle 310 through an access opening 338 formed in the handle 310 (see FIGS. 103 and 105).

Figure 107:
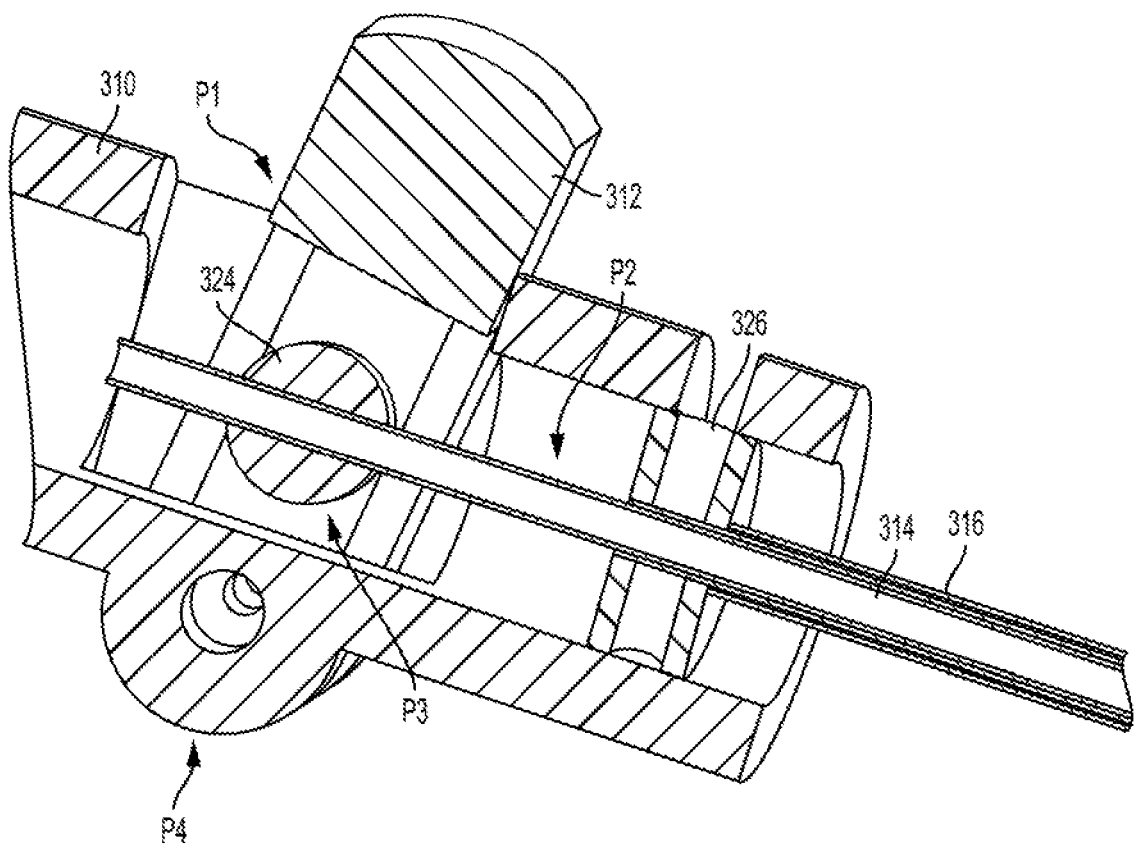
FIG. 107 is another view of the portion of the steerable cannula of FIG. 105 showing possible detent locations.

The cannula 308 can include one or more detents configured to prevent undesirable motion of various parts of the cannula 308 and thereby facilitate desirable and stable positioning of the cannula 308 relative to a target tissue. The detent can have any of a variety of configurations, such as a ball detent extending from one element of the cannula 308 and configured to slide in and out of a corresponding depression formed in another element of the cannula 308. FIG. 107 illustrates four positions P1, P2, P3, P4 at which detents may be located. The cannula 308 can have detents at any one or more of these positions P1, P2, P3, P4. The first position P1 is at an interface between the handle 310 and the lever 312. A detent at the first position P1 is configured to prevent undesired movement of the lever 312 relative to the handle 310, e.g., to hold the lever 312 in its distal-most position within the slot 332 until a user initiates movement of the lever 312. The cannula 308 can additionally or alternatively include a detent at a proximal end of the slot 332 to hold the lever 312 in its proximal-most position within the slot 332 until a user initiates movement of the lever 312. The second position P2 is at an interface between the inner tube 314 and the handle 310. A detent at the second position P2 is configured to prevent undesired translational or rotational movement of the inner tube 314 relative to the handle 310 until a user initiates such movement. The third position P3 is at an interface between the ball 324 and the lever 312. A detent at the third position P3 is configured to prevent undesired movement of the ball 324 relative to the lever 312, e.g., prevent movement of the ball 324 within the lever's inner cavity 336, and thereby help prevent unintentional rotation of the inner tube 314 and the outer and support tubes 316, 334 operatively coupled thereto. The fourth position P4 is at an interface of the lever 312 and the handle 310 by the pivot point 330. A detent at the fourth position P4 is configured to prevent undesired pivoting of the lever 312 relative to the handle 310 until such movement is initiated by a user.

In another embodiment of a steerable cannula, the steerable cannula can include inner and outer tubes configured to articulate similar to the embodiments of inner and outer tubes of steerable cannulas discussed above. The steerable cannula in this embodiment includes a wire or cable configured to be actuated to cause the articulation of the inner and outer tubes. The wire or cable can be operatively coupled to an actuator (e.g., an actuator in the form of a lever, a knob, etc.) that, when actuated, causes the wire or cable to shorten longitudinally and thereby cause the articulation. The wire or cable can be attached at its distal end to the outer tube such that the shortening of the wire or cable causes articulation of the outer tube and hence also articulation of the inner tube attached to the outer tube. The wire or cable can extend through an inner lumen of the steerable cannula, e.g., through inner lumens of both the inner and outer tubes. Alternatively, the outer tube can have an irregular cross-sectional shape to allow passage of the wire or cable therethrough outside of the inner tube but inside the outer tube, such as the outer tube having a primary, circular inner lumen area extending therethrough with a semi-circular inner lumen area projecting radially outward from the primary, circular inner lumen area, with the wire or cable extending through the semi-circular inner lumen area and the inner tube extending through the circular inner lumen area.

The inner and outer tubes can each include slits to facilitate articulation, similar to that discussed above. Alternatively or in addition to the inner tube including slits, the inner tube can be flexible and be made from a material such as nitinol or plastic (e.g., PEEK. etc.) to facilitate its articulation. If the inner tube is plastic, a distal end of the inner tube can have a bevel edge or can have a cannulated metal tip joined thereto to facilitate passage of the inner tube through tissue. The inner tube can be configured to move longitudinally relative to the outer tube.

In use, after being advanced to a target site, such as to a position at a joint, the outer tube can be articulated to determine an optimal angle of articulation for implant delivery and placed adjacent to a tissue surface for implant delivery. The inner tube can then be advanced distally relative to the outer tube by actuating an inner tube actuator operatively coupled thereto (e.g., by sliding a lever, rotating a knob, etc.) such that the inner tube pierces the tissue surface, e.g., pierces through a peripheral rim of a meniscus tissue. A first implant can then be advanced distally through the inner tube via actuation of an implant actuator (such as a flexible actuator) until the implant moves distally beyond the inner tube to allow the first implant to toggle behind the tissue, e.g., behind the meniscus. The actuator can then return to a position behind a second implant, initially loaded proximal to the first implant, due to a biasing member such as a spring. The inner tube can then be withdrawn to a mating position with a distal portion of the outer tube, thereby allowing the cannula to be repositioned relative to the tissue for delivery of the second implant. The implant delivery process can then be repeated for the second implant, e.g., articulate the outer tube, advance the inner tube, advance the second implant, and withdraw the inner tube. In another embodiment, the outer tube can be replaced by a steerable cannula described above, e.g., no wire or cable actuation.

Lockable Cannulas

A cannula configured to have advanced therethrough a delivery system that delivers one or more needles and one or more implants through tissue can be configured to be lockable relative to tissue through which the cannula is inserted and/or relative to the delivery system. The lockability of the cannula may help hold the cannula's distal end substantially at the tissue, e.g., hold the cannula's distal end normal to the tissue's surface, which may help ensure that the needle(s) and the implant(s) are advanced through the tissue at a desired point. The lockability of the cannula may help reduce kickback of the cannula during delivery of the implant(s) and needle(s), which may help increase surgeon confidence that the needle(s) and the implant(s) are being advanced through the tissue at a desired point since kickback can be tactilely felt by the surgeon and typically indicates that the cannula is shifting in position during deployment of the needle(s) and implant(s).

In at least some embodiments, a delivery system can be configured to be lockable relative to tissue through which it is inserted similar to the lockability of cannulas discussed herein. In such a case, the delivery system need not be advanced through a cannula since the delivery system can itself be configured to lock itself in position relative to tissue through which it is advanced to be positioned adjacent to target tissue through which implant(s) and needle(s) will be advanced.

Figure 108:
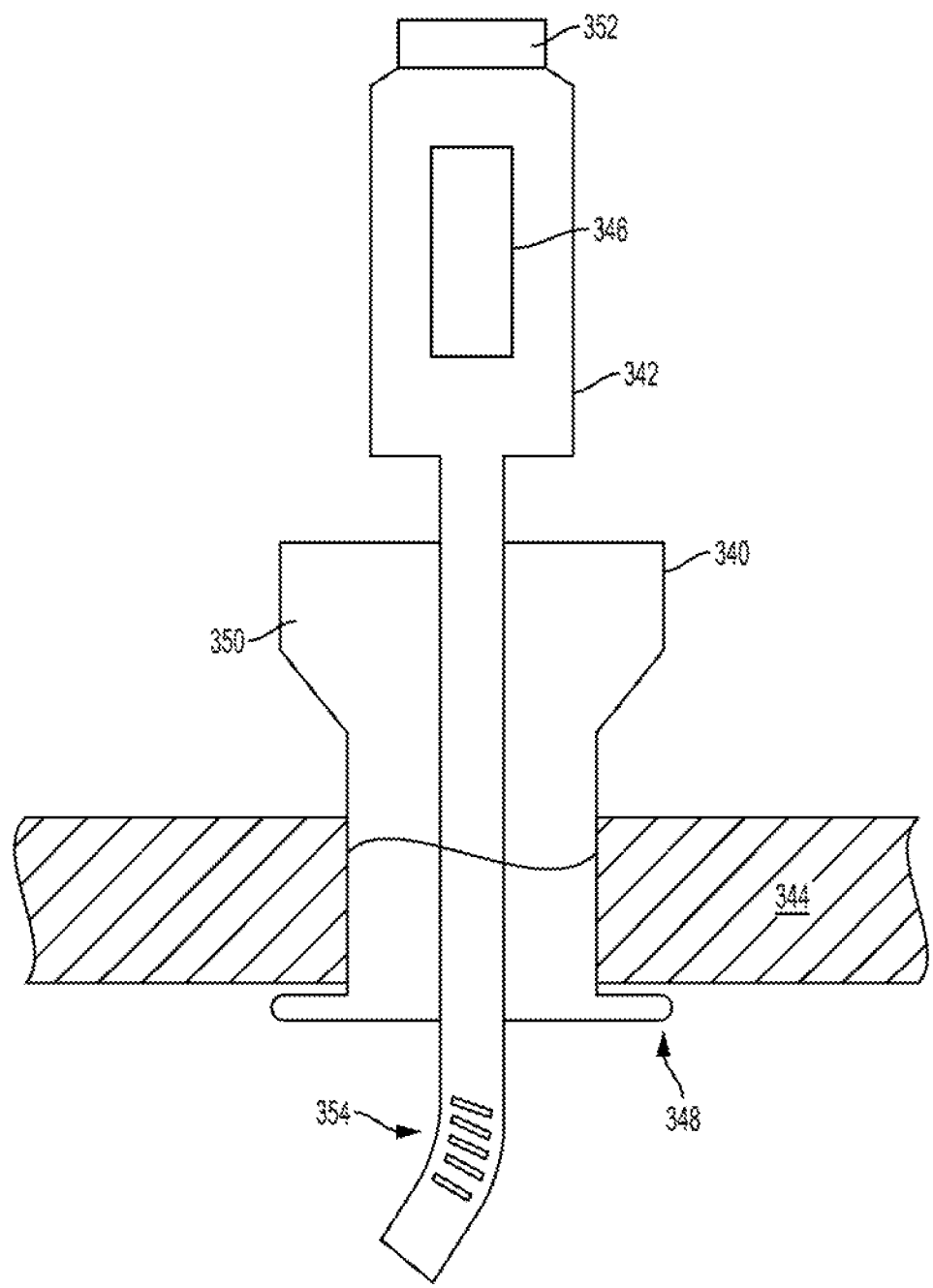
FIG. 108 is a side, partially transparent schematic view of one embodiment of a lockable cannula positioned in tissue.

FIG. 108 illustrates one embodiment of a cannula 340 configured to be lockable relative to a delivery system 342 and relative to tissue 344 in which the cannula 340 is positioned. The delivery system 342 of FIG. 108 includes a thumb slide 346 configured to deploy implant(s) from the system 342, as discussed herein. The delivery system 342 of FIG. 108 is an example of a delivery system that can be advanced through the cannula 340. Other delivery systems can be so advanced, such as the delivery systems of FIGS. 56, 82 (and 69), and 82.

The cannula 340 includes a distal retention feature 348, in the form of a distal lip, configured to engage a distal surface of tissue 344 through which the cannula 340 has been advanced and in which the cannula 340 is positioned and thereby lock the cannula 340 relative thereto. The distal retention feature 348 can be configured to cooperate with the tissue 344 to reduce kickback of the cannula 340 during deployment of the needle(s) and implant(s) from the delivery system 342. The distal retention feature 348 can be configured to deployed into positioned after being advanced through the tissue 344, similar to that discussed below regarding the deployment of the retention feature of FIG. 110. In other embodiments, the distal retention feature can be malleable, e.g., be formed of a gel material similar to a gel seal, to facilitate insertion of the distal retention feature in a collapsed state through the tissue while allowing the distal retention feature to return to its default expanded state after passage through the tissue.

The cannula 340 includes a proximal retention feature 350, in the form of a soft material forming a proximal portion of the cannula 340, configured to engage the delivery system 342 advanced through the cannula 340. One example of such as soft material is a poly urethane (non-crystalline) material. The proximal retention feature 350 can increase a coefficient of friction of the cannula 340 and thereby lock the delivery system 342 relative thereto via friction relationship until a force is applied to the delivery system 342 that overcomes the frictional force, e.g., until the delivery system 342 is pulled proximally or pushed distally with enough force to overcome the frictional force. The distal retention feature 348 is also formed of the soft material and is sufficiently flexible for insertion into soft tissue yet rigid enough to prevent the cannula 340 from pulling out of the soft tissue during delivery system manipulation.

The steering actuation is an actuator 352 configured to be actuated to effect bending of the cannula's distal end where slots 354 are shown in FIG. 108. The actuator 352 is actuated by rotation.

FIG. 109 illustrates one embodiment of a delivery system 356 configured to be lockable relative to tissue 358 in which the delivery system 356 is positioned. The delivery system 356 includes a plurality of retention features 360 formed on an exterior surface thereof that are configured to engage the tissue 358 in which the delivery system 356 is positioned. The exterior of the delivery system 356 may thus not be smooth. The retention features 360 are configured to help hold the delivery system 356 in position in the tissue 358 by penetrating into the tissue 358, and the retention features 360 are configured to reduce kickback of the delivery system 356 during deployment of the needle(s) and implant(s) from the delivery system by holding the delivery system 356 in position relative to the tissue 358. The retention features 360 can have a variety of configurations, such as barbs (as in this illustrated embodiment) or other protrusions (e.g., ribs, spikes, a thread, etc.) extending radially outward from the delivery system 356, a textured surface, a sticky surface, etc. The retention features 360 can be formed on the delivery system 356 in any of a variety of ways, such as by being overmolded thereon. The retention features 360 can be made from the same material as a remainder of the delivery system 356 (e.g., stainless steel, PEEK, etc.) or from a different material as the remainder of the delivery system 356.

FIGS. 110A and 110B illustrate an embodiment of a cannula 362 configured to be lockable relative to tissue in which the cannula 362 is positioned. The cannula 362 includes a retention feature 364, in the form of a distal lip, configured to engage a distal surface of tissue through which the cannula 362 has been advanced and in which the cannula 362 is positioned and thereby lock the cannula 362 relative thereto. The distal retention feature 364 can be configured to cooperate with the tissue to reduce kickback of the cannula 362 during deployment of the needle(s) and implant(s) from the delivery system. A proximal portion 366 of the cannula 362 is coupled to an actuator in the form of a rotating cap 368, which is part of a second cannula inserted into the cannula 362, configured to deploy the distal retention feature 364 after the distal retention feature 364 is advanced through the tissue, thereby allowing the distal retention feature 364 to have a smaller size during insertion/removal to facilitate minimally invasive use and/or to allow selectable size of the distal retention feature 364 in view of available space within the patient's body. Rotating the cap 368 relative to a distal base, e.g., the proximal portion 366 of the cannula 362, in a first direction (e.g., clockwise) causes the distal lip 364 to expand and radially create an "iris," as shown in FIG. 110B. The iris is created by two discs, one rotatable and one stationary. Actuating the cap 368 rotates the rotatable disc relative to the stationary disc. The iris is configured to allow positional movement of the delivery system when actuated (e.g., when the iris is open). Rotating the cap 368 relative to the distal base in a second, opposite direction (e.g., counterclockwise) causes the distal lip 364 to contract and "dilate" the "iris," which may facilitate removal of the cannula 362 from the tissue after the "iris" has been expanded. The iris is configured to limit positional movement of the delivery system when contracted.

FIG. 111A illustrates one embodiment of a cannula 370 configured to be lockable relative to a delivery system 372.

The cannula 370 includes an internal mating feature 374 (obscured in FIG. 111A and in the form of a "J" lock 374 in this illustrated embodiment, as shown in FIG. 111B) configured to releasably lock with a corresponding external mating feature 376 of the delivery system 372. The external mating feature 376 in this illustrated embodiments is two over-molded tabs on the delivery system 372 that rotationally engage the "J" lock 374 (which is molded on the cannula 370 in the inner diameter thereof) to secure the delivery system 372 within the cannula 370, thereby keeping the delivery system 372 stable during implant insertion.

FIG. 112 illustrates another embodiment of a cannula 378 configured to be lockable relative to a delivery system 380. The cannula 378 includes a mating feature 382 (in the form of a plurality of holes in this illustrated embodiment) configured to releasably lock with a corresponding mating feature 384 of the delivery system 380 (a spring-loaded detent button in this illustrated embodiment). The detent button 384 can be locked within any one of the holes 382 to secure the delivery system 380 at a desired position within the cannula 378. The cannula 378 can instead include only one hole 382, thereby providing one predetermined locked position of the delivery system 380 within the cannula 378.

Figure 113:
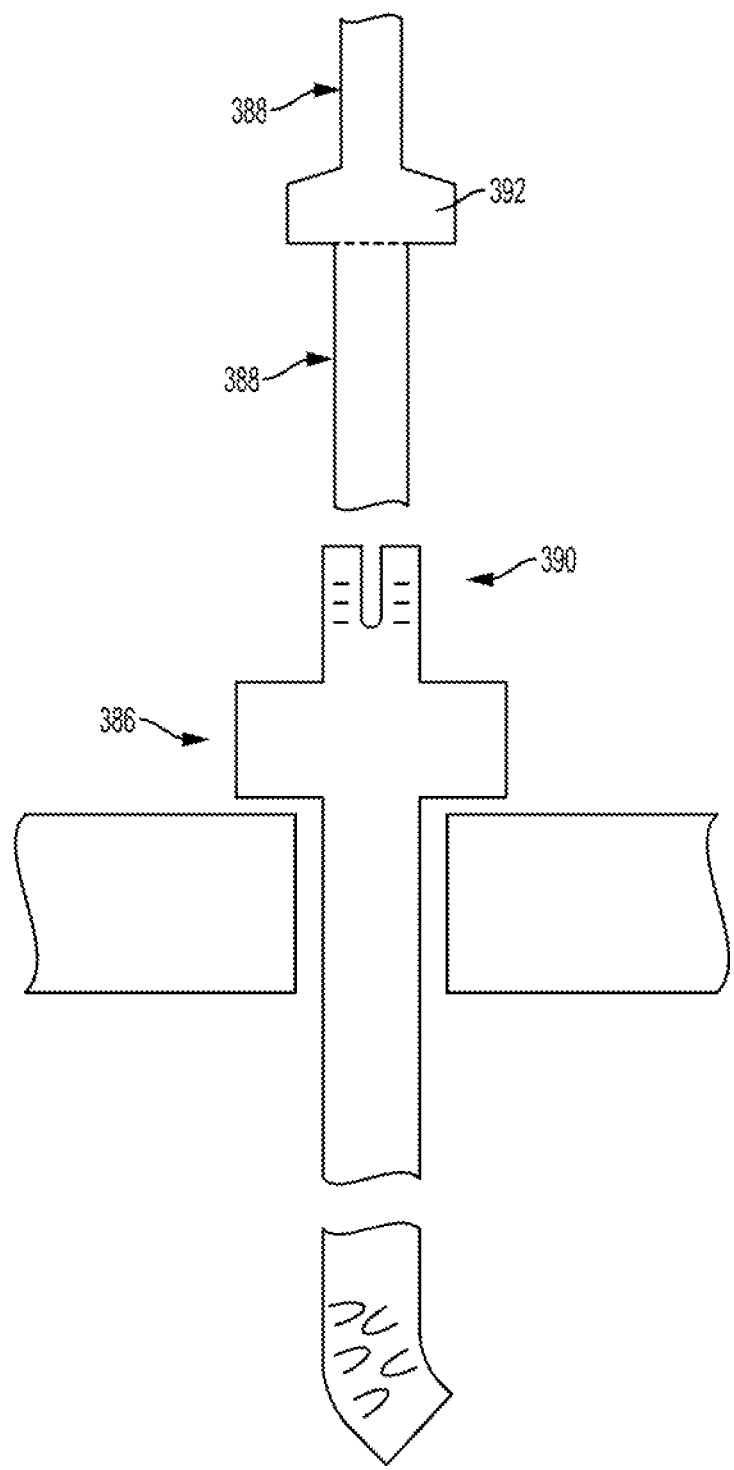
FIG. 113 is a side schematic view of another embodiment of a lockable cannula positioned in tissue and with a delivery system configured to be locked thereto.

FIG. 113 illustrates another embodiment of a cannula 386 configured to be lockable relative to a delivery system 388. The cannula 386 includes a mating feature 390 in the form of a plurality of radially-arranged vertical slots configured to releasably lock via compression fit with a slidable locking nut 392 of the delivery system 388. The compression nut 392, when slid to engage the mating feature 390, compresses the cannula 386 to secure thereto.

CONCLUSION

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical method, comprising:
advancing a cannula through tissue of a patient such that a proximal portion of the cannula is located outside of the patient and a distal portion of the cannula is located within the patient, the cannula including concentric inner and outer tubes that have distal ends fixed together;
with the distal portion of the cannula located within the patient, causing the distal portion to bend at an angle relative to a target tissue within the patient by moving the outer tube relative to the inner tube, wherein causing the distal portion to bend at the angle includes rotating an actuator that has threads thereon that are threadably engaged with threads on the outer tube, thereby causing longitudinal translation of the outer tube relative to the inner tube; and
after causing the distal portion to bend, advancing a surgical device through the cannula;
wherein the inner and outer tubes each extend distally from a handle of the cannula; and
with the outer tube longitudinally translatinu relative to the inner tube the outer tube is also longitudinally translatint relative to the handle and the inner tube is held in a fixed ositon relative to the handle by a proximal coupling element fixed to the inner tube and seated in a depression formed in an interior of the handle.

2. The method of claim 1, wherein the cannula is advanced through the tissue with the distal portion at a zero angle, and the angle to which the cannula is bent is a non-zero angle.

3. The method of claim 1, wherein the cannula is bent from one non-zero angle to another non-zero angle.

4. The method of claim 1, wherein the cannula is bent from a non-zero angle to a zero angle.

5. The method of claim 1, wherein the surgical device includes a needle coupled to at least one pledget and at least one suture attached to the at least one pledget, the needle being configured to guide the at least one pledget and the at least one suture through a tissue.

6. The method of claim 1, wherein the target tissue is a meniscus.

7. The method of claim 1, wherein the tissue is at one of a knee, a hip, and a shoulder of the patient.

8. A surgical method, comprising:
advancing a cannula through tissue of a patient such that a proximal portion of the cannula is located outside of the patient and a distal portion of the cannula is located within the patient; and
advancing a surgical device through the cannula;
wherein the cannula includes a locking mechanism configured to lock the cannula in position relative to the surgical device advanced therethrough, and the cannula is automatically locked in position relative to the surgical device advanced therethrough;
the cannula also includes a second locking mechanism configured to lock the cannula in position relative to the tissue through which the cannula has been advanced; and
the method further comprises actuating an actuator to cause the cannula to be locked in position relative to the tissue.

9. A surgical method, comprising:
advancing a cannula through tissue of a patient such that a proximal portion of the cannula is located outside of the patient and a distal portion of the cannula is located within the patient, wherein the cannula includes concentric inner and outer tubes that have distal ends fixed together, the outer tube being configured to longitudinally translate, along a longitudinal axis of the outer tube, relative to the inner tube and thereby cause a distal portion of the cannula to articulate;
advancing a surgical device through the cannula; and
rotating an actuator that is threadably engaged with the outer tube, thereby causing longitudinal translation of the outer tube relative to the inner tube;
wherein the cannula includes at least one of a first locking mechanism configured to lock the cannula in position relative to the tissue through which the cannula has been advanced, and a second locking mechanism configured to lock the cannula in position relative to the surgical device advanced therethrough; and
wherein the rotation of the actuator also causes rotation of the outer tube relative to the inner tube.

10. The method of claim 8, wherein the surgical device includes a needle coupled to at least one pledget and at least one suture attached to the at least one pledget, the needle being configured to guide the at least one pledget and the at least one suture through a tissue.

11. The method of claim 1, wherein the cannula includes at least one of a first locking mechanism configured to lock the cannula in position relative to the tissue through which the cannula has been advanced, and a second locking mechanism configured to lock the cannula in position relative to the surgical device advanced therethrough.

12. The method of claim 9, wherein the surgical device includes a needle coupled to at least one pledget and at least one suture attached to the at least one pledget, the needle being configured to guide the at least one pledget and the at least one suture through a tissue.

13. The method of claim 9, wherein the cannula includes the second locking mechanism, and the cannula is automatically locked in position relative to the surgical device advanced therethrough.

14. The method of claim 9, wherein the cannula includes the second locking mechanism, and the method further comprises actuating an actuator to cause the cannula to be locked in position relative to the surgical device advanced therethrough.

15. The method of claim 9, wherein the cannula includes the first locking mechanism.

16. The method of claim 8, wherein the cannula includes concentric inner and outer tubes that have distal ends fixed together, the outer tube being configured to longitudinally translate, along a longitudinal axis of the outer tube, relative to the inner tube and thereby cause a distal portion of the cannula to articulate; and
the method further comprises rotating an actuator that is threadably engaged with the outer tube, thereby causing longitudinal translation of the outer tube relative to the inner tube.

\* \* \* \* \*